(12) United States Patent
Hansen

(10) Patent No.: US 8,952,021 B2
(45) Date of Patent: Feb. 10, 2015

(54) COMPOUNDS FOR THE PREVENTION AND TREATMENT OF CARDIOVASCULAR DISEASE

(75) Inventor: Henrik C. Hansen, Calgary (CA)

(73) Assignee: Resverlogix Corp., Calgary, Alberta (CA)

( * ) Notice: Subject to any disclaimer, the term of this patent is extended or adjusted under 35 U.S.C. 154(b) by 566 days.

(21) Appl. No.: 13/143,757

(22) PCT Filed: Jan. 8, 2010

(86) PCT No.: PCT/IB2010/000159
§ 371 (c)(1),
(2), (4) Date: Aug. 18, 2011

(87) PCT Pub. No.: WO2010/079431
PCT Pub. Date: Jul. 15, 2010

(65) Prior Publication Data
US 2011/0294807 A1    Dec. 1, 2011

Related U.S. Application Data

(60) Provisional application No. 61/143,276, filed on Jan. 8, 2009.

(51) Int. Cl.
  *A61K 31/517* (2006.01)
  *A61K 31/519* (2006.01)
  *C07D 239/91* (2006.01)
  *C07D 401/04* (2006.01)
  *C07D 403/04* (2006.01)
  *C07D 471/04* (2006.01)

(52) U.S. Cl.
  CPC ............ *C07D 239/91* (2013.01); *A61K 31/517* (2013.01); *C07D 401/04* (2013.01); *C07D 403/04* (2013.01); *C07D 471/04* (2013.01)
  USPC ...................................................... 514/266.3

(58) Field of Classification Search
  CPC .. C07D 401/04; C07D 403/04; C07D 471/04; A61K 31/517
  USPC ...................................................... 514/266.3
  See application file for complete search history.

(56) References Cited

U.S. PATENT DOCUMENTS

| | | | |
|---|---|---|---|
| 2,065,593 A | 12/1936 | Lubs | |
| 2,065,900 A | 12/1936 | Laska et al. | |
| 2,071,329 A | 2/1937 | Brown | |
| 3,251,837 A | 5/1966 | Holland | |
| 3,600,394 A | 8/1971 | Coyne et al. | |
| 3,773,946 A | 11/1973 | Creger | |
| 3,930,024 A | 12/1975 | Creger | |
| 3,965,128 A | 6/1976 | Fürst et al. | |
| 4,613,593 A | 9/1986 | Yamatsu et al. | |
| 4,689,344 A | 8/1987 | Bar-Tana | |
| 4,711,896 A | 12/1987 | Bar-Tana et al. | |
| 4,825,005 A | 4/1989 | Frey et al. | |
| 5,098,903 A | 3/1992 | Magarian et al. | |
| 5,124,337 A | 6/1992 | Dugar et al. | |
| 5,126,351 A | 6/1992 | Luzzio et al. | |
| 5,244,904 A | 9/1993 | Nagase et al. | |
| 5,280,024 A | 1/1994 | Bolland et al. | |
| 5,354,749 A | 10/1994 | Dressel et al. | |
| 5,407,942 A | 4/1995 | Dressel et al. | |
| 5,409,930 A | 4/1995 | Spada et al. | |
| 5,446,071 A | 8/1995 | Grese | |
| 5,474,994 A | 12/1995 | Leonardi et al. | |
| 5,480,883 A | 1/1996 | Spada et al. | |
| 5,539,119 A | 7/1996 | Nagase et al. | |
| 5,576,322 A | 11/1996 | Takase et al. | |
| 5,595,974 A | 1/1997 | Tomaru | |

(Continued)

FOREIGN PATENT DOCUMENTS

AU         719140 B2    7/1998
CA        2104981 A1    3/1994

(Continued)

OTHER PUBLICATIONS

Abdel-Jalil et al., "Synthesis and Antitumor Activity of 2-Aryl-7-fluoro-6-(4-methyl-1-piperazinyl)-4(3H)-quinazolinones" *Heterocycles* 65(9):2061-2070 (2005).
Abdul-Rahman et al., "Dinuclear molybdenum complexes derived from diphenols: electrochemical interactions and reduced species" *Polyhedron* 16(24):4353-4362 (1997).
Acton et al., "Identification of Scavenger Receptor SR-BI as a High Density Lipoprotein Receptor" *Science* 271:518-520 (1996).

(Continued)

*Primary Examiner* — San-Ming Hui
(74) *Attorney, Agent, or Firm* — Finnegan, Henderson, Farabow, Garrett & Dunner, LLP

(57) ABSTRACT

Disclosed are novel compounds that are useful for regulating the expression of apolipoprotein A-I (ApoA-I), and their use for the treatment and prevention of cardiovascular disease and related disease states, including cholesterol- or lipid-related disorders, such as, for example, atherosclerosis. Also disclosed are pharmaceutical compositions comprising the novel compounds. Formula (I)

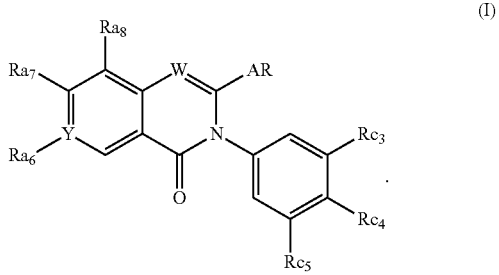

16 Claims, No Drawings

(56) References Cited

U.S. PATENT DOCUMENTS

| | | | |
|---|---|---|---|
| 5,693,652 | A | 12/1997 | Takase et al. |
| 5,707,987 | A | 1/1998 | Nakagawa et al. |
| 5,733,913 | A | 3/1998 | Blankley et al. |
| 5,756,344 | A | 5/1998 | Onda et al. |
| 5,756,544 | A | 5/1998 | Bisgaier et al. |
| 5,756,736 | A | 5/1998 | Arzeno et al. |
| 5,756,763 | A | 5/1998 | Takeuchi et al. |
| 5,763,414 | A | 6/1998 | Bok et al. |
| 5,783,577 | A | 7/1998 | Houghten et al. |
| 5,792,461 | A | 8/1998 | Bok et al. |
| 5,792,902 | A | 8/1998 | Benoit et al. |
| 5,798,344 | A | 8/1998 | Kuroki et al. |
| 5,801,180 | A | 9/1998 | Takase et al. |
| 5,817,674 | A | 10/1998 | Clemence et al. |
| 5,854,264 | A | 12/1998 | Anthony et al. |
| 5,877,208 | A | 3/1999 | Bok et al. |
| 5,922,866 | A | 7/1999 | Miyata et al. |
| 5,965,556 | A | 10/1999 | Takeuchi et al. |
| 6,022,901 | A | 2/2000 | Goodman |
| 6,048,903 | A | 4/2000 | Toppo |
| 6,054,435 | A | 4/2000 | Or et al. |
| 6,133,241 | A | 10/2000 | Bok et al. |
| 6,165,984 | A | 12/2000 | Bok et al. |
| 6,168,776 | B1 | 1/2001 | Klunk et al. |
| 6,239,114 | B1 | 5/2001 | Guthrie et al. |
| 6,291,456 | B1 | 9/2001 | Stein et al. |
| 6,303,629 | B1 | 10/2001 | Kun |
| 6,340,759 | B1 | 1/2002 | Ueno et al. |
| 6,414,037 | B1 | 7/2002 | Pezzuto et al. |
| 6,455,577 | B2 | 9/2002 | Bok et al. |
| 6,479,499 | B1 | 11/2002 | Kuo et al. |
| 6,482,479 | B1 | 11/2002 | Dübal et al. |
| 6,512,161 | B1 | 1/2003 | Rouy et al. |
| 6,541,045 | B1 | 4/2003 | Charters et al. |
| 6,541,522 | B2 | 4/2003 | Inman et al. |
| 6,548,548 | B2 | 4/2003 | Campbell et al. |
| 6,613,772 | B1 | 9/2003 | Schindler et al. |
| 6,635,642 | B1 | 10/2003 | Jackson et al. |
| 6,673,780 | B2 | 1/2004 | Dasseux et al. |
| 6,703,422 | B2 | 3/2004 | Dasseux et al. |
| 7,087,612 | B2 | 8/2006 | Rodriguez Sarmiento et al. |
| 7,173,128 | B2 | 2/2007 | Ravichandran et al. |
| 7,244,776 | B2 | 7/2007 | Ravichandran et al. |
| 7,846,915 | B2 | 12/2010 | Wong et al. |
| 8,053,440 | B2 | 11/2011 | Hansen |
| 8,093,273 | B2 | 1/2012 | Wong et al. |
| 8,114,995 | B2 | 2/2012 | Hansen et al. |
| 8,242,130 | B2 | 8/2012 | Wong et al. |
| 8,242,144 | B2 | 8/2012 | Wong et al. |
| 8,410,109 | B2 | 4/2013 | Wong et al. |
| 2002/0004608 | A1 | 1/2002 | Alig et al. |
| 2002/0025301 | A1 | 2/2002 | Haremza et al. |
| 2002/0091263 | A1 | 7/2002 | Trova |
| 2003/0064967 | A1 | 4/2003 | Luchoomun et al. |
| 2003/0068526 | A1 | 4/2003 | Kamatani et al. |
| 2003/0072964 | A1 | 4/2003 | Kwong et al. |
| 2003/0171429 | A1 | 9/2003 | Chen et al. |
| 2004/0001834 | A1 | 1/2004 | Kim et al. |
| 2004/0033480 | A1 | 2/2004 | Wong |
| 2004/0058903 | A1 | 3/2004 | Takasugi et al. |
| 2004/0097493 | A1 | 5/2004 | Chen et al. |
| 2004/0198750 | A1 | 10/2004 | Green et al. |
| 2004/0235888 | A1 | 11/2004 | Yamamori et al. |
| 2004/0242615 | A1 | 12/2004 | Yamamori et al. |
| 2004/0248950 | A1 | 12/2004 | Ishizuka et al. |
| 2005/0043300 | A1 | 2/2005 | Middleton et al. |
| 2005/0080021 | A1 | 4/2005 | Tucker et al. |
| 2005/0080024 | A1 | 4/2005 | Tucker et al. |
| 2005/0261319 | A1 | 11/2005 | Deuschle et al. |
| 2006/0116364 | A1 | 6/2006 | Hamaoka et al. |
| 2007/0099826 | A1 | 5/2007 | Wong et al. |
| 2007/0185160 | A1 | 8/2007 | Hattori et al. |
| 2007/0218155 | A1 | 9/2007 | Kuhrts |
| 2008/0275069 | A1 | 11/2008 | Mizutani et al. |
| 2010/0093636 | A1 | 4/2010 | Schultz et al. |
| 2011/0201608 | A1 | 8/2011 | Hoffmann et al. |
| 2012/0015905 | A1 | 1/2012 | Hansen |
| 2012/0040954 | A1 | 2/2012 | Hansen |
| 2012/0059002 | A1 | 3/2012 | Hansen et al. |
| 2013/0108672 | A1 | 5/2013 | Shenoy |
| 2014/0107369 | A1 | 4/2014 | Lozanov et al. |

FOREIGN PATENT DOCUMENTS

| | | |
|---|---|---|
| CA | 2345406 A1 | 4/2000 |
| CA | 2815127 A1 | 4/2012 |
| CN | 1067070 C | 6/2001 |
| CN | 1430599 A | 7/2003 |
| DE | 637259 | 10/1936 |
| DE | 652772 | 11/1937 |
| DE | 35 32 279 A1 | 3/1987 |
| DE | 36 01 417 A1 | 7/1987 |
| DE | 42 15 588 A1 | 11/1993 |
| DE | 196 51 099 A1 | 6/1998 |
| DE | 197 56 388 A1 | 6/1999 |
| DE | 199 34 799 A1 | 2/2001 |
| EP | 0 210 342 A2 | 2/1987 |
| EP | 0 258 190 A2 | 3/1988 |
| EP | 0 182 213 B1 | 9/1990 |
| EP | 0 407 217 A1 | 1/1991 |
| EP | 0 410 834 A1 | 1/1991 |
| EP | 0 488 602 A1 | 6/1992 |
| EP | 0 272 455 B1 | 2/1993 |
| EP | 0 375 404 B1 | 2/1994 |
| EP | 0 333 175 B1 | 6/1994 |
| EP | 0 343 499 B1 | 7/1994 |
| EP | 0 409 413 B1 | 8/1994 |
| EP | 0 420 511 B1 | 8/1994 |
| EP | 0 633 022 A2 | 1/1995 |
| EP | 0 569 795 B1 | 4/1995 |
| EP | 0 330 108 B1 | 12/1995 |
| EP | 0 747 051 A2 | 12/1996 |
| EP | 0 564 350 B1 | 5/1997 |
| EP | 0 643 119 B1 | 4/2000 |
| EP | 1 125 908 A1 | 8/2001 |
| EP | 0 498 723 B1 | 9/2001 |
| EP | 0 607 439 B1 | 1/2002 |
| EP | 0 776 893 B1 | 2/2002 |
| EP | 1 195 378 A1 | 4/2002 |
| EP | 1 277 738 A1 | 1/2003 |
| EP | 1 398 032 A1 | 3/2004 |
| EP | 1 418 164 A1 | 5/2004 |
| EP | 1 426 046 A1 | 6/2004 |
| EP | 1 477 481 A1 | 11/2004 |
| EP | 1 637 523 A1 | 3/2006 |
| EP | 1 757 594 A1 | 2/2007 |
| EP | 1 944 301 A1 | 7/2008 |
| EP | 2 005 941 A2 | 12/2008 |
| FR | 803201 | 9/1936 |
| FR | 803619 | 10/1936 |
| FR | 2 244 492 | 4/1975 |
| FR | 2 244 493 | 4/1975 |
| GB | 472489 | 9/1937 |
| GB | 728767 | 4/1955 |
| GB | 1175808 | 12/1969 |
| GB | 1179019 | 1/1970 |
| GB | 2 292 149 A | 2/1996 |
| IE | 902587 A1 | 7/1990 |
| JP | 6-80656 A | 3/1994 |
| JP | 7-41442 A | 2/1995 |
| JP | 7-61942 A | 3/1995 |
| JP | 7-118241 A | 5/1995 |
| JP | 7-179380 A | 7/1995 |
| JP | 7-233109 A | 9/1995 |
| JP | 7-247289 A | 9/1995 |
| JP | 10-287678 A | 10/1998 |
| JP | 2004-511502 A | 4/2001 |
| JP | 2001-131151 A | 5/2001 |
| JP | 2001-139550 A | 5/2001 |
| JP | 2001-335476 A | 12/2001 |
| JP | 2002-249483 A | 9/2002 |
| JP | 2004-203751 A | 7/2004 |
| JP | 2004-307440 A | 11/2004 |
| KR | 10-0707532 | 8/2005 |

(56) References Cited

FOREIGN PATENT DOCUMENTS

| WO | WO 91/18901 A1 | 12/1991 |
|---|---|---|
| WO | WO 92/09374 A1 | 6/1992 |
| WO | WO 92/18123 A2 | 10/1992 |
| WO | WO 92/20642 A1 | 11/1992 |
| WO | WO 92/21661 A1 | 12/1992 |
| WO | WO 93/07124 A1 | 4/1993 |
| WO | WO 93/08174 A1 | 4/1993 |
| WO | WO 94/14763 A1 | 7/1994 |
| WO | WO 95/03277 A1 | 2/1995 |
| WO | WO 95/23150 A1 | 8/1995 |
| WO | WO 96/15128 A2 | 5/1996 |
| WO | WO 96/31206 A2 | 10/1996 |
| WO | WO 97/10221 A1 | 3/1997 |
| WO | WO 97/15308 A1 | 5/1997 |
| WO | WO 97/28118 A1 | 8/1997 |
| WO | WO 97/28132 A1 | 8/1997 |
| WO | WO 97/28134 A1 | 8/1997 |
| WO | WO 97/29106 A1 | 8/1997 |
| WO | WO 97/48694 A1 | 12/1997 |
| WO | WO 98/11438 A1 | 3/1998 |
| WO | WO 98/26127 A1 | 6/1998 |
| WO | WO 98/30530 A1 | 7/1998 |
| WO | WO 98/50370 A1 | 11/1998 |
| WO | WO 98/51307 A1 | 11/1998 |
| WO | WO 98/51308 A1 | 11/1998 |
| WO | WO 98/55124 A1 | 12/1998 |
| WO | WO 99/00116 A2 | 1/1999 |
| WO | WO 99/11634 A1 | 3/1999 |
| WO | WO 99/18077 A1 | 4/1999 |
| WO | WO 99/29667 A1 | 6/1999 |
| WO | WO 00/17184 A1 | 3/2000 |
| WO | WO 00/23075 A1 | 4/2000 |
| WO | WO 00/35865 A2 | 6/2000 |
| WO | WO 00/44362 A2 | 8/2000 |
| WO | WO 00/55168 A1 | 9/2000 |
| WO | WO 00/64888 A1 | 11/2000 |
| WO | WO 01/00554 A2 | 1/2001 |
| WO | WO 01/60775 A1 | 8/2001 |
| WO | WO 01/82916 A2 | 11/2001 |
| WO | WO 01/83456 A1 | 11/2001 |
| WO | WO 01/90051 A1 | 11/2001 |
| WO | WO 02/32377 A2 | 4/2002 |
| WO | WO 02/44189 A1 | 6/2002 |
| WO | WO 02/074307 A1 | 9/2002 |
| WO | WO 02/087556 A1 | 11/2002 |
| WO | WO 02/096426 A1 | 12/2002 |
| WO | WO 03/007959 A1 | 1/2003 |
| WO | WO 03/016292 A1 | 2/2003 |
| WO | WO 03/018008 A1 | 3/2003 |
| WO | WO 03/040256 A2 | 5/2003 |
| WO | WO 03/040257 A1 | 5/2003 |
| WO | WO 03/070236 A2 | 8/2003 |
| WO | WO 03/099274 A1 | 12/2003 |
| WO | WO 03/106435 A1 | 12/2003 |
| WO | WO 2004/017920 A2 | 3/2004 |
| WO | WO 2004/019933 A1 | 3/2004 |
| WO | WO 2004/032846 A2 | 4/2004 |
| WO | WO 2004/037176 A2 | 5/2004 |
| WO | WO 2004/039795 A2 | 5/2004 |
| WO | WO 2004/047755 A2 | 6/2004 |
| WO | WO 2004/056355 A1 | 7/2004 |
| WO | WO 2004/058717 A1 | 7/2004 |
| WO | WO 2004/065392 A1 | 8/2004 |
| WO | WO 2004/072042 A2 | 8/2004 |
| WO | WO 2004/092196 A2 | 10/2004 |
| WO | WO 2004/094452 A2 | 11/2004 |
| WO | WO 2004/108139 A2 | 12/2004 |
| WO | WO 2004/112710 A2 | 12/2004 |
| WO | WO 2005/034960 A1 | 4/2005 |
| WO | WO 2005/042712 A2 | 5/2005 |
| WO | WO 2005/065183 A2 | 7/2005 |
| WO | WO 2005/066162 A1 | 7/2005 |
| WO | WO 2005/075431 A1 | 8/2005 |
| WO | WO 2005/115993 A1 | 12/2005 |
| WO | WO 2006/012577 A2 | 2/2006 |
| WO | WO 2006/071095 A1 | 7/2006 |
| WO | WO 2006/105081 A2 | 10/2006 |
| WO | WO 2007/071055 A1 | 6/2007 |
| WO | WO 2008/092231 A1 | 8/2008 |
| WO | WO 2008/152471 A1 | 12/2008 |
| WO | WO 2010/015520 A1 | 2/2010 |
| WO | WO 2010/100178 A1 | 9/2010 |

OTHER PUBLICATIONS

Asztalos, "High-Density Lipoprotein Metabolism and Progression of Atherosclerosis: New Insights from the HDL Atherosclerosis Treatment Study" *Curr. Opin. Cardiol.* 19:385-391 (2004).

Baba et al., "Continuous intake of polyphenolic compounds containing cocoa powder reduces LDL oxidative susceptibility and has beneficial effects on plasma HDL-cholesterol concentrations in humans" *Am. J. Clin. Nutr.* 85:709-717 (2007).

Badimon et al., "Role of High Density Lipoproteins in the Regression of Atherosclerosis" *Circulation* 86(Suppl. III):86-94 (1992).

Barrans et al., "Pre-β HDL: Structure and Metabolism" *Biochim. Biophys. Acta* 1300:73-85 (1996).

Barter et al., "Antiinflammatory Properties of HDL" *Circ. Res.* 95:764-772 (2004).

Barter et al., "High Density Lipoproteins and Coronary Heart Disease" *Atherosclerosis* 121:1-12 (1996).

Bayly et al., "Electronic and magnetic metal-metal interactions in dinuclear oxomolybdenum(V) complexes across bis-phenolate bridgina ligands with different spacers between the phenolate termini: ligand-centered vs. metal-centered redox activity" *J. Chem. Soc., Dalton Transactions* 9:1401-1414 (2001).

Bertele et al., "Platelet Thromboxane Synthetase Inhibitors with Low Doses of Aspirin: Possible Resolution of the 'Aspirin Dilemma'" *Science* 220:517-519 (1983).

Beugelmans et al., "One-pot Synthesis of 1-Oxo-1,2-Dihydroisoquinolines (Isocarbostyrils) Via $S_{RN}1$ (Ar) Reactions" *Synthesis* 9:729-731 (1981).

Bhilare et al., "Ionic-Liquid-Influenced Expeditious and Stereoselective Synthesis of Olefins" *Synthetic Communications* 37(18):3111-3117 (2007).

Bisagni et al., "A Convenient Way to Dibenzo[c,h]-1,5-Naphthyridines (11-Aza-Benzo[c]phenanthridines)" *Tetrahedron* 52:10427-10440 (1996).

Bisgaier et al., "A Novel Compound that Elevates High Density Lipoprotein and Activates the Peroxisome Proliferator Activated Receptor" *J. Lipid Res.* 39:17-30 (1998).

Boyce et al., "The Acylation and Alkylation of o-Tolunitrile. A New Route to 3-Substituted Isocarbostyrils" *J. Org. Chem.* 31:3807-3809 (1966).

Bradsher et al., "A New Isoquinoline Synthesis Via ORTHO-Substituted Benzylamines" *Tetrahedron Lett.* 31:3149-3150 (1972).

Bradsher et al,, "α-Acyl-o-Tolunitriles as Intermediates in the Preparation of 3-Substituted Isoquinolines and 1-Amino-2-benzopyrylium Derivatives" *J. Org. Chem,* 43:3817-3820 (1978).

Buhle et al., "Trivalent Carbon. II. Unsymmetrical Hexaaryldimethylperoxides" *J. Am. Chem. Soc.* 65:584-586 (1943).

CAPLUS Accession No. 1991:449453, Liu et al. "Synthesis of 2-aryl-9-bromo-4-oxo-4H-pyrano[3,2-c] quinolines" [online]. Retrieved from STN on Jan. 31, 2011. Also published in: *Youji Huaxue* 11(2)101-195(1991).

CAPLUS Accession No. 2003:554477, Qin et al., "Synthesis and fungicidal activity of novel diazaflavanones" [online]. Retrieved from STN on Jan. 31, 2011. Also published in: *Nongyaoxue Xuebao* 4(4):28-32 (2002).

CAPLUS Accession No. 2004:11346, Hu et al., "Synthesis and fungicidal activity of flavanone derivatives containing isopentenyl group" [online]. Retrieved from STN on Jan. 31, 2011. Also published in: *Yingyong Huaxue* 20(12):1161-1165 (2003).

CAPLUS Accession No. 2005:46491, Qin et al., "Synthesis and fungicidal activity of 5,7-dihydroxydiazinflavanones" [online]. Retrieved from STN on Jan. 31, 2011. Also published in: *Huazhong Shifan Daxue Xuebao Zirankexueban*38(3):323-325 (2004).

(56) References Cited

OTHER PUBLICATIONS

Chakrabarty et al., "Induction of apoptosis in human cancer cell lines by diospyrin, a plant-derived bisnaphthoquinonoid, and its synthetic derivatives" *Cancer Letters* 188(1-2):85-93 (2002).

Chartier et al., "Synthése de diazaflavones" *Bull. Soc. Chim. Fr.* 11-12(Pt. 2):1916-1918 (1976). English abstract on p. 1916.

Cherubini et al., "Role of Antioxidants in Atherosclerosis: Epidemiological and Clinical Update" *Curr. Pharm. Des.* 11:2017-2032 (2005).

Cho et al., "Molecular Modeling of 3-Arylisoquinoline Antitumor Agents Active Against A-549. A Comparative Molecular Field Analysis Study" *Bioorg. Med. Chem.* 10:2953-2961 (2002).

Cho et al., "Synthesis and Antitumor Activity of 3-Arylisoquinoline Derivatives" *Arch. Pharm. Res.* 20:264-268 (1997).

Cho et al., "Synthesis and Biological Evaluation of 3-Arylisoquinolines As Antitumor Agents" *Bioorg. Med. Chem. Lett.* 8:41-46 (1998).

Cho et al., "Synthesis and Comparative Molecular Field Analysis (CoMFA) of Antitumor 3-Arylisoquinoline Derivatives" *Bioorg. Med. Chem.* 6(12):2449-2458 (1998).

Chyu et al., "Differential Effects of Green Tea-Derived Catechin on Developing Versus Established Atherosclerosis in Apolipoprotein E-Null Mice" *Circulation* 109:2448-2453 (2004).

Clarkson et al., "Inhibition of Postmenopausal Atherosclerosis Progression: A Comparison of the Effects of Conjugated Equine Estrogens and Soy Phytoestrogens" *J. Clin. Endocrinol. Metab.* 86(1):41-47 (2001).

Clauson-Kaas et al., "Reactions of 3,4-dihydor-2H-pyrrido[3,2-b]-1,4-oxazines" *Acta Chemica Scandinavica* 25(8):3135-3143 (1971). Retrieved from STN, file HCAPLUS, Accession No. 1972:34186 (Abstract).

Connolly et al., "Synthesis of quinazolinones and quinazolines" *Tetrahedron* 61(43):10153-10202 (2005).

Cooper et al., "Wine polyphenols and promotion of cardiac health" *Nutr. Res. Rev.* 17:111-129 (2004).

Cramer et al., "New Syntheses of Aryl Fluorides and Aryl Fluorosulfonates from Oxyflourides of Sulfur" *J. Org. Chem.* 26:4164-4165 (1961).

Dai et al., "Synthesis of 3,4-Disubstituted Isoquinolines via Palladium-Catalyzed Cross-Coupling of 2-(1-alkynyl)benzaldimines and Organic Halides" *J. Org. Chem.* 68:920-928 (2003).

Dai et al., "Synthesis of 3-Substituted 4-Aroylisoquinolines via Pd-Catalyzed Carbonylative Cyclization of 2-(1-Alkynyl)benzaldimines" *J. Org. Chem.* 67:7042-7047 (2002).

Dansky et al., "High-Density Lipoprotein and Plaque Regression. The Good Cholesterol Gets Even Better" *Circulation* 100:1762-1763 (1999).

Decossin et al., "Subclasses of LpA-I In Coronary Artery Disease: Distribution and Cholesterol Efflux Ability" *Eur. J. Clin. Invest.* 27:299-307 (1997).

Devitt et al., "Synthesis of Heterocyclic-Substituted Chromones and Chalcones" *J. Org. Chem.* 26:4941-4944 (1961).

Edwards et al., "Inhibition of myeloperoxidase release from rat polymorphonuclear leukocytes by a series of azachalcone derivatives" *J. Med. Chem.* 37(25):4357-4362 (1994).

Eiden et al., "1,2-Bisbenzopyranyl-ethene" *Archiv. der Pharmazie* 313(2):120-128 (1980) (German).

Esterbauer et al., "Continuous Monitoring of In Vitro Oxidation of Human Low Density Lipoprotein" *Free Rad. Res. Comms.* 6:67-75 (1989).

Ferreira et al., "Diversity of Structure and Function in Oligomeric Flavanoids" *Tetrahedron* 48:1743-1803 (1992).

Fielding et al., "Molecular Physiology of Reverse Cholesterol Transport" *J. Lipid Res.* 36:211-228 (1995).

Fieser, L.F., "The potentials of some unstable oxidation-reduction systems" *J. Am. Chem. Soc.* 52:4915-4940 (1930).

Fisher Center for Alzheimer's Research Foundation, "Alzheimer's Disease: 'Good' Cholesterol May Help Keep Alzheimer's at Bay" The Ninth International Conference on Alzheimer's Disease and Related Disorders, Philadelphia, PA, Jul. 22, 2004. Retrieved from the Internet: http://www.alzinfo.org/newsarticle/templates/archivenews.template.asp?articleid=156&zoneid=7 on Jul. 28, 2010 (3 pages).

Flammang et al., "2,3-Benzodiazepines: 2-Aminoisoquinolinones From Ring Contraction of 1-oxo-2,3-Benzodiazepines" *C R Acad. Sci. Paris, Series C* 290:361-363 (1980) (French).

Fokialakis et al., "A New Class of Phytoestrogens: Evaluation of the Estrogenic Activity of Deoxybenzoins" *Chem. Biol.* 11:397-406 (2004).

Gaziano et al., "Relation Between Systemic Hypertension and Blood Lipids on the Risk of Myocardial Infarction" *Am. J. Cardiol.* 84(7):768-773 (1999).

Gerritsen et al., "Flavenoids inhibit cytokine-induced endothelial cell adhesion protein gene expression" *Am. J. Pathol.* 147(2):278-292 (1995).

Gidez et al., "Separation and Quantitation of Subclasses of Human Plasma High Density Lipoproteins by a Simple Precipitation Procedure" *J. Lipid Res.* 23:1206-1223 (1982).

Gordon et al., "High Density Lipoprotein As a Protective Factor Against Coronary Heart Disease" *Am. J. Med.* 62(5):707-714 (1977).

Grundy et al., "Definition of Metabolic Syndrome. Report of the National Heart, Lung and Blood Institute/American Heart Association Conference on Scientific Issues Related to Definition" *Circulation* 109:433-438 (2004).

Gugler et al., "Disposition of Quercetin in Man after Single Oral and Intravenous Doses" *Eur. J. Clin. Pharmacol.* 9:229-234 (1975).

Guillory, J.K., "Generation of Polymorphs, Hydrates, Solvates, and Amorphous Solids" Brittain, Harry G. (ed.) *Polymorphism in Pharmaceutical Solids*, vol. 95. Marcel Dekker, Inc., New York; pp. 202-208 (1999).

Hakamata et al., "Differential effects of an acyl-coenzyme A: cholesterol acyltransferase inhibitor on HDL-induced cholesterol efflux from rat macrophage foam cells" *FEBS Letters* 363:29-32 (1995).

Haneke, "*trans*-Resveratrol, [501-36-0], Review of Toxicological Literature" Nat. Inst. Environ. Health Sciences Contract No. N01-ES-65402 (Mar. 2002).

Hazra et al., "New diospyrin derivatives with improved tumour inhibitory activity towards Ehrlich ascites carcinoma" *Medical Science Research* 22(5):351-353 (1994).

Hazra et al., "Synthesis of an antitumor derivative of diospyrin" *IRCS Medical Science* 14(1):35-36 (1986).

Heeg et al., "Plasma Levels of Probucol in Man after Single and Repeated Oral Doses" *La Nouvelle Presse Medicale* 9:2990-2994 (1980).

Hemingway et al., "A gas-liquid chromatographic examination of stilbene derivatives" *J. Chromatog.* 50(3):391-399 (1970).

Hertog et al., "Dietary Antioxidant Flavonoids and Risk of Coronary Heart Disease: the Zutphen Elderly Study" *Lancet* 342:1007-1011 (1993).

Hidaka et al., "Affinity Purification of the Hepatic High-Density Lipoprotein Receptor Identifies Two Acidic Glycoproteins and Enables Further Characterization of Their Binding Properties" *Biochem. J.* 284:161-167 (1992).

Hirano et al., "Genetic Cholesteryl Ester Transfer Protein Deficiency Is Extremely Frequent in the Omagari Area of Japan. Marked Hyperalphalipoproteinemia Caused by CETP Gene Mutation Is Not Associated With Longevity" *Arterioscler Thromb. Vasc. Biol.* 17:1053-1059 (1997).

Hisano et al., "Studies on Organosulfur Compounds. XII. Syntheses and Pharmacological Activities of 2-Heterocyclic Substituted 4(3H)-Quinazolines" *Chem. Pharm. Bull.* 23(9):1910-1916 (1975).

Huang et al., "Synthesis of Isoguinolines by Palladium-Catalyzed Cyclization, Followed by a Heck Reaction" *Tetrahedron Lett.* 43:3557-3560 (2002).

Hwang et al., "Syntergistic inhibition of LDL oxidation by phytoestrogens and ascorbic acid" *Free Radical Biology and Medicine* 29(1):79-89 (Jul. 1, 2000).

International Search Report and Written Opinion issued in International Application No. PCT/CA2004/001818: Date of Mailing: Feb. 28, 2005.

International Search Report and Written Opinion issued in International Application No. PCT/CA2007/000146; Date of Mailing: Oct. 29, 2007.

(56) References Cited

OTHER PUBLICATIONS

International Search Report and Written Opinion issued in International Application No. PCT/IB2010/000159; Date of Mailing: Aug. 5, 2010.
International Search Report and Written Opinion issued in International Application No. PCT/IB2010/000826; Date of Mailing: Oct. 12, 2010.
International Search Report and Written Opinion issued in International Application No. PCT/IB2010/031870; Date of Mailing: Jul. 1, 2010.
International Search Report and Written Opinion issued in International Application No. PCT/IB2012/002721; Date of Mailing: Mar. 14, 2013.
International Search Report and Written Opinion issued in International Application No. PCT/US2005/037719; Date of Mailing: Mar. 9, 2007.
International Search Report and Written Opinion issued in International Application No. PCT/US2005/038048; Date of Mailing: Mar. 7, 2007.
International Search Report and Written Opinion issued in International Application No. PCT/US2006/029827; Date of Mailing; Apr. 16, 2007.
International Search Report and Written Opinion issued in International Application No. PCT/US2009/048457; Date of Mailing: Oct. 16, 2009.
Ishibashi et al., "Hypercholesterolemia in Low Density Lipoprotein Receptor Knockout Mice and its Reversal by Adenovirus-Mediated Gene Delivery" *J. Clin. Invest.* 92:883-893 (1993).
Ishibashi et al., "Massive Xanthomatosis and Atherosclerosis in Cholesterol-Fed Low Density Lipoprotein Receptor-Negative Mice" *J. Clin. Invest.* 93:1885-1893 (1994).
Japanese Office Action issued in Japanese Patent Application No. 2008-524272, mailed Jul. 24, 2012, with English translation.
Jayatilake et al., "Kinase Inhibitors From *Polygonum cuspidatum*" *J. Nat. Prod.* 56:1805-1810 (1993).
Jensen et al., "Serum Lipids and Anthropometric Factors Related to the Prevalence of Intermittent Claudication" *Eur. J. Vasc. Endovasc. Surg.* 30:582-587 (2005).
Jeong et al., "Hypocholesterolernic activity of hesperetin derivatives" *Bioorg. Med. Chem. Lett.* 13:2663-2665 (2003).
Jin et al., "Antiplatelet and antithrombotic activities of CP201, a newly synthesized 1,4-naphthoquinone derivative" *Vasc. Pharmacol.* 41(1):35-41 (2004).
Kalusa et al., "An efficient synthesis of 2,3-diaryl (3H)-quinazolin-4-ones via imidoyl chlorides" *Tetrahedron Letters* 49(41):5840-5842 (2008).
Kawamatsu et al., "2-Amino-4-Phenylthiazole Derivatives As Anti-Atherogenic Agents" *Eur. J. Med. Chem.—Chimica Therapeutica* 16(4):355-362 (1981).
Kilbourne et al., "Involvement of Early Growth Response Factor Egr-1 in Apolipoprotein Al Gene Transcription" *J. Biol. Chem.* 270:7004-7010 (1995).
Kim et al., "Hytpothetical Drug Binding Receptor Site Analysis Using CoMFA Method for 3-Arylisoquinolines Active Against SK-OV-3 Tumor Cell Line" *Yakhak Hoechi* 46(4):219-225 (2002).
Koudinov et al., "Alzheimer's amyloid beta and lipid metabolism: a missing link?" *FASEB J.* 12:1097-1099 (1998).
Kublak et al., "The preparation of the aza-spirobicyclic system of discorhabdin C via an intramolecular phenolate alkylation" *Tetrahedron Lett.* 31(27):3845-3848 (1990).
Kulkarni et al., "Qunatification of $HDL_2$ and $HDL_3$ Cholesterol by the Vertical Auto Profile-II (VAP-II) Methodology" *J. Lipid Res.* 38:2353-2364 (1997).
Kurata et al., "A Candidate High Density Lipoprotein (HDL) Receptor, $HB_2$, with Possible Multiple Functions Shows Sequence Homology with Adhesion Molecules" *J. Atheroscler. Thromb.* 4:112-117 (1998).
Kurowska et al., "Essential Amino Acids in Relation to Hypercholesterolemia Induced in Rabbits by Dietary Casein" *J. Nutr.* 120:831-836 (1990).

Kuzuya et al., "Probucol Prevents Oxidative Injury to Endothelial Cells" *J. Lipid Res.* 32:197-204 (1991).
Laarhoven et al., "Syntheses, infrared spectra and molecular refractions of some sterically hindered *p,p'*-dimethoxystilbenes. Influence of non-planarity in styrene and stilbene derivatives IV" *Recueil des Travaux Chimiques des Pays-Bas* 80:775-791 (1961).
Lagrost et al., "Opposite Effects of Cholesteryl Ester Transfer Protein and Phospholipid Transfer Protein on the Size Distribution of Plasma High Density Lipoproteins" *J. Biol. Chem.* 271:19058-19065 (1996).
Lamon-Fava, "Genistein activates apolipoprotein A-I gene expression in the human hepatoma cell line Hep G2" *J. Nutrition* 130:2489-2492 (2000).
Landshulz et al., "Regulation of Scavenger Receptor, Class B, Type I, a High Density Lipoprotein Receptor, in Liver and Steroidogenic Tissues of the Rat" *J. Clin. Invest.* 98:984-995 (1996).
Letan, "The Relation of Structure to Antioxidant Activity of Quercetin and some of Its Derivatives. I. Primary Activity" *J. Food Sci.* 13(4):518-523 (1966).
Lin et al., "Chemoprevention of Cancer and Cardiovascular Disease by Resveratrol" *Proc. Natl. Sci. Counc. ROC (B)* 23:99-106 (1999).
Lin et al., "Potential bioreductive alkylating agents. 7. Antitumor effects of phenyl-substituted 2-chloromethyl-3-phenyl-1,4-naphthoquinones" *J. Med. Chem.* 19(11):1336-1338 (1976).
Lin et al., "Solvent Effects on Aza-Anionic Cycloaromatization of 2-(2-Substituted-Ethynyl)Benzonitriles" *J. Chinese Chem. Soc.* 48:211-214 (2001).
Lin et al "The Role of Absorption, Distribution, Metabolism, Excretion and Toxicity in Drug Recovery" *Curr. Top. Med. Chem.* 3:1125-1154 (2003).
Linnell et al. "Isomers of stilbestrol. II." *Q. J. Pharm. Pharmacol.* 15:384-388 (1942).
Lopez et al., "The Synthesis of Substituted 2-Aryl-4(3H)-quinazolinones using $NaHSO_3$/DMA. Steric Effect Upon the Cyclisation-Dehydrogenation Step" *J. Chem. Research (S),* pp. 258-259 (2000).
Maher et al., "Lipoprotein (a) and coronary heart disease" *Curr. Opin. Lipidol.* 6:229-235 (1995).
Mahto et al., "Synthesis of 3-Aryl-7-Hydroxy Isochromenes" *Asian J. Chem.* 11(2):431-435 (1999).
Manach et al., "Polyphenols and prevention of cardiovascular diseases" *Curr. Opin. Lipidol.* 16:77-84 (2005).
Marks, F., "Epidermal Growth Control Mechanisms, Hyperplasia, and Tumor Promotion in the Skin" *Cancer Res.* 36:2636-2343 (1976).
Martin et al., "Modified Flavinoids As Strong Photoprotecting UV-Absorbers and Antioxidants" *Strategies for Safe Food*, Eklund, T. et al. (Eds.), vol. 1, pp. 288-291 (2003).
McKee et al., "Some Basically Substituted Quinazolines" *J. Am. Chem. Soc.* 68(10):1902-1903 (1946).
Meckes et al. "The effects of chrysin and pinostrobin, 2 flavonoids isolated from *Teloxys graveolens* leaves, on isolated guinea-pig ileum" *Phytomedicine* 5(6):459-463 (1998).
Melani et al., "Tricyclic heterocyclic systems: pyrazolo[5',4':4,5]-and pyrazolo-[3',4':4,5]pyrano[2,3-B]pyridine derivatives" *J. Heterocyclic Chem.* 25:1367-1371 (1988).
Middleton et al., "Quercetin inhibits lipopolysaccharide-induced expression of endothelial cell intracellular adhesion molecule-1" *Int. Arch. Allergy Immunol.* 107:435-436 (1995).
Moffett, "Azacoumarins" *J. Org. Chem.* 35(11):3596-3600 (1970).
Mondal et al., "Two-Stage Chemical Oncogenesis in Cultures of C3H/10T1/2 Cells" *Cancer Res.* 36:2254-2260 (1976).
Nicholls et al., "Efficacy and Safety of a Novel Oral Inducer of Apolipoprotein A-I Synthesis in Statin-Treated Patients with Stable Coronary Artery Disease" *J. Am. Coll. Cardiol.* 57(9):1111-1119 (2011).
Nigam et al., "Synthesis and Pharmacological Screening of Some New 2-(Phenyl/Chloromethyl)-3-[4 (N, N-Disubstituted Aminocarbonyl) Phenyl]-8-Substituted-4 (3H)-Quinazolones" *Indian Drugs* 27(4):238-243 (1990).
Nissen et al., "Effect of Recombinant ApoA-I Milano on Coronary Atherosclerosis in Patients with Acute Coronary Syndroms: A Randomized Controlled Trial" *JAMA* 290(17):2292-2300 (2003).

(56) References Cited

OTHER PUBLICATIONS

Nourooz-Zadeh, "Ferrous Ion Oxidation in Presence of Xylenol Orange for Detection of Lipid Hydroperoxides in Plasma" *Methods Enzymol.* 300:58-62 (1999).

Ohtomo et al., "Comparative activities of daidzein metabolites, equol and O-desmethylangolensin, on bone mineral density and lipid metabolism in ovariectomixed mice and in osteoclast cell cultures" *Eur. J. Nutr.* 47(5):273-279 (2008).

Ordovas, J.M., "Gene-diet interaction and plasma lipid responses to dietary intervention" *Biochem. Soc. Trans.* 30(2):68-73 (2002).

Parra et al., "A Case-Control Study of Lipoprotein Particles in Two Populations at Contrasting Risk for Coronary Heart Disease" *Arterioscler Thromb.* 12:701-707 (1992).

Patani et al., "Bioisosterism: A Rational Approach in Drug Design" *Chem. Rev.* 96(8):3147-3176 (1996).

Pearson et al., "The *ortho* Bromination of Phenols" *J. Org. Chem.* 32:2358-2360 (1967).

Pettit et al., "Antineoplastic Agents. 465. Structural Modification of Resveratrol: Sodium Resverastatin Phosphate" *J. Med. Chem.* 45:2534-2542 (2002).

Plump et al., "Human apolipoprotein A-I gene expression increases high density lipoprotein and suppresses atherosclerosis in the apolipoprotein E-deficient mouse" *Proc. Natl. Acad. Sci. USA* 91:9607-9611 (1994).

Quinones et al., "The *egr-1* gene is induced by DNA-damaging agents and non-genotoxic drugs in both normal and neoplastic human cells" *Life Sciences* 72(26):2975-2992 (2003).

Ragione et al., "Antioxidants induce different phenotypes by a distinct modulation of signal transduction" *FEBS Letters* 523:289-294 (2002).

Ragione et al., "p21$^{CIP}$1 Gene Expression Is Modulated by Egr1: A Novel Regulatory Mechanism Involved in the Resveratrol Antiproliferative Effect" *J. Biol. Chem.* 278:23360-23368 (2003).

Rajakumar et al., "TiCl$_4$, Dioxane—A facile and efficient system for de-O-benzylation, de-O-allylation, and de-O-xylylation of phenolic ethers" *Synthetic Communications* 33(22):3891-3896 (2003).

Raun et al., "Apolipoprotein A-I possesses an anti-obesity effect associated with increase of energy expenditure and upregulation of UCP1 in brown fat" *J. Cell. Mol. Med.* (2010). "Postprint"; 10.1111/j.1582.4934.2010.01045.x.

Rice-Evans, "Flavonoids and Isoflavones: Absorption, Metabolism, and Bioactivity" *Free Radical Biol. Med.* 36:827-828 (2004).

Richtzenhain, H. "Estrogenic stilbene and diphenylethane derivatives. II." *Chemische Berichte* 82:405-407 (1949) (German).

Rigotti et al., "Regulation by Adrenocorticotropic Hormone of the in Vivo Expression of Scavenger Receptor Class B Type I (SR-BI), a High Density Lipoprotein Receptor, in Steroidogenic Cells of the Murine Adrenal Gland" *J. Biol. Chem.* 271:33545-33549 (1996).

Rimando et al., "Pterostilbene, a New Agonist for the Peroxisome Proliferator-Activated Receptor α-Isoform, Lowers Plasma Lipoproteins and Cholesterol in Hypocholesterolemic Hamsters" *Journal of Agricultural and Food Chemistry* 53(9):3404-3407 (2005).

Rodriguez et al., "Novel Effects of the Acyl-Coenzyme A: Cholesterol Acyltransferase Inhibitor 58-035 on Foam Cell Development in Primary Human Monocyte-Derived Macrophages" *Arterioscler. Thromb. Vasc. Biol.* 19:2199-2206 (1999).

Rose et al., "Oxygen Heterocycles. XIII. From 3-Arylisocoumarins to 3-Arylisoquinolines and 4-Aryl-5*H*-2,3-Benzodiazepines" *J. Chem. Soc. [Section] C: Organic* 17:2205-2208 (1968).

Rubin et al., "Expression of Human Apolipoprotein A-I in Transgenic Mice Results in Reduced Plasma Levels of Murine Apolipoprotein A-I and the Appearance of Two New High Density Lipoprotein Size Subclasses" *Proc. Natl. Acad. Sci. USA* 88:434-438 (1991).

Rubin et al., "Inhibition of Early Atherogenesis in Transgenic Mice by Human Apolipoprotein AI" *Nature* 353:265-267 (1991).

Rubins et al., "Reduction in Stroke with Gemfibrozil in Men with Coronary Heart Disease and Low HDL Cholesterol. The Veterens Affairs HDL Intervention Trial (VA-HIT)" *Circulation* 103:2828-2833 (2001).

Sarkhel et al., "3-Arylisocoumarin: Synthesis of 3-(4-methoxyphenyl)-isocoumarim" *J. Indian Chem. Soc.* 53:915-916 (1976).

Schiess et al., "Thermolytic Ring Opening of Acyloxybenzocyclobutenes: An Efficient Route to 3-Substituted Isoquinolines" *Tetrahedron Lett.* 26:3959-3962 (1985).

Schmutz et al., "Synthese von basisch substituierten Chromonen" *Helv. Chim. Acta* 36:620-626 (1953) (German).

Schork, N.J., "Genetics of Complex Disease. Approaches, Problems, and Solutions" *Am. J. Respir. Crit. Care Med.* 156(4):S103-109 (Oct. 1997).

Schultz et al, "Role of stilbenes in the natural durability of wood: fungicidal structure-activity relationships" *Phytochemistry* 29(5):1501-1507 (1990).

Shah et al., "Effects of Recombinant Apolipoprotein A-1$_{Milano}$ on Aortic Atherosclerosis in Apolipoprotein E-Deficient Mice" *Circulation* 97(8):780-785 (1998).

Shapiro et al., "Micro Assay for 3-Hydroxy-3-Methylglutaryl-CoA Reductase in Rat Liver and L-Cell Fibroblasts" *Biochim. Biophys. Acta* 370-369-377 (1974).

Sharrett et al., "Associations of Lipoprotein Cholesterols, Apolipoproteins A-l and B, and Triglycerides with Carotid Atherosclerosis and Coronary Heart Disease. The Atherosclerosis Risk in Communities (ARIC) Study" *Arterioscler. Thromb.* 14:1098-1104 (1994).

Sieber, R.H., "Reactions of chloroacetaldehyde with aromatic hydrocarbons, phenols, and phenol ethers" *Justus Liebigs Annalen der Chemie* 730:31-46 (1969) (German).

Sliwa et al., "Tautomerie entre structures α-aleoxy-enaminocetone et β-ceto iminoether presentee par les piperidines resultant de la semihydrogenation d'alcoxy-2-acyl-3 pyridines" *J. Heterocyclic Chem.* 16:939-944 (1979) (French).

Slowing et al., "Anti-Inflammatory Activity of Leaf Extracts of *Eugenia jambos* in Rats" *J. Ethnopharmacol.* 43:9-11 (1994).

Smyth et al., "Non-amine based analogues of lavendustin A as protein-tyrosine kinase inhibitors" *J. Med. Chem.* 36(20):3010-3014 (1993).

Sun et al., "In Vitro Testing of Drug Absorption for Drug 'Developability' Assessment: Forming an Interface Between in Vitro Preclinical Data and Clinical Outcome" *Curr. Opin. Drug Discov. Devel.* 7:75-85 (2004).

Suryadevara et al., "Association of Abnormal Serum Lipids in Elderly Persons with Artherosclerotic Vascular Disease and Demetia, Artheroslerotic Vascular Disease Without Demetia, Demetia Without Artherosclerotic Vascular Disease, and No Dementia or Artherosclerotic Vascular Disease" *J. Gerontol. Med. Sci.* 58A(9):859-861 (2003).

Tait et al., "Synthesis and Free Radical Scavenging Activity of 4-(2H-1,2,4-Benzothiadiazine-1,1-dioxide-3-yl)-2,6-bis(1,1-dimethylethyl)phenols" *Tetrahedron* 52(38):12587-12596 (1996).

Talbert; "Current Recommendations for the Treatment of Dyslipidemia" *Pharm. Ther.* 29:104-112 (2004).

Tanne et al., "High-Density Lipoprotein Cholesterol and Risk of Ischemic Stroke Mortaility" *Stroke* 28:83-87 (1997).

Tardif et al., "Probucol and Multivitamins in the Prevention of Restenosis After Coronary Angioplasty" *N. Engl. J. Med.* 337:365-367 (1997).

Theriault et al., "Modulation of hepatic lipoprotein synthesis and secretion by taxifolin, a plant flavonoid," *J. Lipid Res.* 41:1969-1979 (2000).

Toth et al., "Therapeutic Interventions Targeted at the Augmentation of Reserve Cholesterol Transport" *Curr. Opin. Cardiol.* 19:374-379 (2004).

Tovar et al., "Pyrylium Salts via Electrophilic Cyclization: Applications for Novel 3-Arylisoquinoline Syntheses" *J. Org. Chem.* 64:6499-6504 (1999).

Tudan, "Selective Inhibition of Protein Kinase C, Mitogen-Activated Protein Kinase, and Neutrophil Activation in Response to Calcium Pyrophosphate Dihydrate Crystals, Formyl-Methionyl-Leucyl-Phenylalanine, and Phorbol Ester by O-(Chloroacetyl-carbamoyl) Fumagillol (AGM-01470; TNP-470)" *Biochem. Pharmacol.* 58:1869-1880 (1999).

(56) References Cited

OTHER PUBLICATIONS

Utermann, "The Mysteries of Lipoprotein(a)" *Science* 246:904-910 (1989).
Van Der Goot et al., "The Growth-Inhibitory Action of Some 1-Aminoisoquinolines and Related Compounds on Mycoplasma Gallisepticum" *Eur. J. Med. Chem.—Chimica Thereapeutica* 10:603-606 (1975).
Varin et al., "Enzymatic Assay for Flavonoid Sulfotransferase" *Anal. Biochem.* 161:176-180 (1987).
Vippagunta et al., "Crystalline solids" *Adv. Drug Delivery Rev.* 48:3-26 (2001).
Walle, "Absorption and Metabolism of Flavonoids" *Free Radical Biol. Med.* 36(7):829-837 (2004).
Webster Ninth New Collegiate Dictionary, Definition of 'Prevent', 1 page (2000).
Wei et al., "Total Cholesterol and High Density Lipoprotein Cholesterol as Important Predictors of Erectile Dysfunction" *Am. J. Epidemiol*, 140(10):930-937 (1994).
Welsh et al., "Dyslipidemia in Diabetic Patients" *Prospectives in Cardiology*, Aug. 2002, pp. 40-48.
Wölle et al., "Selective inhibition of tumor necrosis factor-induced vascular cell adhesion molecule-1 gene expression by a novel flavonoid. Lack of effect on transcription factor NF-kappa-B" *Arterioscler. Thromb. Vasc. Biol.* 16(12):1501-1508 (1996).
Wurm et al., "1,4-Naphthoquinones, XXVI: Phenyl-1,4-naphthoquinone derivatives with the hydroxylation patterns of bioflavonoids" *Pharmazie* 52(10):739-743 (1997) (German).
Wurm, "1,4-Naphthoquinones, XXI: 2-(3,5 Di-*tert*-butyl-4-hydroxyphenyl)-1,4-naphtoquinones as 5-lipozxygenase inhibitors" *Archiv. der Pharmazie* 324(8):491-495 (1991).
Yamakoshi et al., "Isoflavone aglycone-rich extract without soy protein attenuates atherosclerosis development in cholesterol-fed rabbits" *Journal of Nutrition* 130(8):1887-1893 (2000).
Yardley et al., "In vitro activity of diospyrin and derivatives against *Leishmania donovani, Trypanosoma cruzi* and *Trypanosoma brucei brucei*" *Phytotherapy Research* 10(7):559-562 (1996).
Yoshioka et al., "Semiempirical Investigation of Stilbene-Linked Diradicals and Magnetic Study of Their Bis(*N-tert*-butylnitroxide) Variants" *J. Org. Chem.* 59(15):4272-4280 (1994).
Office Action in U.S. Appl. No. 11/255,103: Restriction Requirement, mailed Mar. 26, 2008.
Office Action in U.S Appl. No. 11/255,103, mailed Sep. 24, 2008.
Office Action in U.S. Appl. No. 11/255,103, mailed Aug. 31, 2009.
Office Action in U.S. Appl. No. 11/255,103, mailed Mar. 31, 2010.
Office Action in U.S. Appl. No. 11/255,103, mailed Nov. 10, 2010.
Office Action in U.S. Appl. No. 11/255,103: Notice of Allowance, mailed Jun. 7, 2011.
Office Action in U.S. Appl. No. 11/255,103: Notice of Allowance, mailed Sep. 15, 2011.
Office Action in U.S. Appl. No. 11/670,238: Restriction Requirement, mailed Mar. 31, 2010.
Office Action in U.S. Appl. No. 11/670,238: Restriction Requirement, mailed Jul. 20, 2010.
Office Action in U.S. Appl. No. 11/670,238, mailed Oct. 7, 2010.
Office Action in U.S. Appl. No. 11/670,238, mailed Apr. 19, 2011.
Office Action in U.S. Appl. No. 11/670,238, mailed Jun. 22, 2011.
Office Action in U.S. Appl. No. 11/670,238: Notice of Allowance, mailed Aug. 3, 2011.
Office Action in U.S. Appl. No. 11/670,238: Notice of Allowance, mailed Sep. 16, 2011.
Office Action in U.S. Appl. No. 11/990,162: Restriction Requirement, mailed Jul. 10, 2009.
Office Action in U.S. Appl. No. 11/990,162, mailed Oct. 14, 2009.
Office Action in U.S. Appl. No. 11/990,162, mailed Apr. 1, 2010.
Office Action in U.S. Appl. No. 11/990,162, mailed Dec. 28, 2010.
Office Action in U.S. Appl. No. 11/990,162, mailed Sep. 26, 2011.
Office Action in U.S. Appl. No. 11/990,162, mailed Mar. 19, 2012.
Office Action in U.S. Appl. No. 12/369,296, mailed Nov. 10. 2011.
Office Action in U.S. Appl. No. 12/369,296, mailed Mar. 13, 2012.
Office Action in U.S. Appl. No. 12/369,296: Notice of Allowance, mailed Apr. 12, 2012.
Office Action in U.S. Appl. No. 12/490,877, mailed Sep. 15, 2011.
Office Action in U.S. Appl. No. 12/490,877: Notice of Allowance, mailed Nov. 25, 2011.
Office Action in U.S. Appl. No. 13/243,776, mailed Apr. 11, 2013.
Office Action in U.S. Appl. No. 13/265,060, mailed Apr. 3, 2013.
Berliner et al., "Atherosclerosis: Basic Mechanisms Oxidation, Inflammation and Genetics" *Circulation*, 91:2488-2496 (1995).
International Search Report and Written Opinion issued in International Application No. PCT/IB2013/003031: Date of Mailing: May 28, 2014.
Jafri et al., "Baseline and on-treatment high-density lipoprotein cholesterol and the risk of cancer in randomized controlled trials of lipid-altering therapy" *J Am Coll Cardiol*, 55:2846-2854 (2010).
Landi et al., "HDL-cholesterol and physical performance: results from the ageing and longevity study in the sirente geographic area (*ilSirente* Study)" *Age and Ageing*, 36(5):514-520 (2007).
McGrowder et al., "The role of high density lipoproteins in reducing the risk of vascular diseases, neurogenerative disorders, and cancer" *Cholesterol*, 2011, Article 496925, 9 pages.
Mitchell et al., "Bromination of 4,6-dimethoxyindoles" *Tetrahedron*, 68(39):8163-8171 (2012).
Reitz et al., "Association of higher levels of high-density lipoprotein cholesterol in elderly individuals and lower risk of late-onset Alzheimer Disease" *Arch Neurol*, 67(12):1491-1497 (2010).
Rubins et al for the Veterans Affairs High-Density Lipoprotein Cholesterol Intervention Trial Study Group, "Gemfibrozil for the secondary prevention of coronary heart disease in men with low levels of high-density lipoprotein cholesterol" *N. Engl. J. Med.*, 341:410-418 (1999).
Schultz et al., "Protein composition determines the anti-atherogenic properties of HDL in transgenic mice" *Nature*, 365:762-764 (1993).
Singh-Manoux et al., "Low HDL cholesterol is a risk factor for deficit and decline in memory in midlife: the Whitehall II Study" Atherosclerosis, Thrombosis and Vascular Biology, 28(8):1556-1562 (2008).
Stampfer, "Cardiovascular disease and Alzheimer's disease. common links" *J Intern Med*, 260(3):211-223 (2006).
Andersson, "Pharmacology of apolipoprotein A-I" *Curr. Opin. Lipidol.* 8:225-228 (1997).
Badimon et al. "Regression of Atherosclerotic Lesions by High Density Lipoprotein Plasma Fraction in the Cholesterol-fed Rabbit" *J. Clin. Invest.* 85: 1234-1241 (1990).
Miyazaki, et al. "Intravenous Injection of Rabbit Apolipoprotein A-I Inhibits the Progression of Atherosclerosis in Cholesterol-Fed Rabbits" *Arterioscler, Thromb, Vasc Biol.* 15: 1882-1888 (1995).
Tall "Plasma High Density Lipoproteins" *J. Clin. Invest.* 86: 379-384 (1990).

COMPOUNDS FOR THE PREVENTION AND TREATMENT OF CARDIOVASCULAR DISEASE

This application is a national stage entry under 35 U.S.C. § 371 of PCT/IB2010/000159, filed Jan. 8, 2010, which claims the benefit of U.S. Provisional Application No. 61/143,276, filed on Jan. 8,2009, the disclosure of which is incorporated herein by reference in its entirety.

The invention provides novel compounds that are useful for regulating the expression of apolipoprotein A-I (ApoA-I), and their use for the treatment and prevention of cardiovascular disease and related disease states, including cholesterol- or lipid-related disorders, such as, for example, atherosclerosis. The invention also includes pharmaceutical compositions comprising the novel compounds, as well as methods for their preparation.

Epidemiological data demonstrate an inverse relationship between circulating levels of high density lipoprotein cholesterol (HDL-C) and the incidence of clinically significant atherosclerosis. Each 1 mg/dL increment in the HDL-C serum level is associated with a 2-3% decrement in cardiovascular risk; a 1% reduction in LDL-C reduces coronary heart disease (CHD) risk by 2% (Gordon et al. (1997) *Am. J. Med.* 62, 707-714).

Experimental evidence further supports the protective effect of HDL-C against cardiovascular disease. For example, in subjects with low HDL-C, administration of gemfibrozil results in a 6% increase in the HDL-C level and a corresponding 22% reduction of the CHD risk (Rubins et al. (1999) *N. Engl. J. Med.* 341, 410-418). Observations in genetic disorders associated with low HDL-C (due to reduced ApoA-I expression) also indicate the link between elevated risk of CHD and low HDL-C.

HDL-C appears to exert its anti-atherogenic effect by mediating reverse cholesterol transport (RCT), in which cholesterol is recruited from peripheral tissues and transported to the liver. Additionally, HDL-C also exerts anti-inflammatory and anti-oxidant effects and promotes fibrinolysis. HDL-C particles protect against oxidation of LDL, an important initial step in promoting cholesterol uptake by arterial macrophages. HDL-C exists in two main forms, one containing both apolipoprotein A-I (ApoA-I) and apolipoprotein A-II (ApoA-II), and the other containing ApoA-I alone (Schultz et al. (1993) *Nature* 365, 762-764). The cardioprotective effect of HDL-C is largely, but not exclusively, attributable to ApoA-I.

Clinical and experimental data suggest that the production of ApoA-I is an important determinant of circulating HDL-C. For example, persons with familial hyperalphalipoproteinemia (elevated ApoA-I) appear to be protected from atherosclerosis, while those deficient in ApoA-I (hypoalphalipoproteinemia) show accelerated cardiovascular disease. In addition, various experimental manipulations to increase production of ApoA-I are associated with reduced atherogenicity. For example, human ApoA-I is protective in transgenic animal models (Shah et al. (1998) *Circulation* 97, 780-785 and Rubin et al. (1991) *Nature* 353, 265-267), and treatment with ApoA-I$_{Milano}$ prevents atherosclerotic lesions and leads to regression of atherosclerotic plaques in human patients (Nissen et al. (2003) *JAMA* 290, 2292-2300). Further lines of research demonstrate that ApoA-I plays a role in enhancing reverse cholesterol transport, attenuating oxidative stress, increasing paraoxonase activity, enhancing anticoagulant activity, and increasing anti-inflammatory activity (Andersson (1997) *Curr. Opin. Lipidol.* 8, 225-228). Accordingly, ApoA-I is an attractive target for therapeutic intervention.

Currently available therapeutic agents that increase the plasma concentration of ApoA-I, for example, recombinant ApoA-I or peptides that mimic ApoA-I, have potential drawbacks with respect to, e.g., stability during storage, delivery of active product, and in vivo half-life. Thus, small molecule compounds that up-regulate the production of endogenous ApoA-I, such as, for example, up-regulators of ApoA-I expression, would be attractive as new therapeutic agents for the treatment and/or prevention of cardiovascular disease. Such small molecule compounds have been described in, for example, WO 2006/045096. However, there is still a need for therapeutic agents that can increase the plasma concentration of ApoA1 and/or increase levels of circulating HDL-C.

Thus, the present invention provides non-naturally occurring compounds that are useful for regulating the expression of apolipoprotein A-I (ApoA-I) and/or regulating expression of HDL-C, as well as the use of such compounds for the treatment and prevention of cardiovascular disease and related disease states, including cholesterol- and lipid-related disorders, such as, for example, atherosclerosis.

In one embodiment of the invention, compounds that may be used to treat and/or prevent cardiovascular, cholesterol, and/or lipid related disorders in a subject are selected from compounds of Formula I:

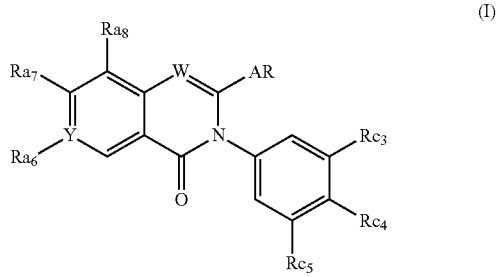

(I)

and stereoisomers, tautomers, pharmaceutically acceptable salts, and hydrates thereof,
wherein:

Y and W are each independently selected from carbon and nitrogen;

$Ra_6$ is selected from fluoride, hydrogen, $C_1$-$C_3$ alkoxy, cyclopropyloxy, $SO_2R_3$, $SOR_3$, and $SR_3$, wherein if Y is nitrogen then $Ra_6$ is absent;

$Ra_7$ is selected from hydrogen, fluoride, $SO_2R_3$, $SOR_3$, and $SR_3$;

$Ra_8$ is selected from hydrogen, $C_1$-$C_3$ alkoxy, cyclopropyloxy, chloride, and bromide;

AR is

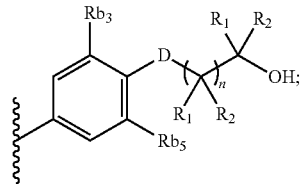

n is selected from 1, 2, or 3;
D is selected from O, NH, $NR_1$, S, or C;
$R_{b_3}$ and $R_{b_5}$ are independently selected from hydrogen and $C_1$-$C_3$ alkyl;

$R_{c_3}$ and $R_{c_5}$ are independently selected from hydrogen, $C_1$-$C_3$ alkyl, and cyclopropyl;

$R_{c_4}$ is selected from F, Cl, Br, I, $CF_3$, $C_1$-$C_6$ alkyl, $C_3$-$C_6$ cycloalkyl, $NHC(O)R_4$, $NHSO_2R_4$, $C(O)OR_4$, and

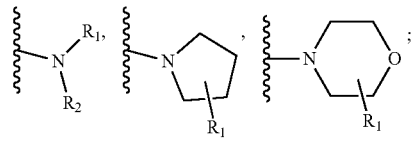

$R_1$, $R'_1$, $R_2$ and $R'_2$ are independently selected from hydrogen, fluoride, $C_1$-$C_3$ alkyl, and cyclopropyl, wherein $R_1$ and $R_2$ and/or $R'_1$ and $R'_2$ may be connected to form a 3-6 membered ring;

$R_3$ is selected from $C_1$-$C_3$ alkyl, and cyclopropyl; and $R_4$ is selected from hydrogen, $C_1$-$C_4$ alkyl, $C_3$-$C_5$ cycloalkyl, and aryl, provided that if $R_{a_7}$ or $R_{a_6}$ is fluoride, then $R_{c_4}$ is not bromide.

In another embodiment of the invention, compounds that may be used to treat and/or prevent cardiovascular, cholesterol, and/or lipid related disorders in a subject are selected from compounds of Formula II:

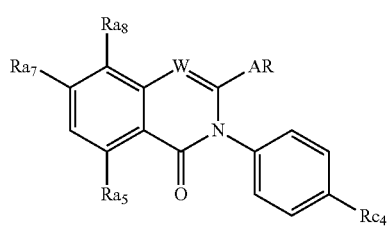

(II)

and tautomers, stereoisomers, pharmaceutically acceptable salts, and hydrates thereof,
wherein:
W is carbon or nitrogen;
AR is

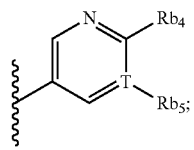

T is carbon or nitrogen;
$R_{a_5}$, $R_{a_7}$, and $R_{a_8}$ are independently selected from hydrogen and fluoride;
$Rb_4$ is selected from hydrogen, Cl, Br, F, $CF_3$, $C_1$-$C_4$ alkyl, $C_3$-$C_5$ cycloalkyl, $C_1$-$C_4$ alkoxy, $C_3$-$C_5$ cycloalkoxy, methoxy, -Oaryl, phenyl, $CH_2OH$, $—CH_2$-morpholino, morpholino, piperidinyl, $—CH_2$piperazino, $—CH_2$(N-methylpiperazino), $—NR_1R_2$, and $—CH_2NR_1R_2$;
$R_{b_5}$ is selected from hydrogen, Cl, Br, F, aryl, and $—NR_1R_2$, wherein $R_{b_4}$ and $R_{b_5}$ may be connected to form a ring;
$R_{c_4}$ is selected from Cl, Br, $C_2$-$C_5$ alkyl, $C_3$-$C_5$ cycloalkyl, $—NHSO_2R_1$, $—NR_1R_2$; and
$R_1$ and $R_2$ are independently selected from $C_1$-$C_4$ alkyl and $C_3$-$C_6$ cycloalkyl wherein $R_1$ and $R_2$ may be connected to form a 3-6-membered ring, provided that
if $R_{b_4}$ is fluoride, phenyl, methoxy, $—CH_2OH$, $—CH_2$morpholino, morpholino, $—CH_2$piperazino, or $—CH_2$(N-methylpiperazino) then $R_{c_4}$ is not chloride;
if $R_{a_7}$ or $R_{a_6}$ is fluoride, then $R_{c_4}$ is not bromide;
if $R_{b_5}$ is fluoride then $R_{c_4}$ is not chloride;
if $R_{c_4}$ is chloride or bromide, then at least one of $R_{b_2}$, $R_{b_4}$, or $R_{b_5}$ is not hydrogen;
if T is N, then $R_{c_4}$ is not halogen; and
if AR is

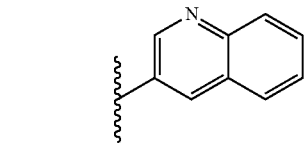 [SMILES: *c1cnc2ccccc2c1]

then $R_{c_4}$ is not sec-butyl.

A further embodiment of the invention, compounds that may be used to treat and/or prevent cardiovascular, cholesterol, and/or lipid related disorders in a subject are selected from compounds of Formula III:

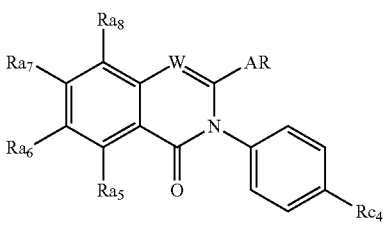

(III)

and tautomers, stereoisomers, pharmaceutically acceptable salts, and hydrates thereof
wherein:
wherein:
AR is selected from:

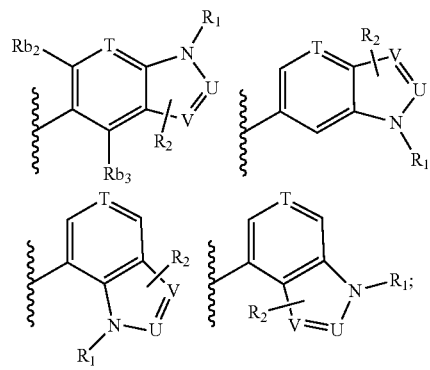

T, U, and V are independently selected from carbon and nitrogen;
$R_1$ is selected from hydrogen, $C_1$-$C_5$ alkyl, $C_3$-$C_5$ cycloalkyl, and $—SO_2R_3$;
$R_2$ is selected from hydrogen, $C_1$-$C_5$ alkyl, $C_3$-$C_5$ cycloalkyl, and $CH_2OH$;
$R_3$ is selected from hydrogen, $C_1$-$C_5$ alkyl, $C_3$-$C_5$ cycloalkyl, and optionally substituted aryl;

$R_{a_5}$, $R_{a_6}$, $R_{a_7}$, and $R_{a_8}$ are independently selected from hydrogen and fluoride;

$R_{b_2}$ and $R_{b_3}$ are independently selected from hydrogen, F, Cl, Br, $C_1$-$C_3$ alkyl, cyclopropyl, and $C_1$-$C_3$ alkoxy;

$R_{c_4}$ is selected from $C_2$-$C_6$ alkyl, $C_3$-$C_6$ cycloalkyl, F, Cl, Br, I, $OCF_3$, and —$NR_4R_5$;

$R_4$ is selected from hydrogen, $C_1$-$C_5$ alkyl, and $C_3$-$C_5$ cycloalkyl; and $R_5$ is selected from hydrogen, $C_1$-$C_5$ alkyl, and $C_3$-$C_5$ cycloalkyl;

provided that if $R_1$ is methyl, then $R_{c_4}$ is not sec-butyl; and if $R_2$ is —$CH_2OH$, then $R_{c_4}$ is not Cl.

The invention also provides pharmaceutical compositions comprising one or more compounds of the invention, (i.e., compounds of Formula I, Formula II, and Formula III, and stereoisomers, tautomers, pharmaceutically acceptable salts, and hydrates of compounds of Formula I, II, and III) together with at least one pharmaceutically acceptable vehicle chosen from carriers, adjuvants, and excipients. In addition, methods of preparing compounds of Formula I, Formula II, and Formula III, and stereoisomers, tautomers, and pharmaceutically acceptable salts and hydrates thereof are encompassed by the invention.

The invention further provides methods of treating and/or preventing cardiovascular diseases, cholesterol-related disorders and/or lipid-related disorders by administering to a subject in need thereof, a therapeutically effective amount of one or more compounds of Formula I, Formula II, Formula III, or tautomers, stereoisomers, pharmaceutically acceptable salts, or hydrates of compounds of Formula I, Formula II, Formula III. The invention also includes methods of increasing the expression of ApoA-I and/or HDL-C in a subject, such as a human, comprising administering a therapeutically effective amount of any of the compounds of the invention described herein or a pharmaceutically acceptable composition comprising one or more compounds of the invention.

Definitions

As used in the present specification, the following words, phrases and symbols are generally intended to have the meanings as set forth below, except to the extent that the context in which they are used indicates otherwise. The following abbreviations and terms have the indicated meanings throughout:

"Subject" refers to an animal, such as a mammal, that has been or will be the object of treatment, observation, or experiment. The methods described herein may be useful for both human therapy and veterinary applications. In one embodiment, the subject is a human.

As used herein, "cardiovascular disease" refers to diseases and disorders of the heart and circulatory system. Exemplary cardiovascular diseases, including cholesterol- or lipid-related disorders, include, but are not limited to, acute coronary syndrome, angina, arteriosclerosis, atherosclerosis, carotid atherosclerosis, cerebrovascular disease, cerebral infarction, congestive heart failure, congenital heart disease, coronary heart disease, coronary artery disease, coronary plaque stabilization, dyslipidemias, dyslipoproteinemias, endothelium dysfunctions, familial hypercholeasterolemia, familial combined hyperlipidemia, hypoalphalipoproteinemia, hypertriglyceridemia, hyperbetalipoproteinemia, hypercholesterolemia, hypertension, hyperlipidemia, intermittent claudication, ischemia, ischemia reperfusion injury, ischemic heart diseases, cardiac ischemia, metabolic syndrome, multi-infarct dementia, myocardial infarction, obesity, peripheral vascular disease, reperfusion injury, restenosis, renal artery atherosclerosis, rheumatic heart disease, stroke, thrombotic disorder, transitory ischemic attacks, and lipoprotein abnormalities associated with Alzheimer's disease, obesity, diabetes mellitus, syndrome X, impotence, multiple sclerosis, Parkinson's diseases and an inflammatory diseases.

As used herein, "treatment" or "treating" refers to an amelioration of a disease or disorder, or at least one discernible symptom thereof. In one embodiment, "treatment" or "treating" refers to an amelioration of at least one measurable physical parameter, not necessarily discernible by the subject. In another embodiment, "treatment" or "treating" refers to inhibiting the progression of a disease or disorder, either physically, e.g., stabilization of a discernible symptom, physiologically, e.g., stabilization of a physical parameter, or both. In another embodiment, "treatment" or "treating" refers to delaying the onset of a disease or disorder. For example, treating a cholesterol disorder may comprise decreasing blood cholesterol levels.

As used herein, "prevention" or "preventing" refers to a reduction of the risk of acquiring a given disease or disorder.

A dash ("-") that is not between two letters or symbols is used to indicate a point of attachment for a substituent. For example, —$CONH_2$ is attached through the carbon atom.

By "optional" or "optionally" is meant that the subsequently described event or circumstance may or may not occur, and that the description includes instances where the event or circumstance occurs and instances in which is does not. For example, "optionally substituted aryl" encompasses both "aryl" and "substituted aryl" as defined below. It will be understood by those skilled in the art, with respect to any group containing one or more substituents, that such groups are not intended to introduce any substitution or substitution patterns that are sterically impractical, synthetically non-feasible and/or inherently unstable.

The term "aldehyde" or "formyl" as used herein refers to —CHO.

The term "alkenyl" as used herein refers to an unsaturated straight or branched hydrocarbon having at least one carbon-carbon double bond, such as a straight or branched group of 2-22, 2-8, or 2-6 carbon atoms, referred to herein as ($C_2$-$C_{22}$) alkenyl, ($C_2$-$C_8$)alkenyl, and ($C_2$-$C_6$)alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkoxy" as used herein refers to an alkyl group attached to an oxygen (—O-alkyl-). "Alkoxy" groups also include an alkenyl group attached to an oxygen ("alkenyloxy") or an alkynyl group attached to an oxygen ("alkynyloxy") groups. Exemplary alkoxy groups include, but are not limited to, groups with an alkyl, alkenyl or alkynyl group of 1-22, 1-8, or 1-6 carbon atoms, referred to herein as ($C_1$-$C_{22}$) alkoxy, ($C_1$-$C_8$)alkoxy, and ($C_1$-$C_8$)alkoxy, respectively. Exemplary alkoxy groups include, but are not limited to methoxy and ethoxy.

The term "alkyl" as used herein refers to a saturated straight or branched hydrocarbon, such as a straight or branched group of 1-22, 1-8, or 1-6 carbon atoms, referred to herein as ($C_1$-$C_{22}$)alkyl, ($C_1$-$C_8$)alkyl, and ($C_1$-$C_6$)alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl.

The term "alkynyl" as used herein refers to an unsaturated straight or branched hydrocarbon having at least one carbon-carbon triple bond, such as a straight or branched group of 2-22, 2-8, or 2-6 carbon atoms, referred to herein as ($C_2$-$C_{22}$) alkynyl, ($C_2$-$C_8$)alkynyl, and ($C_2$-$C_6$)alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl.

The term "amide" as used herein refers to a group having the formula —$NR_aC(O)(R_b)$— or —$C(O)NR_bR_c$, wherein $R_a$, $R_b$, and $R_c$ are each independently selected from alkyl, alkenyl, alkynyl, aryl, arylalkyl, cycloalkyl, haloalkyl, heteroaryl, heterocyclyl, and hydrogen. The amide can be attached to another group through the carbon, the nitrogen, $R_b$, or $R_c$. The amide also may be cyclic, for example $R_b$ and $R_c$ may be joined to form a 3- to 12-membered ring, such as a 3- to 10-membered ring or a 5- to 6-membered ring. The term "amide" encompasses groups such as sulfonamide, urea, ureido, carbamate, carbamic acid, and cyclic versions thereof. The term "amide" also encompasses an amide group attached to a carboxy group, e.g., -amide-COOH or salts thereof, such as -amide-COONa, etc., an amino group attached to a carboxy group, e.g., -amino-COOH or salts thereof, such as -amino-COONa.

The term "amine" or "amino" as used herein refers to a group having the formula —$NR_dR_e$ or —$N(R_d)R_e$—, where $R_d$ and $R_e$ are independently selected from alkyl, alkenyl, alkynyl, aryl, arylalkyl, carbamate, cycloalkyl, haloalkyl, heteroaryl, heterocyclyl, and hydrogen. The amino can be attached to the parent molecular group through the nitrogen. The amino may also be cyclic, for example, any two of $R_d$ and $R_e$ may be joined together or with the N atom to form a 3- to 12-membered ring, e.g., morpholino or piperidinyl. The term amino also includes the corresponding quaternary ammonium salt of any amino group. Exemplary amino groups include alkylamino groups, wherein at least one of $R_d$ or $R_e$ is an alkyl group.

The term "aryl" or "aryl group" as used herein refers to a mono-, bi-, or other multi-carbocyclic, aromatic ring system. The aryl group can be optionally fused to one or more rings selected from aryl, cycloalkyl, and heterocyclyl. Aryl groups as disclosed herein can be optionally substituted with one or more groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "($C_6$)aryl."

The term "arylalkyl" as used herein refers to an alkyl group having at least one aryl substituent, e.g. -aryl-alkyl-. Exemplary arylalkyl groups include, but are not limited to, arylalkyls having a monocyclic aromatic ring system, wherein the ring comprises 6 carbon atoms, referred to herein as "($C_6$) arylalkyl."

The term "aryloxy" as used herein refers to an aryl group attached to an oxygen atom. Exemplary aryloxy groups include, but are not limited to, aryloxys having a monocyclic aromatic ring system, wherein the ring comprises 6 carbon atoms, referred to herein as "($C_6$)aryloxy."

The term "arylthio" as used herein refers to an aryl group attached to an sulfur atom. Exemplary arylthio groups include, but are not limited to, arylthios having a monocyclic aromatic ring system, wherein the ring comprises 6 carbon atoms, referred to herein as "($C_6$)arylthio."

The term "arylsulfonyl" as used herein refers to an aryl group attached to a sulfonyl group, e.g., —$S(O)_2$-aryl-. Exemplary arylsulfonyl groups include, but are not limited to, arylsulfonyls having a monocyclic aromatic ring system, wherein the ring comprises 6 carbon atoms, referred to herein as "($C_6$)arylsulfonyl."

The term "benzyl" as used herein refers to the group —$CH_2$-phenyl.

The term "bicyclic aryl" as used herein refers to an aryl group fused to another aromatic or non-aromatic carbocyclic or heterocyclic ring. Exemplary bicyclic aryl groups include, but are not limited to, naphthyl or partly reduced forms thereof, such as di-, tetra-, or hexahydronaphthyl.

The term "bicyclic heteroaryl" as used herein refers to a heteroaryl group fused to another aromatic or non-aromatic carbocyclic or heterocyclic ring. Exemplary bicyclic heteroaryls include, but are not limited to, 5, 6 or 6,6-fused systems wherein one or both rings contain heteroatoms. The term "bicyclic heteroaryl" also encompasses reduced or partly reduced forms of fused aromatic system wherein one or both rings contain ring heteroatoms. The ring system may contain up to three heteroatoms, independently selected from oxygen, nitrogen, or sulfur. The bicyclic system may be optionally substituted with one or more groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Exemplary bicyclic heteroaryl's include, but are not limited to, quinazolinyl, benzothiophenyl, benzoxazolyl, benzimidazolyl, benzothiazolyl, benzofuranyl, indolyl, quinolinyl, isoquinolinyl, phthalazinyl, benzotriazolyl, benzopyridinyl, and benzofuranyl.

The term "carbamate" as used herein refers to the form —$R_gOC(O)N(R_h)$—, —$R_gOC(O)N(R_h)R_i$—, or —$OC(O)NR_hR_i$, wherein $R_g$, $R_h$, and $R_i$ are each independently selected from alkyl, alkenyl, alkynyl, aryl, arylalkyl, cycloalkyl, haloalkyl, heteroaryl, heterocyclyl, and hydrogen. Exemplary carbamates include, but are not limited to, arylcarbamates or heteroaryl carbamates, e.g., wherein at least one of $R_g$, $R_h$, and $R_i$ are independently selected from aryl or heteroaryl, such as pyridine, pyridazine, pyrimidine, and pyrazine.

The term "carbonyl" as used herein refers to —$C(O)$—.

The term "carboxy" as used herein refers to —COOH or corresponding carboxylate salts, e.g. —COONa, etc. The term carboxy also includes "carboxycarbonyl" e.g., a carboxy group attached to a carbonyl group, e.g., —$C(O)$—COOH or salts thereof, such as —$C(O)$—COONa.

The term "cyano" as used herein refers to —CN.

The term "cycloalkoxy" as used herein refers to a cycloalkyl group attached to an oxygen.

The term "cycloalkyl" as used herein refers to a saturated or unsaturated cyclic, bicyclic, or bridged bicyclic hydrocarbon group of 3-12 carbons, or 3-8 carbons, referred to herein as "($C_3$-$C_8$)cycloalkyl," derived from a cycloalkane. Exemplary cycloalkyl groups include, but are not limited to, cyclohexanes, cyclohexenes, cyclopentanes, and cyclopentenes. Cycloalkyl groups may be optionally substituted with one or more groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Cycloalkyl groups can be fused to other cycloalkyl saturated or unsaturated, aryl, or heterocyclyl groups.

The term "dicarboxylic acid" as used herein refers to a group containing at least two carboxylic acid groups such as saturated and unsaturated hydrocarbon dicarboxylic acids and salts thereof. Exemplary dicarboxylic acids include, but are not limited to alkyl dicarboxylic acids. Dicarboxylic acids may be optionally substituted with one or more groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide, and thioketone. Dicarboxylic acids include, but are not limited to succinic acid, glutaric acid, adipic acid, suberic acid, sebacic acid, azelaic acid, maleic acid, phthalic acid, aspartic acid, glutamic acid, malonic acid, fumaric acid, (+)/(−)-malic acid, (+)/(−) tartaric acid, isophthalic acid, and terephthalic acid. Dicarboxylic acids further include carboxylic acid derivatives thereof, such as anhydrides, imides, and hydrazides, for example, succinic anhydride and succinimide.

The term "ester" refers to the structure —C(O)O—, —C(O)O—$R_j$—, —$R_k$C(O)O—$R_j$— or —$R_k$C(O)O—, where the oxygen atom is not bound to hydrogen, and $R_j$ and $R_k$ can be independently selected from alkoxy, aryloxy, alkyl, alkenyl, alkynyl, amide, amino, aryl, arylalkyl, cycloalkyl, ether, haloalkyl, heteroaryl, and heterocyclyl. $R_k$ can be a hydrogen, but $R_j$ cannot be hydrogen. The ester may be cyclic, for example the carbon atom and $R_j$, the oxygen atom and $R_k$, or $R_j$ and $R_k$ may be joined to form a 3- to 12-membered ring. Exemplary esters include, but are not limited to, alkyl esters wherein at least one of $R_j$ or $R_k$ is alkyl, such as —O—C(O)-alkyl, —C(O)—O-alkyl-, -alkyl-C(O)—O-alkyl-, etc. Exemplary esters also include aryl or heteoraryl esters, e.g. wherein at least one of $R_j$ or $R_k$ is a heteroaryl group such as pyridine, pyridazine, pyrimidine and pyrazine, such as a nicotinate ester. Exemplary esters also include reverse esters having the structure —$R_k$C(O)O—, where the oxygen is bound to the parent molecular. Exemplary reverse esters include succinate, D-argininate, L-argininate, L-lysinate, and D-lysinate. Esters also include carboxylic acid anhydrides and acid halides.

The term "ether" refers to the structure —$R_l$O—$R_m$—, where $R_l$ and $R_m$ can be independently selected from alkyl, alkenyl, alkynyl, aryl, cycloalkyl, heterocyclyl, or ether. The ether can be attached to the parent molecular group through $R_l$ or $R_m$. Exemplary ethers include, but are not limited to, alkoxyalkyl and alkoxyaryl groups. Ethers also includes polyethers, e.g., where one or both of $R_l$ and $R_m$ are ethers.

The terms "halo" or "halogen" or "Hal" as used herein refer to F, Cl, Br, or I.

The term "haloalkyl" as used herein refers to an alkyl group substituted with one or more halogen atoms. "Haloalkyls" also encompass alkenyl or alkynyl groups substituted with one or more halogen atoms.

The term "heteroaryl" as used herein refers to a mono-, bi-, or multi-cyclic, aromatic ring system containing one or more heteroatoms, for example 1 to 3 heteroatoms, such as nitrogen, oxygen, and sulfur. Heteroaryls can be optionally substituted with one or more substituents selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2 to 5 carbon atoms and 1 to 3 heteroatoms, referred to herein as "($C_2$-$C_5$)heteroaryl."

The terms "heterocycle," "heterocyclyl," or "heterocyclic" as used herein refer to a saturated or unsaturated 3-, 4-, 5-, 6-, 7-, or 8-membered ring containing one, two, or three heteroatoms independently selected from nitrogen, oxygen, and sulfur. Heterocycles can be aromatic (heteroaryls) or non-aromatic. Heterocycles can be optionally substituted with one or more substituents selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Heterocycles also include bicyclic, tricyclic, and tetracyclic groups where any of the above heterocyclic rings are fused to one or two rings independently selected from aryl, cycloalkyl, and heterocycle. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

The terms "hydroxy" and "hydroxyl" as used herein refer to —OH.

The term "hydroxyalkyl" as used herein refers to a hydroxy attached to an alkyl group.

The term "hydroxyaryl" as used herein refers to a hydroxy attached to an aryl group.

The term "ketone" as used herein refers to the structure —C(O)—Rn (such as acetyl, e.g., —C(O)$CH_3$) or —$R_n$—C(O)—$R_o$. The ketone can be attached to another group through $R_n$ or $R_o$. $R_n$ or $R_o$ can be independently selected from alkyl, alkenyl, alkynyl, cycloalkyl, heterocyclyl, and aryl, or $R_n$ or $R_o$ can be joined to form a 3- to 12-membered ring.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic, and maleic acid.

The term "nitro" as used herein refers to the —$NO_2$.

The term "perfluoroalkoxy" as used herein refers to an alkoxy group in which all of the hydrogen atoms have been replaced by fluorine atoms.

The term "perfluoroalkyl" as used herein refers to an alkyl group in which all of the hydrogen atoms have been replaced by fluorine atoms. Exemplary perfluoroalkyl groups include, but are not limited to, $C_{1-5}$ perfluoroalkyl, such as trifluoromethyl.

The term "perfluorocycloalkyl" as used herein refers to a cycloalkyl group in which all of the hydrogen atoms have been replaced by fluorine atoms.

The term "phenyl" as used herein refers to a 6-membered carbocyclic aromatic ring. The phenyl group can also be fused to a cyclohexane or cyclopentane ring. Phenyl can be optionally substituted with one or more substituents selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone.

The term "phosphate" as used herein refers to the structure —OP(O)O$_2$—, —R$_x$OP(O)O$_2$—, —OP(O)O$_2$R$_y$—, or —R$_x$OP(O)O$_2$R$_y$—, wherein R$_x$ and R$_y$ can be independently selected from alkyl, alkenyl, alkynyl, aryl, cycloalkyl, heterocyclyl, and hydrogen The term "sulfide" as used herein refers to the structure —R$_z$S—, where R$_z$ is selected from alkyl, alkenyl, alkynyl, aryl, arylalkyl, cycloalkyl, haloalkyl, heteroaryl, and heterocyclyl. The sulfide may be cyclic, forming a 3 to 12-membered ring. The term "alkylsulfide" as used herein refers to an alkyl group attached to a sulfur atom.

The term "sulfinyl" as used herein refers to the structure —S(O)O—, —R$_p$S(O)O—, —R$_p$S(O)OR$_q$—, or —S(O)OR$_q$—, wherein R$_p$ and R$_q$ can be independently selected from alkyl, alkenyl, aryl, arylalkyl, cycloalkyl, haloalkyl, heteroaryl, heterocyclyl, and hydroxyl. Exemplary sulfinyl groups include, but are not limited to, alkylsulfinyls wherein at least one of R$_p$ or R$_q$ is selected from alkyl, alkenyl, and alkynyl.

The term "sulfonamide" as used herein refers to the structure —(R$_r$)—N—S(O)$_2$—R$_s$— or —R$_t$(R$_r$)—N—S(O)$_2$—R$_s$, where R$_t$, R$_r$, and R$_s$ are independently selected from, for example, hydrogen, alkyl, alkenyl, alkynyl, aryl, cycloalkyl, and heterocyclyl. Exemplary sulfonamides include alkylsulfonamides (e.g., where R$_s$ is alkyl), arylsulfonamides (e.g., where R$_s$ is aryl), cycloalkyl sulfonamides (e.g., where R$_s$ is cycloalkyl), and heterocyclyl sulfonamides (e.g., where R$_s$ is heterocyclyl).

The term "sulfonate" as used herein refers to –OSO$_3^-$. Sulfonate also encompasses salts such as —OSO$_3$Na, —OSO$_3$K and the like, in addition to the acid —OSO$_3$H.

The term "sulfonic acid" refers to —SO$_3$H— and corresponding salts thereof, e.g. —SO$_3$K—, and —SO$_3$Na—.

The term "sulfonyl" as used herein refers to the structure R$_u$SO$_2$—, where R$_u$ is selected from alkyl, alkenyl, alkynyl, aryl, cycloalkyl, and heterocyclyl, e.g., alkylsulfonyl. The term "alkylsulfonyl" as used herein refers to an alkyl group attached to a sulfonyl group. "Alkylsulfonyl" groups can optionally contain alkenyl or alkynyl groups.

The term "thioketone" refers to the structure —R$_v$—C(S)—R$_w$—. The ketone can be attached to another group through R$_v$ or R$_w$. R$_v$ or R$_w$ is selected from alkyl, alkenyl, alkynyl, cycloalkyl, heterocyclyl, and aryl, or R$_v$ or R$_w$ can be joined to form a 3- to 12-membered ring.

"Alkyl," "alkenyl," "alkynyl", "alkoxy", "amino" and "amide" groups can be substituted with or interrupted by or branched with at least one group selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, thioketone, ureido, and N. The substituents may be branched to form a substituted or unsubstituted heterocycle or cycloalkyl.

As used herein, a "suitable substituent" refers to a group that does not nullify the synthetic or pharmaceutical utility of the compounds of the invention or the intermediates useful for preparing them. Examples of suitable substituents include, but are not limited to: $C_{1-22}$, $C_{1-8}$, and $C_{1-6}$ alkyl, alkenyl or alkynyl; $C_{1-6}$ aryl, $C_{2-5}$ heteroaryl; $C_{3-7}$ cycloalkyl; $C_{1-22}$, $C_{1-8}$, and $C_{1-6}$ alkoxy; $C_6$ aryloxy; —CN; —OH; oxo; halo, carboxy; amino, such as —NH($C_{1-22}$, $C_{1-8}$, or $C_{1-6}$ alkyl), —N($C_{1-22}$, $C_{1-8}$, and $C_{1-6}$ alkyl)$_2$, —NH(($C_6$)aryl), or —N(($C_6$)aryl)$_2$; formyl; ketones, such as —CO($C_{1-22}$, $C_{1-8}$, and $C_{1-6}$ alkyl), —CO(($C_6$ aryl) esters, such as —CO$_2$($C_{1-22}$, $C_{1-8}$, and $C_{1-6}$ alkyl) and —CO$_2$($C_6$ aryl). One of skill in art can readily choose a suitable substituent based on the stability and pharmacological and synthetic activity of the compound of the invention.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutically acceptable composition" as used herein refers to a composition comprising at least one compound as disclosed herein formulated together with one or more pharmaceutically acceptable carriers.

The term "pharmaceutically acceptable prodrugs" as used herein represents those prodrugs of the compounds of the present invention that are, within the scope of sound medical judgment, suitable for use in contact with the tissues of humans and lower animals without undue toxicity, irritation, allergic response, commensurate with a reasonable benefit/risk ratio, and effective for their intended use, as well as the zwitterionic forms, where possible, of the compounds of the invention. A discussion is provided in Higuchi et al., "Prodrugs as Novel Delivery Systems," *ACS Symposium Series*, Vol. 14, and in Roche, E. B., ed. *Bioreversible Carriers in Drug Design*, American Pharmaceutical Association and Pergamon Press, 1987, both of which are incorporated herein by reference.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well known asymmetric synthetic methods.

Geometric isomers can also exist in the compounds of the present invention. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers.

Substituents around a carbon-carbon double bond alternatively can be referred to as "cis" or "trans," where "cis" represents substituents on the same side of the double bond and "trans" represents substituents on opposite sides of the double bond. The arrangements of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein may exist as tautomers and both tautomeric forms are intended to be encompassed by the scope of the invention, even though only one tautomeric structure is depicted. For example, any claim to compound having the structure A below is understood to include tautomeric structure B, and vice versa, as well as mixtures thereof.

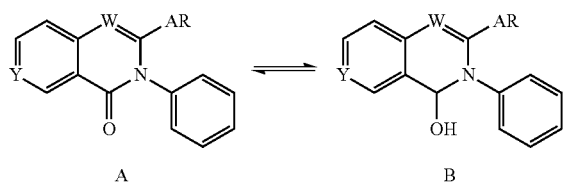

EXEMPLARY EMBODIMENTS

Formula I Compounds

In certain embodiments, Y is carbon and W is nitrogen in compounds of Formula I.

In certain embodiments, $R_{a_6}$ in Formula I is fluoride, hydrogen, $C_1$-$C_3$ alkoxy, or $SO_2R_3$, wherein $R_3$ is selected from $C_1$-$C_3$ alkyl and cyclopropyl.

In other embodiments, $R_{a_6}$ in Formula I is selected from fluoride, hydrogen, methoxy, and $SO_2Me$.

In some embodiments, $R_{a_7}$ in Formula I is hydrogen, fluoride, or $SO_2R_3$, wherein $R_3$ is selected from $C_1$-$C_3$ alkyl and cyclopropy.

In other embodiments, $R_{a_7}$ in Formula I is hydrogen, fluoride, or $SO_2Me$.

In some embodiments, $R_{a_8}$ in Formula I is hydrogen, methoxy, or chloride.

In some embodiments, n is 1 in compounds of Formula I.
In some embodiments, D is O in compounds of Formula I.
In certain embodiments, $R_{b_3}$ and $R_{b_5}$ in Formula I are independently selected from hydrogen and methyl.

In certain embodiments, $R_{c_3}$ in Formula I is hydrogen.
In certain embodiments, $R_{c_5}$ is hydrogen in compounds of Formula I.

In some embodiments, $R_{c_3}$ and $R_{c_5}$ in Formula I are both hydrogen.

In some compounds of Formula I, $R_{c_4}$ is selected from F, Cl, Br, I, $CF_3$, $C_1$-$C_6$ alkyl, cyclohexyl, —NHC(O)$R_4$, —NHSO$_2R_4$, —C(O)OR$_4$, and

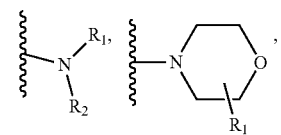

wherein
$R_4$ is selected from hydrogen, $C_1$-$C_4$ alkyl, and aryl; and
$R_1$ and $R_2$ are independently selected from hydrogen and $C_1$-$C_3$ alkyl.

In other compounds of Formula I, $R_{c_4}$ is selected from F, Cl, Br, I, $CF_3$, sec-butyl, isopropyl, tert-butyl, cyclohexyl, —NHC(O)$R_4$, NHSO$_2R_4$, C(O)OR$_4$, and

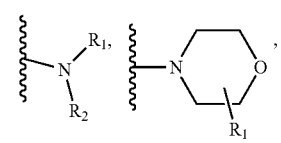

wherein
$R_4$ is selected from hydrogen, $C_1$-$C_4$ alkyl, and aryl; and
$R_1$ and $R_2$ are independently selected from hydrogen and $C_1$-$C_3$ alkyl.

In still other embodiments, $R_{c_4}$ in Formula I is selected from F, Cl, Br, I, CF$_3$, sec-butyl, isopropyl, tert-butyl, cyclohexyl, NHC(O)H, NHC(O)Me, —NHC(O)CH(CH$_3$)$_2$, NHSO$_2$Me, —NHSO$_2$-phenyl, —NHSO$_2$CH(CH$_3$)$_2$, C(O)OMe, NMe$_2$, and morpholinyl.

In another embodiment, $R_{c_4}$ in Formula I is sec-butyl.

In some embodiments, $R_1$, $R'_1$, $R_2$ and $R'_2$ in Formula I are each hydrogen.

In certain embodiments of the invention, the compound of Formula I is selected from the group consisting of:
3-(4-sec-butylphenyl)-2-(4-(2-hydroxyethoxy)-3,5-dimethylphenyl)quinazolin-4(3H)-one,
3-(4-sec-butylphenyl)-2-(4-(2-hydroxyethoxy)phenyl) quinazolin-4(3H)-one;
3-(4-fluorophenyl)-2-(4-(2-hydroxyethoxy)-3,5-dimethylphenyl)quinazolin-4(3H)-one;
2-(4-(2-hydroxyethoxy)-3,5-dimethylphenyl)-3-(4-iodophenyl)quinazolin-4(3H)-one;
3-(4-bromophenyl)-2-(4-(2-hydroxyethoxy)-3,5-dimethylphenyl)quinazolin-4(3H)-one;
3-(4-sec-butylphenyl)-6-fluoro-2-(4-(2-hydroxyethoxy)-3,5-dimethylphenyl)quinazolin-4(3H)-one;
3-(4-chlorophenyl)-2-(4-(2-hydroxyethoxy)-3,5-dimethylphenyl)quinazolin-4(3H)-one,
3-(4-sec-butylphenyl)-7-fluoro-2-(4-(2-hydroxyethoxy)-3,5-dimethylphenyl)quinazolin-4(3H)-one;
2-(4-(2-hydroxyethoxy)-3,5-dimethylphenyl)-3-(4-(trifluoromethyl)phenyl)quinazolin-4(3H)-one;
3-(4-sec-butylphenyl)-2-(4-(2-hydroxyethoxy)-3,5-dimethylphenyl)-7-(methylsulfonyl)quinazolin-4(3H)-one;
3-(4-sec-butylphenyl)-2-(4-(2-hydroxyethoxy)-3,5-dimethylphenyl)-6-methoxyquinazolin-4(3H)-one;
3-(4-sec-butylphenyl)-2-(4-(2-hydroxyethoxy)-3,5-dimethylphenyl)-8-methoxyquinazolin-4(3H)-one;
3-(4-sec-butylphenyl)-2-(4-(2-hydroxyethoxy)-3,5-dimethylphenyl)pyrido[4,3-d]pyrimidin-4(3H)-one;
3-(4-sec-butylphenyl)-2-(4-(2-hydroxyethoxy)-3,5-dimethylphenyl)-6-(methylsulfonyl)quinazolin-4(3H)-one;
3-(4-bromophenyl)-2-(4-(2-hydroxyethoxy)-3,5-dimethylphenyl)-6-methoxyquinazolin-4(3H)-one;
3-(4-bromophenyl)-2-(4-(2-hydroxyethoxy)-3,5-dimethylphenyl)-8-methoxyquinazolin-4(3H)-one,
2-(4-(2-hydroxyethoxy)-3,5-dimethylphenyl)-3-(4-isopropylphenyl)quinazolin-4(3H)-one;
3-(4-bromophenyl)-2-(4-(2-hydroxyethoxy)-3-methylphenyl)quinazolin-4(3H)-one;
3-(4-bromophenyl)-8-chloro-2-(4-(2-hydroxyethoxy)-3,5-dimethylphenyl)quinazolin-4(3H)-one;
2-(4-(2-hydroxyethoxy)-3,5-dimethylphenyl)-3-(4-morpholinophenyl)quinazolin-4(3H)-one;
3-(4-tert-butylphenyl)-2-(4-(2-hydroxyethoxy)-3,5-dimethylphenyl)quinazolin-4(3H)-one;
N-(4-(2-(4-(2-hydroxyethoxy)-3,5-dimethylphenyl)-4-oxoquinazolin-3(4H)-yl)phenyl)acetamide;
N-(4-(2-(4-(2-hydroxyethoxy)-3,5-dimethylphenyl)-4-oxoquinazolin-3(4H)-yl)phenyl)isobutyramide;
Methyl 4-(2-(4-(2-hydroxyethoxy)-3,5-dimethylphenyl)-4-oxoquinazolin-3(4H)-yl)benzoate;
3-(4-cyclohexylphenyl)-2-(4-(2-hydroxyethoxy)-3,5-dimethylphenyl)quinazolin-4(3H)-one;
N-(4-(2-(4-(2-hydroxyethoxy)-3,5-dimethylphenyl)-4-oxoquinazolin-3(4H)-yl)phenyl)formamide;
3-(4-aminophenyl)-2-(4-(2-hydroxyethoxy)-3,5-dimethylphenyl)quinazolin-4(3H)-one;
N-(4-(2-(4-(2-hydroxyethoxy)-3,5-dimethylphenyl)-4-oxoquinazolin-3(4H)-yl)phenyl)methanesulfonamide;
N-(4-(2-(4-(2-hydroxyethoxy)-3,5-dimethylphenyl)-4-oxoquinazolin-3(4H)-yl)phenyl)benzenesulfonamide;
N-(4-(2-(4-(2-hydroxyethoxy)-3,5-dimethylphenyl)-4-oxoquinazolin-3(4H)-yl)phenyl)propane-2-sulfonamide;
3-(4-(dimethylamino)phenyl)-2-(4-(2-hydroxyethoxy)-3,5-dimethylphenyl)quinazolin-4(3H)-one;
3-(4-sec-butylphenyl)-2-(4-(2-hydroxyethoxy)-3-methylphenyl)quinazolin-4(3H)-one; and
3-(4-chlorophenyl)-2-(4-(2-hydroxyethoxy)-3-methylphenyl)quinazolin-4(3H)-one, and tautomers, stereoisomers, pharmaceutically acceptable salts and hydrates thereof.

Formula II Compounds

In some embodiments, W is nitrogen in compounds of Formula II.

In some embodiments, T is carbon in compounds of in Formula II.

In some embodiments, $R_{a_5}$ in Formula II is hydrogen.

In some embodiments, $R_{a_7}$ is hydrogen in compounds of Formula II.

In some embodiments, $R_{a_5}$, $R_{a_7}$, and $R_{a_8}$ in Formula II are each hydrogen.

In some embodiments, $R_{b_4}$ in Formula II is selected from hydrogen, Cl, Br, F, CF$_3$, methyl, methoxy, -Ophenyl, phenyl, CH$_2$OH, —CH$_2$morpholino, morpholino, and piperidinyl.

In some embodiments, $R_{b_5}$ in Formula II is hydrogen, Br, NEt$_2$, or phenyl.

In some embodiments, $R_{b_4}$ and $R_{b_5}$ together to which the atoms they are bound form a phenyl ring in compounds of Formula II.

In some embodiments, $R_{c_4}$ in Formula II is Cl, sec-butyl, isopropyl, cyclopropyl, cylcopentyl, SMe, NHSO$_2$Me, or NMe$_2$ In some embodiments, $R_{c_4}$ in Formula II is sec-butyl.

In certain embodiments of the invention, the compound of Formula II is selected from the group consisting of:
3-(4-sec-butylphenyl)-2-(pyridin-3-yl)quinazolin-4(3H)-one;
3-(4-chlorophenyl)-2-(quinolin-3-yl)quinazolin-4(3H)-one;
3-(4-sec-butylphenyl)-2-(5-fluoropyridin-3-yl)quinazolin-4(3H)-one;
3-(4-chlorophenyl)-2-(6-chloropyridin-3-yl)quinazolin-4(3H)-one;
3-(4-sec-butylphenyl)-2-(6-chloropyridin-3-yl)quinazolin-4(3H)-one;
3-(4-sec-butylphenyl)-2-(6-methoxypyridin-3-yl)quinazolin-4(3H)-one;
2-(6-bromopyridin-3-yl)-3-(4-chlorophenyl)quinazolin-4(3H)-one;
2-(6-bromopyridin-3-yl)-3-(4-sec-butylphenyl)quinazolin-4(3H)-one;
3-(4-chlorophenyl)-2-(6-(diethylamino)pyridin-3-yl) quinazolin-4(3H)-one;
3-(4-sec-butylphenyl)-2-(6-(diethylamino)pyridin-3-yl) quinazolin-4(3H)-one;
3-(4-sec-butylphenyl)-2-(pyrimidin-5-yl)quinazolin-4(3H)-one;
3-(4-sec-butylphenyl)-2-(6-methylpyridin-3-yl)quinazolin-4(3H)-one;
3-(4-chlorophenyl)-2-(6-methylpyridin-3-yl)quinazolin-4(3H)-one;
3-(4-chlorophenyl)-2-(6-(piperidin-1-yl)pyridin-3-yl) quinazolin-4(3H)-one;
3-(4-sec-butylphenyl)-2-(6-(piperidin-1-yl)pyridin-3-yl) quinazolin-4(3H)-one;
3-(4-chlorophenyl)-2-(6-phenoxypyridin-3-yl)quinazolin-4(3H)-one;

3-(4-sec-butylphenyl)-2-(6-fluoropyridin-3-yl)quinazolin-4 (3H)-one;
3-(4-sec-butylphenyl)-2-(6-phenoxypyridin-3-yl)quinazolin-4(3H)-one;
3-(4-chlorophenyl)-2-(6-(trifluoromethyl)pyridin-3-yl) quinazolin-4(3H)-one,
3-(4-sec-butylphenyl)-2-(6-(trifluoromethyl)pyridin-3-yl) quinazolin-4(3H)-one;
3-(4-sec-butylphenyl)-2-(6-phenylpyridin-3-yl)quinazolin-4 (3H)-one;
3-(4-sec-butylphenyl)-2-(5-phenylpyridin-3-yl)quinazolin-4 (3H)-one;
2-(5-bromopyridin-3-yl)-3-(4-sec-butylphenyl)quinazolin-4 (3H)-one;
2-(5-bromopyridin-3-yl)-3-(4-chlorophenyl)quinazolin-4 (3H)-one;
3-(4-sec-butylphenyl)-2-(5-(diethylamino)pyridin-3-yl) quinazolin-4(3H)-one;
3-(4-chlorophenyl)-2-(5-phenylpyridin-3-yl)quinazolin-4 (3H)-one;
3-(4-chlorophenyl)-2-(5-(diethylamino)pyridin-3-yl) quinazolin-4(3H)-one;
3-(4-cyclopentylphenyl)-2-(6-methylpyridin-3-yl)quinazolin-4(3H)-one;
3-(4-sec-butylphenyl)-2-(6-(hydroxymethyl)pyridin-3-yl) quinazolin-4(3H)-one;
2-(6-methylpyridin-3-yl)-3-(4-(methylthio)phenyl)quinazolin-4(3H)-one;
3-(4-isopropylphenyl)-2-(6-methylpyridin-3-yl)quinazolin-4(3H)-one;
N-(4-(2-(6-methylpyridin-3-yl)-4-oxoquinazolin-3(4H)-yl) phenyl)methanesulfonamide;
3-(4-sec-butylphenyl)-2-(6-(morpholinomethyl)pyridin-3-yl)quinazolin-4(3H)-one;
3-(4-cyclopropylphenyl)-2-(6-methylpyridin-3-yl)quinazolin-4(3H)-one;
3-(4-(dimethylamino)phenyl)-2-(6-methylpyridin-3-yl) quinazolin-4(3H)-one;
2-(6-chloropyridin-3-yl)-3-(4-cyclopropylphenyl)quinazolin-4(3H)-one; and
3-(4-sec-butylphenyl)-2-(6-morpholinopyridin-3-yl) quinazolin-4(3H)-one, and tautomers, stereoisomers, pharmaceutically acceptable salts, and hydrates thereof.

Formula III Compounds

In some embodiments, $R_{b_2}$ and $R_{b_3}$ in Formula III are each hydrogen.

In some embodiments, T is nitrogen and U and V are both carbon in compounds of Formula III.

In other embodiments, T is carbon and U and V are both carbon in compounds of Formula III.

In still other embodiments, T is carbon, U is carbon, and V is nitrogen in compounds of Formula III.

In some embodiments, $R_1$ in Formula III is hydrogen, methyl, or $SO_2R_3$, wherein $R_3$ is aryl optionally substituted with methoxy or fluoride.

In some embodiments, $R_2$ in Formula III is hydrogen or $CH_2OH$.

In some embodiments, AR in Formula III is selected from 1H-indazol-5-yl, 1H-indol-4-yl, 1H-indol-5-yl, 1H-indol-6-yl, 1H-indol-7-yl, 2-(hydroxymethyl)-1H-benzo[d]imidazol-6-yl, 1-(4-fluorophenylsulfonyl)-1H-pyrrolo[2,3-b]pyridin-5-yl, 1-(phenylsulfonyl)-1H-pyrrolo[2,3-b]pyridin-5-yl, 2-(hydroxymethyl)-1H-indol-5-yl, and 1-methyl-1H-indol-5-yl.

In some embodiments, $R_{a_5}$, $R_{a_6}$, $R_{a_7}$, and $R_{a_8}$ in Formula III are each hydrogen.

In some embodiments, $R_{b_2}$ and $R_{b_3}$ in Formula III are both hydrogen.

In some embodiments, $R_{c_4}$ in Formula III is sec-butyl, isopropyl, cyclopentyl, Cl, $OCF_3$, or $NMe_2$.

In certain embodiments, $R_{c_4}$ in Formula III is sec-butyl and Cl.

In certain embodiments of the invention, the compound of Formula III is selected from the group consisting of:
3-(4-sec-butylphenyl)-2-(1H-indazol-5-yl)quinazolin-4 (3H)-one;
3-(4-chlorophenyl)-2-(1H-indol-5-yl)quinazolin-4(3H)-one;
3-(4-sec-butylphenyl)-2-(1H-indol-5-yl)quinazolin-4(3H)-one;
3-(4-sec-butylphenyl)-2-(2-(hydroxymethyl)-1H-benzo[d] imidazol-6-yl)quinazolin-4(3H)-one,
2-(1H-indol-5-yl)-3-(4-(trifluoromethoxy)phenyl)quinazolin-4(3H)-one;
2-(1H-indol-5-yl)-3-(4-isopropylphenyl)quinazolin-4(3H)-one,
3-(4-chlorophenyl)-2-(1-(4-methoxyphenylsulfonyl)-1H-pyrrolo[2,3-b]pyridin-5-yl)quinazolin-4(3H)-one;
3-(4-chlorophenyl)-2-(1-(4-fluorophenylsulfonyl)-1H-pyrrolo[2,3-b]pyridin-5-yl)quinazolin-4(3H)-one;
3-(4-(dimethylamino)phenyl)-2-(1H-indol-5-yl)quinazolin-4(3H)-one;
3-(4-chlorophenyl)-2-(1-(phenylsulfonyl)-1H-pyrrolo[2,3-b]pyridin-5-yl)quinazolin-4(3H)-one;
3-(4-sec-butylphenyl)-2-(2-(hydroxymethyl)-1H-indol-5-yl) quinazolin-4(3H)-one;
3-(4-chlorophenyl)-2-(1-methyl-1H-indol-5-yl)quinazolin-4 (3H)-one;
3-(4-cyclopentylphenyl)-2-(1H-indol-5-yl)quinazolin-4 (3H)-one;
3-(4-chlorophenyl)-2-(1H-indol-6-yl)quinazolin-4(3H)-one;
3-(4-chlorophenyl)-2-(1H-indol-7-yl)quinazolin-4(3H)-one;
3-(4-sec-butylphenyl)-2-(1H-indol-6-yl)quinazolin-4(3H)-one;
3-(4-sec-butylphenyl)-2-(1H-indol-7-yl)quinazolin-4(3H)-one;
3-(4-chlorophenyl)-2-(1H-indol-4-yl)quinazolin-4(3H)-one; and
3-(4-sec-butylphenyl)-2-(1H-indol-4-yl)quinazolin-4(3H)-one, and tautomers, stereoisomers, pharmaceutically acceptable salts, and hydrates thereof.

Any one or more of the compounds of Formula I, II, III, and tautomers, stereoisomers, and pharmaceutically acceptable salts thereof may be used in the methods of the invention, e.g., methods of increasing the expression of ApoA-I and/or HDL-C in a subject, methods of altering lipid metabolism in a subject, and methods of treating and/or preventing cardiovascular, cholesterol-, or lipid related disorders. Any one or more of the exemplified compounds of Formula I, II, and III or their tautomers, stereoisomers, pharmaceutically acceptable salts or hydrates may be employed in the methods of the invention.

Pharmaceutical Compositions

Pharmaceutical compositions of the invention comprise at least one compound of Formula I, II, III, or tautomer, stereoisomer, pharmaceutically acceptable salt or hydrate thereof formulated together with one or more pharmaceutically acceptable carriers. These formulations include those suitable for oral, rectal, topical, buccal and parenteral (e.g. subcutaneous, intramuscular, intradermal, or intravenous) administration. The most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of a compound of the invention as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association at least one compound of the invention as the active compound and a carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with at least one compound as described herein as the active compound in a unit-dose formulation, for example, a tablet, which may contain from about 0.05% to about 95% by weight of the at least one active compound. Other pharmacologically active substances may also be present including other compounds. The formulations of the invention may be prepared by any of the well known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared, for example by dissolving or dispersing at least one active compound of the invention as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the at least one active compound of the invention with a liquid or finely divided solid carrier, or both, and then, if necessary, shaping the product. For example, a tablet may be prepared by compressing or molding a powder or granules of the compound of the invention, which may optionally be combined with one or more accessory ingredients. Compressed tablets may be prepared by compressing, in a suitable machine, the compound of the invention in a free-flowing form, such as a powder or granules, which may optionally be mixed with a binder, lubricant, inert diluent and/or surface active/dispersing agent(s). Molded tablets may be made by molding, in a suitable machine, where the powdered form of the compound of the invention moistened with an inert liquid diluent.

Formulations suitable for buccal (sub-lingual) administration include lozenges comprising a compound of the invention as described herein in a flavored base, usually sucrose and acacia or tragacanth, and pastilles comprising the compound in an inert base such as gelatin and glycerin or sucrose and acacia.

Formulations of the invention suitable for parenteral administration comprise sterile aqueous preparations of at least one compound of Formula I, II, III, tautomers, stereoisomers, pharmaceutically acceptable salts and hydrates thereof, which are approximately isotonic with the blood of the intended recipient. These preparations are administered intravenously, although administration may also be effected by means of subcutaneous, intramuscular, or intradermal injection. Such preparations may conveniently be prepared by admixing the compound with water and rendering the resulting solution sterile and isotonic with the blood. Injectable compositions according to the invention may contain from about 0.1 to about 5% w/w of the active compound.

Formulations suitable for rectal administration are presented as unit-dose suppositories. These may be prepared by admixing the compound with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include petroleum jelly, such as Vaseline®, lanoline, polyethylene glycols, alcohols, and combinations of two or more thereof. The active compound (i.e., one or more compounds of Formula I, II, III, tautomers, stereoisomers, pharmaceutically acceptable salts, and hydrates thereof) is generally present at a concentration of from about 0.1% to about 15% w/w of the composition, for example, from about 0.5% to about 2%.

The amount of active compound administered may be dependent on the subject being treated, the subject's weight, the manner of administration, and the judgment of the prescribing physician. For example, a dosing schedule may involve the daily or semi-daily administration of the encapsulated compound at a perceived dosage of about 1 µg to about 1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a compound of the invention is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50(4): 219-244 (1966) and Table 1 for Equivalent Surface Area Dosage Factors).

TABLE 1

Equivalent Surface Area Dosage Factors

| From: | To: Mouse (20 g) | Rat (150 g) | Monkey (3.5 kg) | Dog (8 kg) | Human (60 kg) |
|---|---|---|---|---|---|
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 3/5 | 1 | 1/2 |
| Human | 12 | 7 | 3 | 2 | 1 |

The dosage of suitable compounds for use in the methods of the invention lies preferably within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and sex, as well as the severity of the medical condition in the subject. The dosage may be determined by a physician and adjusted, as necessary, to suit observed effects of the treatment.

In one embodiment, a compound of Formula I, II, III, or a tautomer, stereoisomer, pharmaceutically acceptable salt or hydrate thereof, is administered in combination with another therapeutic agent. The other therapeutic agent can provide additive or synergistic value relative to the administration of a compound of the invention alone. The therapeutic agent can be, for example, a statin; a PPAR agonist, e.g., a thiazolidinedione or fibrate; a niacin, a RVX, FXR or LXR agonist; a bile-acid reuptake inhibitor; a cholesterol absorption inhibitor; a cholesterol synthesis inhibitor; a cholesteryl ester transfer protein (CETP), an ion-exchange resin; an antioxidant; an inhibitor of AcylCoA cholesterol acyltransferase (ACAT inhibitor); a tyrophostine; a sulfonylurea-based drug; a biguanide; an alpha-glucosidase inhibitor; an apolipoprotein E regulator; a HMG-CoA reductase inhibitor, a microsomal triglyceride transfer protein; an LDL-lowing drug; an HDL-raising drug; an HDL enhancer; a regulator of the apolipoprotein A-IV and/or apolipoprotein genes; or any cardiovascular drug.

Therapeutic Methods

In one embodiment of the invention, a method of treating or preventing cardiovascular disease, cholesterol-, or lipid-related disorders, comprises administering to a subject (e.g., a mammal, such as e.g., a human) a therapeutically effective amount of at least one compound of the invention, i.e., a compound of Formula I, II, III, or a tautomer, stereoisomer, pharmaceutically acceptable salt or hydrate thereof. In another embodiment, at least one compound of the invention may be administered as a pharmaceutically acceptable composition, comprising one or more compounds of the invention and a pharmaceutically acceptable carrier.

The compounds and compositions of the invention may also be used in methods for altering lipid metabolism in a subject; for example, increasing the ratio of LDL to HDL or ApoB to ApoA-I in the blood of a subject. Such methods comprise administering to the subject a composition of the invention in an amount effective to alter lipid metabolism.

Another embodiment of the invention is a method for elevating levels of ApoA-I-associated molecules, such as HDL, in the blood of a subject, wherein the method comprises administering to the subject a compound or composition of the invention in an amount effective to elevate levels of ApoA-I- and HDL-associated proteins in the subject.

In some embodiments, the methods of the invention comprise administering at least one compound of the invention to a subject, such as a human, as a preventative measure against cardiovascular diseases, including cholesterol- or lipid-related disorders. For example, one or more compounds of the invention may be administered to a subject to prevent the development of arteriosclerosis lesions In other embodiments, a method for regressing arteriosclerosis lesions comprises administering at least one compound of the invention to a subject in need thereof.

In one embodiment, at least one compound of the invention is administered as a preventative measure to a subject, such as a human, having a genetic predisposition to a cardiovascular disease, including cholesterol- or lipid-related disorders, for example familial hypercholesterolemia, familial combined hyperlipidemia, atherosclerosis, a dyslipidemia, a dyslipoproteinemia, or Alzheimer's disease.

In another embodiment, at least one compound of the invention or a composition comprising one or more compounds of the invention is administered as a preventative measure to a patient having a non-genetic predisposition to a cardiovascular disease, including cholesterol- or lipid-related disorders. Examples of such non-genetic predispositions include, but are not limited to, cardiac bypass surgery and percutaneous transluminal coronary angioplasty, which often leads to restenosis, an accelerated form of atherosclerosis; diabetes in women, which often leads to polycystic ovarian disease; and cardiovascular disease, which often leads to impotence.

Angioplasty and open heart surgery, such as coronary bypass surgery, may be required to treat cardiovascular diseases, such as atherosclerosis. These surgical procedures entail using invasive surgical devices and/or implants, and are associated with a high risk of restenosis and thrombosis. Accordingly, the compounds of the invention may be used as coatings on surgical devices (e.g., catheters) and implants (e.g., stents) to reduce the risk of restenosis and thrombosis associated with invasive procedures used in the treatment of cardiovascular diseases.

In another embodiment, the compounds of the invention may be used for the prevention of one disease or disorder while concurrently treating another (e.g., prevention of polycystic ovarian disease while treating diabetes; prevention of impotence while treating a cardiovascular disease).

EXAMPLES

The invention is further illustrated by the following non-limiting examples, wherein the following abbreviations have the following meanings. If an abbreviation is not defined, it has its generally accepted meaning.

AcOH=acetic acid
Boc=N-tert-butylcarbonyl
TBDMS=tert-butyldimethylsilyl
DMAP=dimethylaminopyridine
DMF=dimethylformamide
DMSO=dimethylsulfoxide
EtOH=ethanol
EtOAc=ethyl acetate
MeOH=methanol
THF=tetrahydrofuran
TEA=triethylamine
p-TSA=p-toluenesulfonic acid
TBAF=tetrabutylammonium fluoride
DMA=N,N-dimethylacetamide
DIBAL-H=diisobutylaluminum hydride
TPAP=tetrapropylammonium perruthenate NMO=N-methylmorpholine N-oxide
DDQ=2,3-dicyano-5,6-dichloro-parabenzoquinone
DME=1,2-dimethoxyethane
TFA=trifluoroacetic acid
DPPF=1,1'-bis(diphenylphosphino)ferrocene
Pd(OAc)$_2$=palladium(II) acetate
Pd(PPh$_3$)$_4$=tetrakis(triphenylphosphine)palladium(0)

Example 1

Preparation of 3-(4-sec-butylphenyl)-2-(4-(2-hydroxyethoxy)-3,5-dimethylphenyl)quinazolin-4(3H)-one (E)

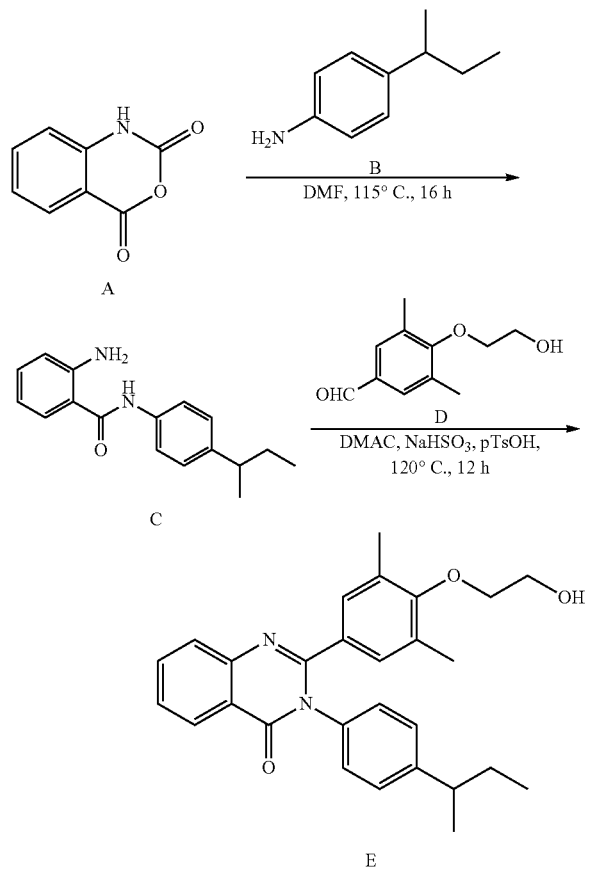

4-sec-butyl aniline (B) (1.49 g, 10.0 mmol) was added to a solution of isatoic anhydride (A) (1.63 g, 10.0 mmol) in anhydrous DMF (40 mL) and the reaction mixture was stirred at 115° C. for 16 hours under nitrogen. It was then cooled to room temperature and poured into water (200 mL), and extracted with ethyl acetate (200 mL). The organic phase was washed with water (100 mL), 10% aqueous NaOH solution (100 mL), water (100 mL) and dried over anhydrous Na$_2$SO$_4$. Removal of solvent gave 2-amino-N-(4-sec-butylphenyl)benzamide (C) as a brown solid. Yield: 1.27 g (47%).

To a solution of 2-amino-N-(4-sec-butylphenyl)benzamide (1.27 g, 4.73 mmol) in N,N-dimethyl acetamide (20 mL) were added 4-(2-hydroxy-ethoxy)-3,5-dimethyl-benzaldehyde (D) (0.92 g, 4.7 mmol), sodium hydrogen sulphite (58.5 wt %) (0.95 g, 5.2 mmol) and p-toluenesulfonic acid (0.18 g, 0.95 mmol). The reaction mixture was stirred at 120° C. overnight, and cooled to room temperature. The solvent was removed under reduced pressure and water (100 mL) was added. The mixture was extracted with ethyl acetate (200 mL). The organic phase was washed with water (2×100 mL), then brine (100 mL), and dried over anhydrous Na$_2$SO$_4$. Removal of solvent gave crude compound, which was purified by the Simpliflash system (30% ethyl acetate in hexanes as eluent) to give the title compound (E) as a white solid. Yield: 0.34 g (16%). MP 152-153° C. $^1$H-NMR (400 MHz, CDCl$_3$): δ 8.36-8.34 (m, 1H), 7.81-7.80 (m, 2H), 7.54-7.50 (m, 1H), 7.13 (d, J=6.26 Hz, 2H), 7.06 (d, J=8.21 Hz, 2H), 6.98 (s, 2H), 3.92-3.88 (m, 2H), 3.78-3.76 (m, 2H), 2.56-2.54 (m, 1H), 2.13 (s, 6H), 2.06 (t, J=6.26 Hz, 1H), 1.60-1.48 (m, 2H), 1.20 (d, J=7.04 Hz, 3H), 0.727 (t, J=7.43 Hz, 3H). MS (ES$^+$) m/z: 443.01 (M+1) (100%).

Example 2

Alternative preparation of 3-(4-sec-butylphenyl)-2-(4-(2-hydroxyethoxy)-3,5-dimethylphenyl)quinazolin-4(3H)-one (E)

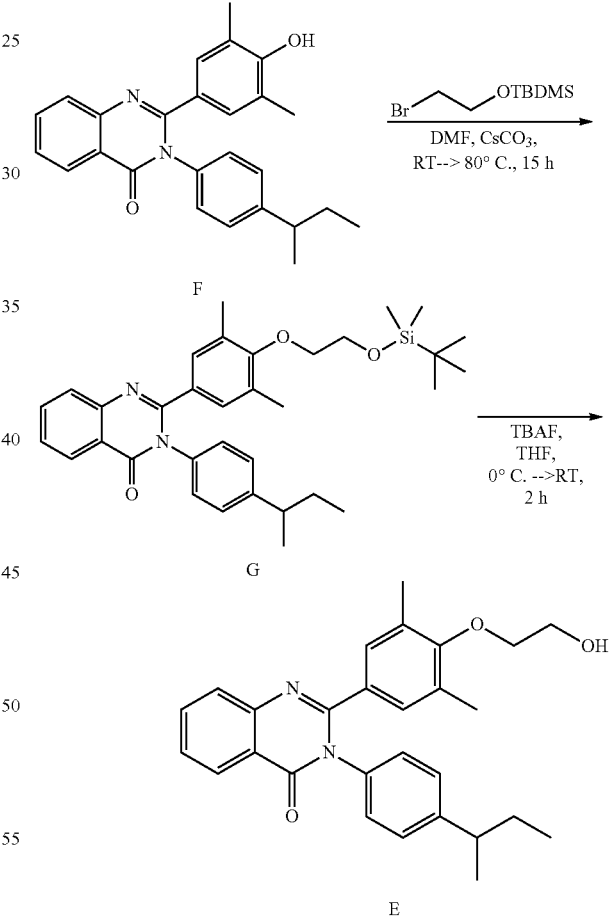

Following the method described in Example 1,3-(4-sec-butylphenyl)-2-(4-hydroxy-3,5-dimethylphenyl)quinazolin-4(3H)-one (F) was prepared in similar fashion except 4-hydroxy-3,5-dimethylbenzaldehyde was used.

To a solution of 3-(4-sec-butylphenyl)-2-(4-hydroxy-3,5-dimethylphenyl)quinazolin-4(3H)-one in anhydrous DMF were added cesium carbonate and (2-bromo-ethoxy)-tert-butyl-dimethyl-silane at room temperature. The reaction mixture was stirred at 80° C. under nitrogen for 15 hours. The reaction mixture was cooled to room temperature and compound 2-(4-(2-(tert-butyldimethylsilyloxy)ethoxy)-3,5-dimethylphenyl)-3-(4-sec-butylphenyl)quinazolin-4(3H)-one (G) was isolated and optionally purified.

A 1 M solution of tetrabutyl ammonium fluoride in THF was added to a solution of 2-(4-(2-(tert-butyldimethylsilyloxy)ethoxy)-3,5-dimethylphenyl)-3-(4-sec-butylphenyl)quinazolin-4(3H)-one in THF at 0° C. The ice bath was removed, and stirring was continued at room temperature for 2 hours. The solvent was evaporated, and residue was taken in dichloromethane, concentrated and purified as described in Example 1 to give the title compound.

Example 3

Preparation of 3-(4-bromophenyl)-2-(4-(2-hydroxyethoxy)-3,5-dimethylphenyl)quinazolin-4(3H)-one (K)

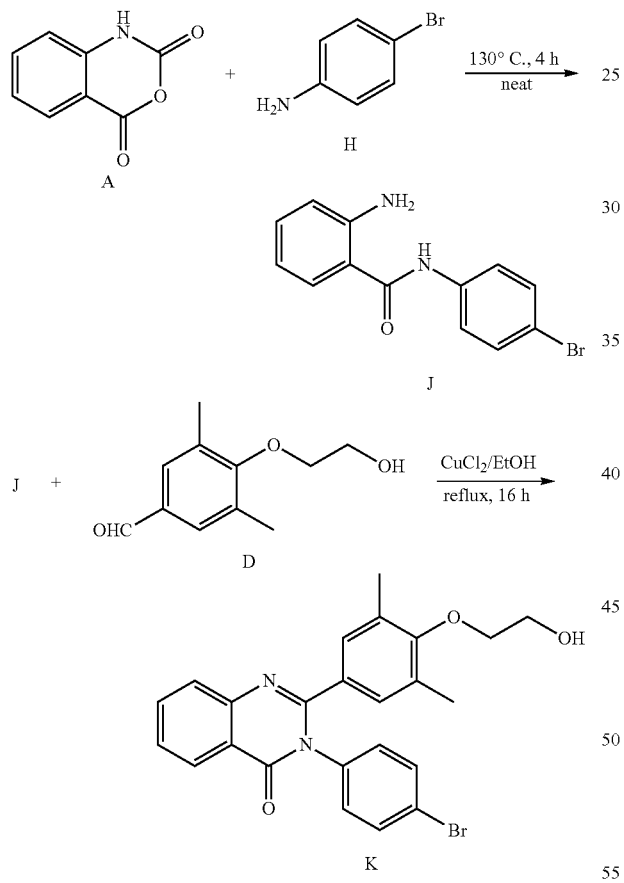

1H-Benzo[d][1,3]oxazine-2,4-dione (A) (3.26 g, 20.0 mmol) and 4-bromo-aniline (H) (3.23 g, 18.8 mmol) were mixed together as a neat mixture (both solids), and the reaction mixture was stirred at 130° C. for 4 hours, and then cooled to room temperature. The crude compound was purified by the Simpliflash system (20% ethyl acetate in hexanes as eluent) to give 2-amino-N-(4-bromo-phenyl)-benzamide (J) as white solid. Yield: 4.35 g (75%).

To a solution of 2-amino-N-(4-bromo-phenyl)-benzamide (3.75 g, 12.9 mmol) and 4-(2-hydroxy-ethoxy)-3,5-dimethylbenzaldehyde (D) (2.50 g, 12.9 mmol) in anhydrous ethanol (75 mL) was added anhydrous copper (II) chloride (5.19 g, 38.6 mmol). The reaction mixture was stirred under reflux for 16 hours under nitrogen, then cooled to room temperature. The ethanol was evaporated under reduced pressure. The residue was taken in dichloromethane (300 mL) and the organic phase was washed with water (200 mL). The aqueous phase was then extracted with $CH_2Cl_2$ (2×200 mL). The combined organic phase was washed with brine (200 mL) and dried over anhydrous $Na_2SO_4$. The solvent was evaporated. The crude compound was purified by column chromatography (silica gel 230-400 mesh; 30-50% ethyl acetate in hexanes as eluent) to give the title compound (K) as white solid. Yield: 3.84 g (64%). MP 164-165° C. $^1$H-NMR (400 MHz, DMSO-$d_6$): δ 8.33 (d, J=7.80 Hz, 1H), 7.82-7.80 (m, 2H), 7.55-7.45 (m, 3H), 7.04 (d, J=8.58 Hz, 2H), 6.98 (s, 2H), 3.94-3.90 (m, 2H), 3.82 (t, J=4.68 Hz, 2H), 2.17 (s, 6H), 2.13 (t, J=3.51 Hz, 1H). MS (ES$^+$) m/z: 465.42 (97%) (M+1), 467.43 (100%) (M+3).

Example 4

Preparation of 3-(4-sec-butylphenyl)-7-fluoro-2-(4-(2-hydroxyethoxy)-3,5-dimethylphenyl)quinazolin-4(3H)-one (Q)

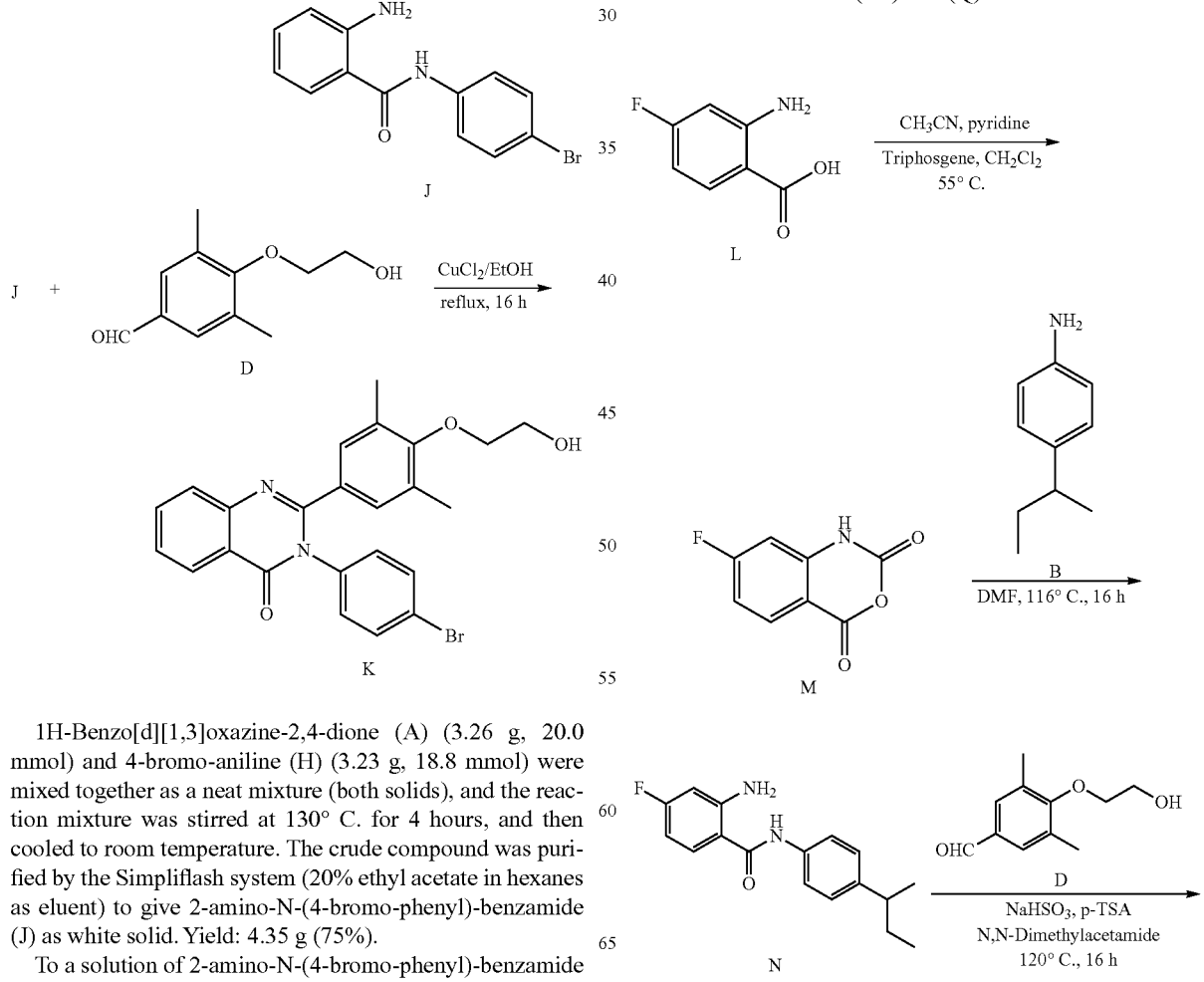

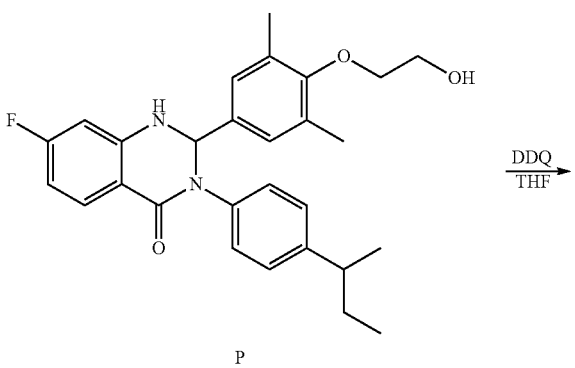

P

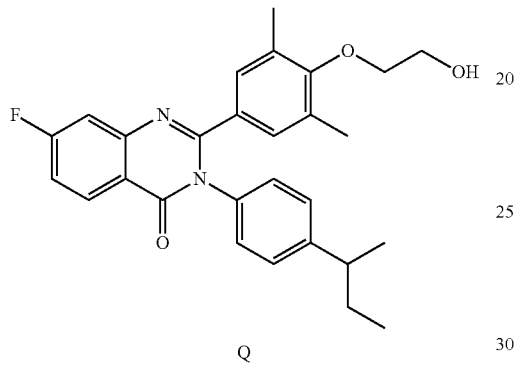

Q

To a stirred solution of 2-amino-4-fluoro benzoic acid (L) (1.15 g, 7.40 mmol) in anhydrous acetonitrile (8 mL) at 55° C. were simultaneously added anhydrous pyridine (1.2 mL, 15 mmol) and a solution of triphosgene (0.73 g, 2.5 mmol) in anhydrous $CH_2Cl_2$ (5 mL) via syringe over a period of 15-20 minutes. After the addition was completed, the reaction mixture was stirred at 55° C. for another 2 hours. Much solid precipitated out. The solvent was distilled off. After cooling down to room temperature, water was added and the solid was filtered off, washed with water, followed by chilled $CH_2Cl_2$. The solid was dried under vacuum to give 7-fluoro-1H-benzo[d][1,3]oxazine-2,4-dione (M) as grayish solid. Yield: 1.02 g (76%).

To a solution of 7-fluoro-1H-benzo[d][1,3]oxazine-2,4-dione (1.00 g, 5.52 mmol) in anhydrous DMF (15 mL), 4-(sec-butyl)-aniline (B) (0.824 g, 5.52 mmol) was added and the reaction mixture was heated at 116° C. for 16 hours. The product was extracted with ethyl acetate and washed with brine. The solvent was evaporated in vacuo to leave a crude material which was purified by column chromatography (silica gel; 230-400 mesh; ethyl acetate/hexane=1:9) to give 2-amino-N-(4-sec-butyl-phenyl)-4-fluoro-benzamide (N) as white solid. Yield: 0.92 g (58%).

A mixture of 2-amino-N-(4-sec-butyl-phenyl)-4-fluoro-benzamide (0.920 g, 3.21 mmol), 3,5-dimethyl-4-(2-hydroxy-ethoxy)-benzaldehyde (0.627 g, 3.21 mmol), sodium bisulfite (0.640 g, 3.53 mmol), and p-toluenesulfonic acid (60 mg, 0.32 mmol) in N,N-dimethylacetamide (20 mL) was heated at 120° C. for 16 hours. The solvent was evaporated in vacuo and water was added to the flask. The precipitate was filtered off and washed with water. The solid was triturated with ether and filtered off to give 3-(4-sec-butyl-phenyl)-7-fluoro-2-[4-(2-hydroxy-ethoxy)-3,5-dimethyl-phenyl]-2,3-dihydro-1H-quinazolin-4-one (P) (0.11 g). The filtrate was evaporated under vacuum to give second crop of (1.02 g). The combined yield: 1.13 g (quantitative).

To a solution of 3-(4-sec-butyl-phenyl)-7-fluoro-2-[4-(2-hydroxy-ethoxy)-3,5-dimethyl-phenyl]-2,3-dihydro-1H-quinazolin-4-one (0.11 g, 0.24 mmol) in anhydrous THF (30 mL) was added DDQ (0.09 g, 0.4 mmol) and the reaction mixture was stirred for 72 hours at room temperature. The solvent was evaporated in vacuo and the crude material was purified by column chromatography (silica gel; 230-400 mesh; 0.5% methanol/$CH_2Cl_2$ as eluent) to give the title compound (Q) as white solid. Yield: 0.06 g (50%). MP 53.9-54.4° C. $^1$H-NMR (400 MHz, $CDCl_3$): δ 8.38 (dd, 1H), 7.43 (dd, 1H), 7.22-7.05 (m, 5H), 6.99 (s, 2H), 3.90 (m, 2H), 3.78 (m, 2H), 2.59 (m, 1H), 2.16 (s, 6H), 2.05 (t, 1H), 1.59 (m, 2H), 1.20 (d, 3H), 0.71 (t, 3H).

Example 5

Preparation of 3-(4-sec-butylphenyl)-2-(4-(2-hydroxyethoxy)-3,5-dimethylphenyl)pyrido[4,3-d]pyrimidin-4(3H)-one (11)

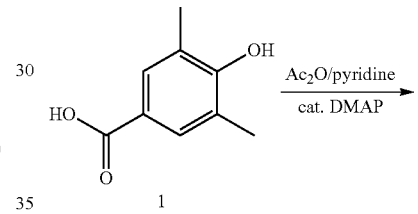

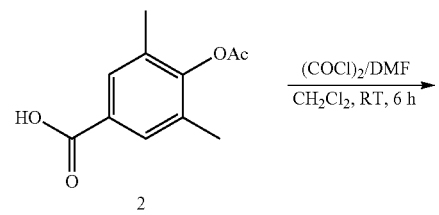

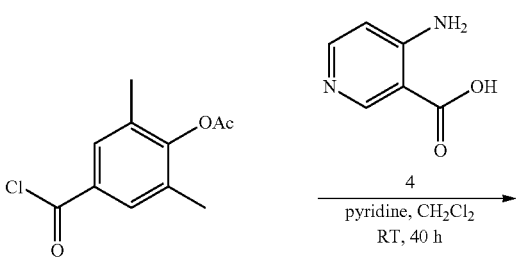

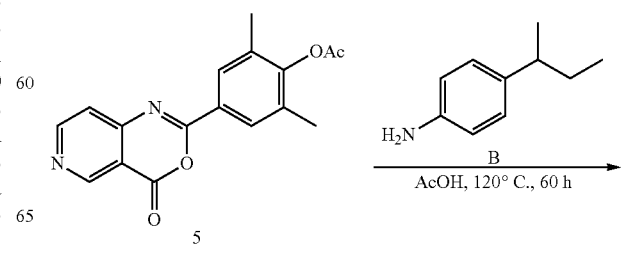

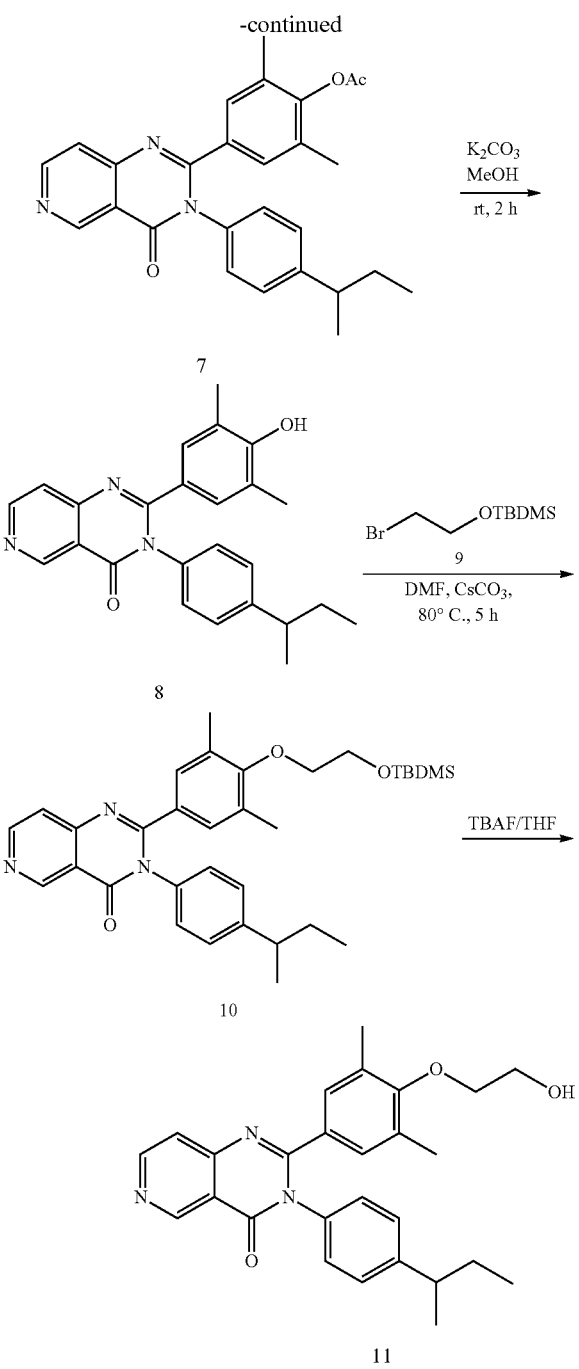

To a solution of 4-hydroxy-3,5-dimethyl-benzoic acid (1) (5.41 g, 32.5 mmol) in anhydrous pyridine (50 mL) were added acetic anhydride and 4-dimethylaminopyridine (0.1 g, 0.8 mmol). The reaction mixture was stirred at room temperature for 16 hours. Pyridine was evaporated under reduced pressure. The residue was taken in ethyl acetate (300 mL). The organic phase was washed with 2 N aq. HCl (100 mL), water (2×100 mL), brine (100 mL) and dried over anhydrous $Na_2SO_4$. Solvent was evaporated to give 4-acetoxy-3,5-dimethylbenzoic acid (2) as an off-white solid. Yield: 6.65 g (98%).

To a solution of 4-acetoxy-3,5-dimethylbenzoic acid (2.08 g, 10.0 mmol) in anhydrous dichloromethane (40 mL) were sequentially added oxalyl chloride (3.81 g, 30.0 mmol) and anhydrous DMF (5 drops). The reaction mixture was stirred at room temperature for 6 hours. Solvent and excess oxalyl chloride were evaporated under reduced pressure and the residue was dried under vacuum to give acetic acid 4-chlorocarbonyl-2,6-dimethylphenyl ester (3) as an orange solid. Yield: 2.32 g (100%).

To a solution of acetic acid 4-chlorocarbonyl-2,6-dimethylphenyl ester (2.32 g, 10.0 mmol) in anhydrous $CH_2Cl_2$ (30 mL) were added 4-amino-nicotinic acid (4) (1.10 g, 8.00 mmol) and pyridine (2.37 g, 30.0 mmol). The reaction mixture was stirred at room temperature under nitrogen for 40 hours. Solvent was evaporated. The residue was diluted with methanol (20 mL). The solid separated was filtered, washed with methanol (2×10 mL) and dried under vacuum to give acetic acid 2,6-dimethyl-4-(4-oxo-4H-pyrido[4,3-d][1,3]oxazin-2-yl)-phenyl ester (6) as yellow solid. Yield: 1.99 g (64%).

To a solution of acetic acid 2,6-dimethyl-4-(4-oxo-4H-pyrido[4,3-d][1,3]oxazin-2-yl)-phenyl ester (1.04 g, 3.35 mmol) in glacial acetic acid (20 mL) was added 4-(sec-butyl)-aniline (B) (0.750 g, 5.02 mmol). The reaction mixture was stirred at 120° C. for 60 hours under nitrogen and cooled to room temperature. Acetic acid was removed under reduced pressure. The residue was diluted with water (100 mL), neutralized to pH 7 with saturated aqueous $NaHCO_3$ solution, and extracted with ethyl acetate (200 mL). The organic phase was washed with water (100 mL), then brine (100 mL), and dried over anhydrous $Na_2SO_4$. Solvent was evaporated and the crude compound was purified by column chromatography (silica gel 230-400 mesh; 20-30% ethyl acetate in hexanes as eluent) to give acetic acid 4-[3-(4-sec-butyl-phenyl)-4-oxo-3,4-dihydro-pyrido[4,3,d]pyrimidin-2-yl]-2,6-dimethyl-phenyl ester (7) as a white solid. Yield: 0.580 g (39%).

To a solution of acetic acid 4-[3-(4-sec-butyl-phenyl)-4-oxo-3,4-dihydro-pyrido[4,3,d]pyrimidin-2-yl]-2,6-dimethyl-phenyl ester (0.580 g, 1.31 mmol) in methanol (20 mL) was added potassium carbonate (0.55 g, 3.94 mmol). The color changed to yellow. The reaction mixture was stirred at room temperature for 2 hours. Methanol was evaporated. The residue was diluted with water (100 mL), and neutralized to pH 5 with glacial acetic acid. The white precipitate formed was filtered, washed with water and ethyl acetate (20 mL) and dried under vacuum to give 3-(4-sec-butyl-phenyl)-2-(4-hydroxy-3,5-dimethyl-phenyl)-3H-pyrido[4,3-d]pyrimidin-4-one (8) as a white solid. Yield: 0.25 g (48%).

To a solution of 3-(4-sec-butyl-phenyl)-2-(4-hydroxy-3,5-dimethyl-phenyl)-3H-pyrido[4,3-d]pyrimidin-4-one (0.25 g, 0.63 mmol) in anhydrous DMF (10 mL) was added cesium carbonate (0.62 g, 1.9 mmol). The color changed to orange. The reaction mixture was stirred at room temperature for 10 minutes under nitrogen. Then, (2-bromo-ethoxy)-tert-butyl-dimethyl-silane (9) (0.300 g, 1.27 mmol) was added and the reaction mixture was stirred at 80° C. for 5 hours under nitrogen, cooled to room temperature, diluted with water (100 mL), and extracted with ethyl acetate (100 mL). The organic phase was washed with water (2×50 mL), then brine (50 mL), and dried over anhydrous $Na_2SO_4$. The solvent was evaporated. The crude compound was purified by the Simpliflash system (30% ethyl acetate in hexanes as eluent) to give 2-{4-[2-(tert-butyl-dimethyl-silanyloxy)-ethoxy]-3,5-dimethyl-phenyl}-3-(4-sec-butyl-phenyl)-3H-pyrido[4,3-d]pyrimidin-4-one (10) as a gummy solid. Yield: 0.20 g (58%).

To a solution of 2-{4-[2-(tert-butyl-dimethyl-silanyloxy)-ethoxy]-3,5-dimethyl-phenyl}-3-(4-sec-butyl-phenyl)-3H-pyrido[4,3-c]pyrimidin-4-one (0.20 g, 0.36 mmol) in anhydrous THF (3 mL) was added 1.0 M solution of tetrabutylammonium fluoride in THF (0.72 mL, 0.72 mmol).

The reaction mixture was stirred under nitrogen for 1 hour at room temperature. Solvent was evaporated, the residue was taken in ethyl acetate (50 mL). The organic phase was washed with water (20 mL), brine (20 mL) and dried over anhydrous $Na_2SO_4$. Solvent was evaporated and the crude compound was purified by the Simpliflash system (0-3% MeOH in $CH_2Cl_2$ as eluent), to give the title compound (II) as a white solid. Yield: 0.09 g (56%). MP 195-196° C. $^1$H-NMR (400 MHz, $CDCl_3$): δ 9.56 (s, 1H), 8.88 (d, J=5.60 Hz, 1H), 7.61 (d, J=6.00 Hz, 1H), 7.15 (d, J=7.20 Hz, 2H), 7.05 (d, J=8.80 Hz, 2H), 7.00 (s, 2H), 3.93-3.89 (m, 2H), 3.80-3.78 (m, 2H), 2.62-2.56 (m, 1H), 2.14 (s, 6H), 2.07 (t, J=6.40 Hz, 1H), 1.61-1.22 (m, 2H), 1.20 (d, J=7.20 Hz, 3H), 0.74 (t, J=7.20 Hz, 3H). MS (ES$^+$) m/z: 444.31 (M+1).

Example 6

Preparation of 3-(4-sec-butylphenyl)-2-(4-(2-hydroxyethoxy)phenyl)quinazolin-4(3H)-one

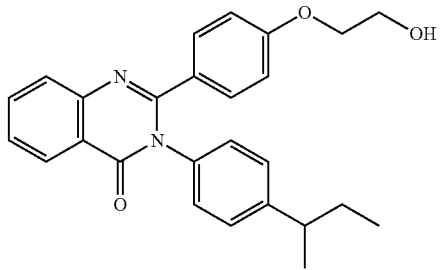 [SMILES: CCC(C)c1ccc(-n2c(-c3ccc(OCCO)cc3)nc3ccccc3c2=O)cc1]

To a solution of isatoic anhydride (4.00 g, 24.0 mmol) in N,N-dimethyl formamide (80 mL) under nitrogen atmosphere was added 4-sec-butylaniline (3.66 g, 24.0 mmol). The reaction mixture was heated at 80° C. for 24 hours, then the solvent was removed under reduced pressure and the residue was diluted with ethyl acetate, washed with 1 N aqueous solution of sodium hydroxide, water, and dried over sodium sulfate. The crude oil (7 g) was purified by column chromatography (silica gel 230-400 mesh; 10/0 to 4/1 hexanes/EtOAc as eluent) to give pure 2-amino-N-(4-sec-butylphenyl)-benzamide as a brown solid. Yield: 1.8 g (27.3%).

To a solution of 2-amino-N-(4-sec-butylphenyl)-benzamide (0.500 g, 1.86 mmol) in N,N-dimethylformamide (9 mL) under nitrogen atmosphere was added 4-hydroxy-benzaldehyde (0.450 g, 3.73 mmol) followed by iodine (0.560 g, 2.23 mmol) and potassium hydroxide (0.120 g, 2.23 mmol). The resulting mixture was heated at 110° C. overnight, then the solvent was removed under reduced pressure, the residue was diluted with ethyl acetate, washed with water and dried over sodium sulfate. The crude oil (0.97 g) was purified by column chromatography (silica gel 230-400 mesh; 1/1 hexanes/EtOAc as eluent) to give pure 3-(4-sec-butylphenyl)-2-(4-hydroxyphenyl)-3H-quinazolin-4-one as a yellow solid. Yield: 0.33 g (47.8%). To a mixture of 3-(4-sec-butylphenyl)-2-(4-hydroxyphenyl)-3H-quinazolin-4-one (0.11 g, 0.31 mmol) and potassium carbonate (0.13 g, 0.93 mmol) in N,N-dimethylformamide (3.5 mL) under nitrogen atmosphere was added 2-chloroethanol (0.032 mL, 46 mmol). The reaction mixture was heated at reflux for 14 hours, then the solvent was removed under reduced pressure and the residue was diluted with ethyl acetate, washed with 5% aqueous solution of sodium hydroxide, brine, and dried over sodium sulfate. The crude solid (0.13 g) was purified by column chromatography (silica gel 230-400 mesh; 10/0 to 1/1 hexanes/EtOAc, then 10/0 to 9.4/0.6 methylene chloride/MeOH as eluent) and triturated with $Et_2O$ to give the pure title compound as a light brown solid. Yield: 60 mg, (46.3%). MP 172.8-174.9° C. $^1$H-NMR (400 MHz, $CDCl_3$): δ 8.35 (d, 1H), 7.80 (d, 2H), 7.50 (m, 1H), 7.28 (d, 2H), 7.14 (d, 2H), 7.05 (d, 2H), 6.72 (d, 2H), 4.00 (m, 2H), 3.95 (m, 2H), 2.58 (m, 1H), 1.95 (s, OH), 1.65-1.48 (m, 2H), 1.20 (d, 3H), 0.75 (t, 3H). MS (ES$^+$) m/z: 415.09 (M+1).

Example 7

Preparation of 3-(4-fluorophenyl)-2-(4-(2-hydroxyethoxy)-3,5-dimethylphenyl)quinazolin-4(3H)-one

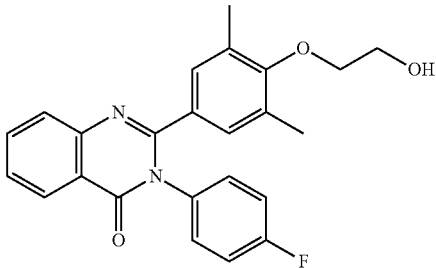

To a solution of 4-fluoroaniline (2.40 mL, 24.5 mmol) in N,N-dimethylformamide (30 mL) was added isatoic anhydride (4.00 g, 24.5 mmol), and the reaction mixture was heated at 115° C. for 14 hours. The reaction mixture was cooled to room temperature and diluted with ethyl acetate (100 mL). The organic layer was washed with 1 N NaOH (200 mL), water (100 mL), then brine, and dried over $Na_2SO_4$. The solvent was removed under reduced pressure to give crude product, which was purified by column chromatography (silica gel 230-400 mesh; 10% EtOAc/hexane as eluent) to give 2-amino-N-(4-fluoro-phenyl)-benzamide as white solid. Yield: 2.00 g (35%).

To a mixture of 4-(2-hydroxy-ethoxy)-3,5-dimethyl-benzaldehyde (0.420 g, 2.17 mmol) and 2-amino-N-(4-fluorophenyl)-benzamide (0.500 g, 2.17 mmol) in N,N-dimethylacetamide (5 mL) was added sodium hydrogen sulfite (0.350 g, 3.26 mmol) and p-toluenesulfonic acid (0.21 g, 0.11 mmol). The reaction mixture was heated at 155° C. for 14 hours. The reaction mixture was cooled to room temperature and diluted with cold water (20 mL) to produce the precipitate. The yellow solid was filtered, washed with cold water (2×20 mL), methanol, and dried under vacuum to provide crude product, which was purified by column chromatography (silica gel 230-400 mesh; 10% EtOAc/hexane as eluent) to give the title compound as white solid. Yield: 0.10 g (11%). MP 95-97° C. $^1$H-NMR (400 MHz, $CDCl_3$): δ 8.35 (d, 1H), 7.81-7.78 (d, 2H), 7.58-7.40 (m, 1H), 7.20-7.15 (m, 2H), 7.15-7.01 (m, 4H), 3.98-3.80 (m, 4H), 2.21 (s, 6H), 2.01 (t, 1H). MS (ES$^+$) m/z: 405.01 (M+1).

Example 8

Preparation of 2-(4-(2-hydroxyethoxy)-3,5-dimethylphenyl)-3-(4-iodophenyl)quinazolin-4(3H)-one

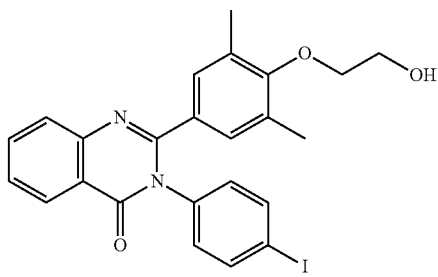 [SMILES: Cc1cc(-c2nc3ccccc3c(=O)n2-c2ccc(I)cc2)cc(C)c1OCCO]

To a solution of 4-iodoaniline (4.03 g, 18.4 mmol) in N,N-dimethylformamide (20 mL) was added isatoic anhydride (3.00 g, 18.4 mmol), and the reaction mixture was heated at 115° C. for 14 hours. The reaction mixture was cooled to room temperature and diluted with ethyl acetate (100 mL). The organic layer was washed with 1 N NaOH (200 mL), water (100 mL), then brine, and dried over $Na_2SO_4$. The solvent was removed under reduced pressure to give crude product, which was purified by column chromatography (silica gel 230-400 mesh; 10% EtOAc/hexane as eluent) to give 2-amino-N-(4-iodo-phenyl)-benzamide as white solid. Yield: 1.50 g (24%).

To a mixture of 4-(2-hydroxy-ethoxy)-3,5-dimethyl-benzaldehyde (0.570 g, 2.96 mmol) and 2-amino-N-(4-iodo-phenyl)-benzamide (1.00 g, 2.96 mmol) in N,N-dimethylacetamide (10 mL) was added sodium hydrogen sulfite (0.470 g, 4.44 mmol) and p-toluenesulfonic acid (0.280 g, 1.48 mmol). The reaction mixture was heated at 155° C. for 14 hours. The reaction mixture was cooled to room temperature and diluted with cold water (20 mL) to produce the precipitate. The yellow solid was filtered, washed with cold water (2×20 mL), methanol and dried under vacuum to provide crude product, which was purified by column chromatography (silica gel 230-400 mesh; 10% EtOAc/hexane as eluent) to give the title compound as white solid. Yield: 0.20 g (13%). MP 101-103° C. $^1$H-NMR (400 MHz, CDCl$_3$): δ 8.38 (d, 1H), 7.81-7.78 (m, 2H), 7.75 (d, 2H), 7.59-7.48 (m, 1H), 7.01-6.85 (m, 4H), 3.98-3.81 (m, 4H), 2.40 (s, 6H), 2.01 (t, 1H). MS (ES$^+$) m/z: 513.09 (M+1).

Example 9

Preparation of 3-(4-sec-butylphenyl)-6-fluoro-2-(4-(2-hydroxyethoxy)-3,5-dimethylphenyl)quinazolin-4(3H)-one

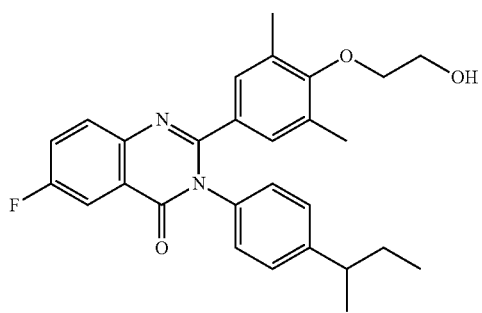 [SMILES: CCC(C)c1ccc(-n2c(-c3cc(C)c(OCCO)c(C)c3)nc3ccc(F)cc3c2=O)cc1]

To a solution of 2-amino-5-fluorobenzoic acid (1.00 g, 6.40 mmol) in acetonitrile (8 mL) was added a solution of triphosgene (0.64 g, 2.1 mmol) in dichloromethane (5 mL) and pyridine (1.1 mL, 13.0 mmol) simultaneously within 5 min. The resulting pale yellow suspension was heated at 55° C. for 2 hours. The solvents were evaporated under vacuum, and the residue was stirred with water (5 mL). The precipitate obtained was filtered and dried to afford 6-fluoro-1H-benzo[d][1,3]oxazine-2,4-dione. Yield: 1.06 g (91%).

To a suspension 6-fluoro-1H-benzo[d][1,3]oxazine-2,4-dione (1.06 g, 5.90 mmol) in DMF (5 mL) was added 4-sec-butylphenylamine (1.95 mL, 11.8 mmol) at room temperature. The suspension was heated at 70° C. for 2 days, and cooled to room temperature. The reaction mixture was poured into crushed ice (150 mL), and extracted with dichloromethane. The organic layer was dried over $Na_2SO_4$, and evaporated under vacuum. The residue was purified by flash column chromatography on a Biotage (40 M silica column), using a gradient of hexane:ethyl acetate (9:1 to 8:2) mixture as eluent to afford 2-amino-N-(4-sec-butylphenyl)-5-fluorobenzamide. Yield: 1.16 g (69%).

Anhydrous CuCl$_2$ (0.21 g, 1.6 mmol) was added to a solution of 2-amino-N-(4-sec-butylphenyl)-5-fluorobenzamide (0.15 g, 0.52 mmol), and 4-(2-hydroxyethoxy)-3,5-dimethylbenzaldehyde (0.12 g, 0.63 mmol) in ethanol (30 mL). The resulting green solution was heated at reflux for 3 hours. After cooling to room temperature, the mixture was concentrated under vacuum. The residue was stirred with water (20 mL), and extracted with ethyl acetate (2×25 mL). The organic layer was separated, washed with brine, and dried over $Na_2SO_4$. The solvent was evaporated under vacuum, and the residue was purified by flash column chromatography on a Biotage (25 M silica column) using a gradient of hexane:ethyl acetate (8:2 to 5:5) mixture as eluent to afford the title compound. Yield: 0.19 g (77%). MP 70-72° C. $^1$H-NMR (400 MHz, CDCl$_3$): δ 7.99 (m, 1H), 7.82 (m, 1H), 7.53 (m, 1H), 7.15 (m, 2H), 7.09 (d, 2H), 6.97 (s, 2H), 3.91 (m, 2H), 3.78 (m, 2H), 2.59 (m, 1H), 2.15 (s, 6H), 2.02 (t, 1H), 1.54 (m, 2H), 1.21 (d, 2H), 0.73 (t, 3H).

Example 10

Preparation of 3-(4-chlorophenyl)-2-(4-(2-hydroxyethoxy)-3,5-dimethylphenyl)quinazolin-4(3H)-one

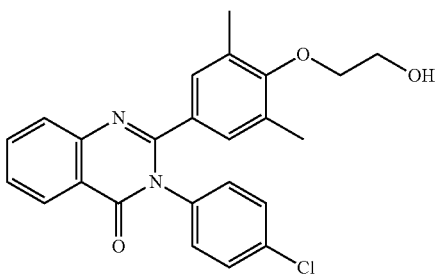 [SMILES: Cc1cc(-c2nc3ccccc3c(=O)n2-c2ccc(Cl)cc2)cc(C)c1OCCO]

To a solution of 4-chloroaniline (3.13 g, 24.5 mmol) in N,N-dimethylformide (20 mL) was added isatoic anhydride (4.00 g, 24.5 mmol), and the reaction mixture was heated at 115° C. for 14 h, cooled to room temperature and diluted with ethyl acetate (100 mL). The organic layer was washed with 1 N NaOH (200 mL), water (100 mL), then brine, and dried over $Na_2SO_4$. The solvent was removed under reduced pressure to give crude product, which was purified by column chromatography (silica gel 230-400 mesh; EtOAc/hexane=1:9) to give 2-amino-N-(4-chloro-phenyl)-benzamide as white solid. Yield: 1.67 g (28%).

To a mixture of 4-(2-hydroxyethoxy)-3,5-dimethyl-benzaldehyde (0.420 g, 2.17 mmol) and 2-amino-N-(4-chloro-phenyl)-benzamide (0.500 g, 2.17 mmol) in N,N-dimethylacetamide (5 mL) was added sodium hydrogensulfite (0.350 g, 3.26 mmol) and p-toluenesulfonic acid (0.21 g, 0.11 mmol). The reaction mixture was heated at 155° C. for 14 hours, cooled to room temperature, and diluted with cold water (20 mL), to produce the precipitate. The yellow solid was filtered, washed with cold water, then methanol, and dried under vacuum to provide crude product, which was purified by preparative HPLC (0.1% TFA in CH$_3$CN/H$_2$O as eluent) to give the title compound as a white solid. Yield: 0.23 g (14%). MP 101-103° C. $^1$H-NMR (400 MHz, CDCl$_3$): δ 8.38 (d, 1H), 7.81-7.78 (m, 2H), 7.59-7.51 (m, 1H), 7.31-7.20 (m, 2H), 7.15-7.12 (m, 2H), 7.01-6.98 (d, 2H), 3.98-3.80 (m, 4H), 2.20 (s, 6H), 2.01 (t, 1H). MS (ES$^+$) m/z: 421.05 (M+1).

Example 11

Preparation of 2-(4-(2-hydroxyethoxy)-3,5-dimethylphenyl)-3-(4-(trifluoromethyl)phenyl)quinazolin-4(3H)-one

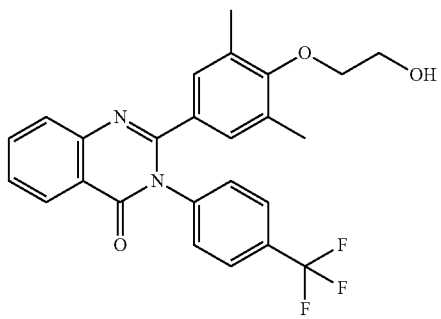 [SMILES: Cc1cc(-c2nc3ccccc3c(=O)n2-c2ccc(C(F)(F)F)cc2)cc(C)c1OCCO]

To a solution of 1H-benzo[d][1,3]oxazine-2,4-dione (1.63 g, 10.0 mmol) in anhydrous DMF (20 mL) was added 4-trifluoromethyl-aniline (1.61 g, 10.0 mmol) and the reaction mixture was stirred at 115° C. for 16 hours. It was then cooled to room temperature, diluted with ethyl acetate (150 mL), and the organic phase was washed with water (100 mL), 10% aq. NaOH solution (100 mL), water (150 mL), brine (150 mL), and dried over anhydrous Na$_2$SO$_4$. Solvent was evaporated and the crude compound was purified by the Simpliflash system (20% ethyl acetate in hexanes as eluent) to give 2-amino-N-(4-trifluoromethyl-phenyl)-benzamide as an off-white solid. Yield: 0.2 g (7%).

To a solution of 2-amino-N-(4-trifluoromethyl-phenyl)-benzamide (0.19 g, 0.68 mmol) and 4-(2-hydroxy-ethoxy)-3,5-dimethyl-benzaldehyde (0.16 g, 0.81 mmol) in anhydrous ethanol (15 mL) was added anhydrous copper (II) chloride (0.273 g, 2.03 mmol). The reaction mixture was stirred at reflux for 16 hours under nitrogen and then cooled to room temperature. Ethanol was evaporated under reduced pressure. The residue was taken in ethyl acetate (100 mL). The organic phase was washed with water (2×75 mL), then brine (75 mL), and dried over anhydrous Na$_2$SO$_4$. Solvent was evaporated; crude compound was purified by column chromatography (silica gel 230-400 mesh; 2:3:5 ethyl acetate, hexanes and CH$_2$Cl$_2$ as eluent) to give the title compound as a white solid. Yield: 0.17 g (55%). MP 160-161° C. $^1$H-NMR (400 MHz, CDCl$_3$): δ 8.34 (d, J=8.00 Hz, 1H), 7.84-7.82 (m, 2H), 7.62-7.53 (m, 3H), 7.31 (d, J=8.40 Hz, 2H), 6.97 (s, 2H), 3.93-3.89 (m, 2H), 3.80 (t, J=5.20 Hz, 2H), 2.15 (s, 6H), 2.07 (t, J=6.40 Hz, 1H).

Example 12

Preparation of 3-(4-sec-butylphenyl)-2-(4-(2-hydroxyethoxy)-3,5-dimethylphenyl)-7-(methylsulfonyl)quinazolin-4(3H)-one

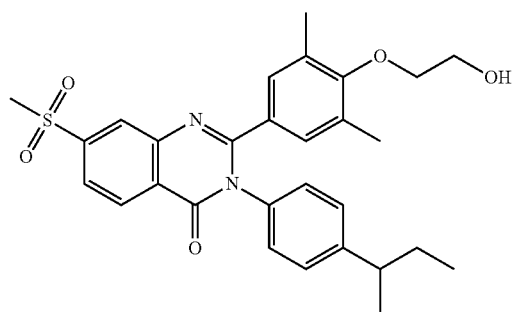 [SMILES: CCC(C)c1ccc(-n2c(-c3cc(C)c(OCCO)c(C)c3)nc3cc(S(C)(=O)=O)ccc3c2=O)cc1]

To a suspension of 2-amino-4-methanesulfonyl-benzoic acid (1.00 g, 4.64 mmol) in acetonitrile (15 mL) at 55° C. were simultaneously added pyridine (0.75 mL, 9.3 mmol) and a solution of triphosgene (0.455 g, 1.53 mmol) in dichloromethane (5 mL). The resulting mixture was stirred at 55° C. for 2 hours and the solvent was removed using a rotary evaporator. The residue was diluted with water (50 mL) and the precipitate was filtered, and air dried to provide 7-methanesulfonyl-1H-benzo[d][1,3]oxazine-2,4-dione. Yield: 0.98 g (82%).

A solution of 7-methanesulfonyl-1H-benzo[d][1,3]oxazine-2,4-dione (0.98 g, 3.8 mmol) and 4-sec-butylaniline (0.57 g, 3.8 mmol) in N,N-dimethylformamide (30 mL) was stirred at 115° C. for 16 hours, cooled to room temperature, diluted with water (50 mL), extracted with ethyl acetate (2×100 mL), and concentrated using a rotary evaporator. The residue was further purified by column chromatography (SiO$_2$, hexane/ethyl acetate=2:1) to provide 2-amino-N-(4-sec-butyl-phenyl)-4-methanesulfonyl-benzamide. Yield: 0.466 g (33%).

To a solution of 2-amino-N-(4-sec-butyl-phenyl)-4-methanesulfonyl-benzamide (0.20 g, 0.55 mmol) and 4-(2-hydroxy-ethoxy)-3,5-dimethyl-benzaldehyde (0.13 g, 0.66 mmol) in ethanol (15 mL) was added anhydrous copper (II) chloride (0.222 g, 1.65 mmol). The resulting mixture was stirred at reflux for 24 hours and the solvent was removed using a rotary evaporator. The residue was then diluted with water (50 mL), extracted with ethyl acetate (2×100 mL), and concentrated on using a rotary evaporator. The crude product was made into a slurry in diethyl ether (20 mL) and filtered to provide the title compound as white solid. Yield: 0.20 g (70%). MP 235-237° C. $^1$H-NMR (400 MHz, CDCl$_3$): δ 8.53 (d, 1H), 8.41 (d, 1H), 8.00 (dd, 1H), 7.16 (d, 2H), 7.06 (d, 2H), 7.00 (s, 2H), 3.91 (m, 2H), 3.80 (m, 2H), 3.15 (s, 3H), 2.59 (m, 1H), 2.13 (s, 6H), 2.04 (m, 1H), 1.58 (m, 2H), 1.22 (d, 3H), 0.73 (t, 3H). MS (ES$^+$) m/z: 521.22 (M+1).

Example 13

Preparation of 3-(4-sec-butylphenyl)-2-(4-(2-hydroxyethoxy)-3,5-dimethylphenyl)-6-methoxyquinazolin-4(3H)-one

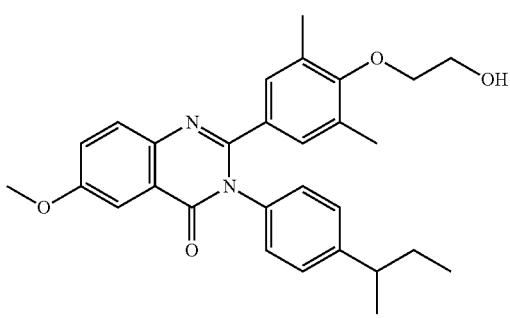 [SMILES: CCC(C)c1ccc(-n2c(-c3cc(C)c(OCCO)c(C)c3)nc3ccc(OC)cc3c2=O)cc1]

To a solution of 2-amino-5-methoxy-benzoic acid (1.50 g, 8.97 mmol) in anhydrous acetonitrile (15 mL) at 50-55° C. were simultaneously added pyridine (1.42 g, 17.9 mmol) and a solution of triphosgene (0.870 g, 2.96 mmol) in anhydrous dichloromethane (20 mL) over 20 min span, and the reaction was stirred at 50-55° C. for 2 hours. The solvent was removed and the residue was mixed with water (100 mL), the solid was filtered and rinsed with cold water (30 mL) and dried. The crude was further washed with ether (20 mL) to give 6-methoxy-1H-benzo[d][1,3]oxazine-2,4-dione. Yield: 1.55 g (89%).

To a flask (100 mL) with magnetic stirrer was added 6-methoxy-1H-benzo[d][1,3]oxazine-2,4-dione (1.55 g, 8.00 mmol), 4-sec-butylaniline (1.19 mL, 8.0 mmol) and anhydrous DMF (10 mL). The reaction mixture was stirred at 115° C. for 16 hours under nitrogen. DMF was removed and the residue was mixed with water (100 mL) and ethyl acetate (150 mL). The organic phase was separated and washed with brine (50 mL). The solvent was removed and the residue was purified by column chromatography on silica gel (230-400 mesh) using hexane/ethyl acetate=1:1 to give 2-amino-N-(4-sec-butyl-phenyl)-5-methoxy-benzamide. Yield: 0.90 g (37%).

To a solution of 2-amino-N-(4-sec-butyl-phenyl)-5-methoxy-benzamide (0.450 g, 1.51 mmol) and 4-(2-hydroxy-ethoxy)-3,5-dimethyl-benzaldehyde (0.290 g, 1.51 mmol) in anhydrous ethanol (20 mL) was added anhydrous copper (II) chloride (0.610 g, 4.53 mmol). The reaction mixture was stirred at reflux for 4 hours under nitrogen. The solvent was removed and the residue was diluted with dichloromethane (100 mL) and water (100 mL). After separation, the organic phase was further washed with water (100 mL), then brine (100 mL), and dried over sodium sulfate. The crude product was purified by column chromatography on silica gel (230-400 mesh) using hexane/ethyl acetate=1:1 to give the title compound as white solid. Yield: 260 mg (36%). MP 152-154° C. $^1$H-NMR (400 Hz, CDCl$_3$): δ 7.78 (d, 1H), 7.74 (s, 1H), 7.40 (m, 1H), 7.14 (m, 2H), 7.08 (m, 2H), 6.94 (s, 2H), 3.96 (s, 3H), 3.90 (m, 2H), 3.78 (t, 2H), 2.56 (m, 1H), 2.12 (s, 6H), 2.08 (t, 1H), 1.60 (m, 1H), 1.50 (m, 2H), 1.20 (d, 3H), 0.72 (t, 3H). MS (ES$^+$) m/z: 473.29 (M+1).

Example 14

Preparation of 3-(4-sec-butylphenyl)-2-(4-(2-hydroxyethoxy)-3,5-dimethylphenyl)-8-methoxyquinazolin-4(3H)-one

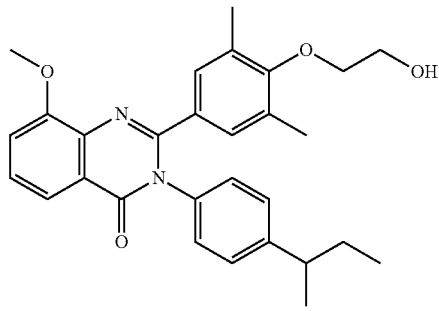 [SMILES: CCC(C)c1ccc(-n2c(-c3cc(C)c(OCCO)c(C)c3)nc3c(OC)cccc3c2=O)cc1]

A solution of 8-methoxy-1H-benzo[d][1,3]oxazine-2,4-dione (0.50 g, 2.6 mmol) and 4-sec-butylaniline (0.42 g, 2.8 mmol) in DMF (4.0 mL) were stirred at 110° C. under N$_2$ for 24 hours. The mixture was concentrated to dryness then purified by column chromatography on silica gel using ½ EtOAc/hexane as eluent to afford 2-amino-N-(4-sec-butyl-phenyl)-3-methoxy-benzamide as white solid. Yield: 0.533 g (69%).

To a 100-mL round bottom flask were added 2-amino-N-(4-sec-butyl-phenyl)-3-methoxy-benzamide (0.533 g, 1.79 mmol), 4-(2-hydroxy-ethoxy)-3,5-dimethyl-benzaldehyde (0.382 g, 1.96 mmol), anhydrous copper (II) chloride (0.722 g, 5.37 mmol), and anhydrous ethanol (40 mL). The mixture was refluxed at 100° C. under N$_2$ for 5 hours. The mixture was concentrated to dryness. Water (approximately 20 mL) was added and extracted with EtOAc (3×50 mL). The EtOAc solutions were combined and dried over Na$_2$SO$_4$. The crude product was purified by column chromatography on silica gel using hexane/EtOAc (1:1 to 1:2) as eluent. The product fractions were concentrated to dryness then re-crystallized in ether to afford the title compound as white solid. Yield: 0.460 g (54%). MP 158-159° C. $^1$H-NMR (400 MHz, CDCl$_3$): δ 7.93 (d, 1H), 7.46 (t, 1H), 7.24 (d, 1H), 7.12 (d, 2H), 7.05 (d, 2H), 7.00 (s, 2H), 4.03 (s, 3H), 3.89 (m, 2H), 3.75 (m, 2H), 2.56 (m, 1H), 2.11 (s, 6H), 1.52 (m, 2H), 1.19 (d, 3H), 0.72 (t, 3H). MS (ES$^+$) m/z: 473.27 (M+1).

Example 15

Preparation of 3-(4-sec-butylphenyl)-2-(4-(2-hydroxyethoxy)-3,5-dimethylphenyl)-6-(methylsulfonyl)quinazolin-4(3H)-one

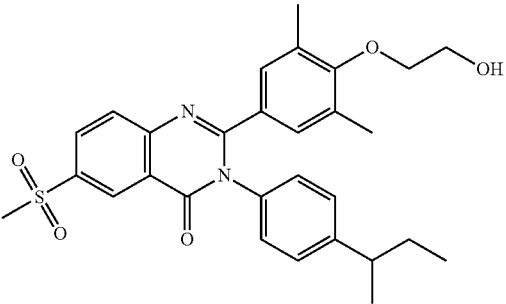 [SMILES: CCC(C)c1ccc(-n2c(-c3cc(C)c(OCCO)c(C)c3)nc3ccc(S(C)(=O)=O)cc3c2=O)cc1]

To a solution of 2-chloro-4-methylsulfonyl aniline (1.0 g, 4.9 mmol) in N-methylpyrrolidine (10 mL) was added copper (I) cyanide (4.35 g, 48.6 mmol) under nitrogen. The reaction mixture was stirred at 180° C. for 72 hours, cooled to room temperature, poured to a 1:1 mixture of ammonia and water (200 mL), stirred for 1 hour, and then filtered off. The residue was washed with $CH_2Cl_2$ (50 mL) and filtrate was extracted with $CH_2Cl_2$ (3×20 mL). The combined organic layers were backwashed with water (50 mL), dried over sodium sulfate, and concentrated to provide crude material, which was purified by flash column chromatography (silica gel; 230-400 mesh; ethyl acetate/hexanes=1:5) to obtain 2-amino-5-methanesulfonyl-benzonitrile as a white solid. Yield: 0.1 g (13%). A suspension of potassium hydroxide (2.05 g, 36.7 mmol) in ethylene glycol (9 mL) was heated to 80° C. KOH was dissolved completely at this stage. 2-Amino-5-methanesulfonyl-benzonitrile (0.900 g, 4.59 mmol) was added to the reaction mixture and the bath temperature was increased to 185° C. and stirred for 16 hours. The resultant reaction mixture was cooled to room temperature, diluted with water (20 mL), and extracted with $CH_2Cl_2$ (3×30 mL). The aqueous layer was acidified with 2 N HCl to pH 4-5, extracted with EtOAc (3×30 mL), and the combined organic layers were backwashed with water (30 mL), then brine (30 mL), dried over sodium sulfate, and evaporated, to obtain 2-amino-5-methanesulfonyl-benzoic acid. Yield: 0.750 g (75%).

To a suspension of 2-amino-5-methanesulfonyl-benzoic acid (0.750 g, 3.48 mmol) in THF (50 mL) were added 1-(3-dimethylaminopropyl)-3-ethylcarbodiimide hydrochloride (0.730 g, 3.83 mmol), 1-hydroxybenzotriazole (0.510 g, 3.83 mmol), and 4-methylmorpholine (0.380 g, 3.83 mmol). The reaction mixture was stirred at room temperature for 5 minutes and then 4-sec-butyl-aniline (0.780 g, 5.22 mmol) was added. The reaction mixture was stirred at room temperature for 16 hours. The solvent was evaporated in vacuo, water was added, and the product was extracted with ethyl acetate. The solvent was evaporated in vacuo and the residue was washed with ether to obtain 2-amino-N-(4-sec-butyl-phenyl)-5-methanesulfonyl-benzamide as white solid. Yield: 0.75 g (62%).

To a solution of 2-amino-N-(4-sec-butyl-phenyl)-5-methanesulfonyl-benzamide (0.21 g, 0.58 mmol) and 4-(2-hydroxy-ethoxy)-3,5-dimethyl-benzaldehyde (0.13 g, 0.64 mmol) in anhydrous ethanol (20 mL) was added anhydrous copper (II) chloride (0.440 g, 3.27 mmol) and the reaction mixture was refluxed for 48 hours. The solvent was evaporated in vacuo and the product was extracted with dichloromethane. The solvent was evaporated in vacuo and the residue was triturated with ether and methanol/ethyl acetate and filtered off, to obtain the title compound as a white solid. Yield: 0.13 g (43%). MP 258.8-260.2° C. $^1$H-NMR (400 MHz, $CDCl_3$): δ 8.94 (s, 1H), 8.28 (d, 1H), 7.94 (d, 1H), 7.19 (m, 2H), 7.03 (m, 2H), 7.01 (s, 2H), 3.91 (m, 2H), 3.79 (d, 2H), 3.17 (s, 3H), 2.58 (m, 1H), 2.18 (s, 3H), 2.03 (m, 1H), 1.60 (m, 2H), 1.21 (d, 3H), 0.78 (t, 3H). MS (ES$^+$) m/z: 521.66 (M+1).

Example 16

Preparation of 3-(4-bromophenyl)-2-(4-(2-hydroxy-ethoxy)-3,5-dimethylphenyl)-6-methoxyquinazolin-4(3H)-one

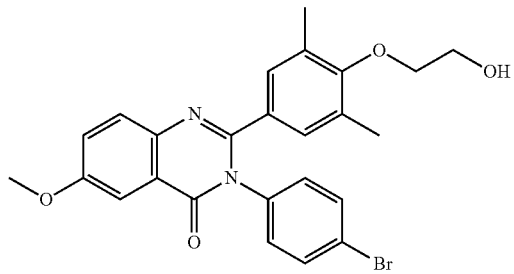 [SMILES: COc1ccc2nc(-c3cc(C)c(OCCO)c(C)c3)n(-c3ccc(Br)cc3)c(=O)c2c1]

To a solution of 2-amino-5-methoxy-benzoic acid (1.50 g, 8.97 mmol) in anhydrous acetonitrile (15 mL) at 50-55° C. were simultaneously added pyridine (1.42 g, 17.9 mmol) and a solution of triphosgene (0.870 g, 2.96 mmol) in anhydrous dichloromethane (20 mL) over 20 minute span, and the reaction was stirred at 50-55° C. for 2 hours. The solvent was removed and the residue was mixed with water (100 mL), the solid was filtered and rinsed with cold water (30 mL) and dried. The crude product was further washed with ether (20 mL) to give 6-methoxy-1H-benzo[d][1,3]oxazine-2,4-dione. Yield: 1.40 g (81%).

A solution of 6-methoxy-1H-benzo[d][1,3]oxazine-2,4-dione (0.800 g, 4.10 mmol) and 4-bromoaniline (0.750 g, 4.30 mmol) in anhydrous DMF (10 mL) was stirred at 115° C. for 16 hours under nitrogen. DMF was removed and the residue was mixed with water (100 mL) and ethyl acetate (150 mL). The organic phase was separated, backwashed with brine (50 mL), and concentrated. The residue was purified by column chromatography ($SiO_2$, hexane/ethyl acetate=1:1) to give 2-amino-N-(4-bromo-phenyl)-5-methoxy-benzamide. Yield: 0.240 g (18%).

To a solution of 2-amino-N-(4-bromo-phenyl)-5-methoxy-benzamide (0.240 g, 0.740 mmol) and 4-(2-hydroxy-ethoxy)-3,5-dimethyl-benzaldehyde (0.145 g, 0.740 mmol) in anhydrous ethanol (20 mL) was added anhydrous copper (II) chloride (0.298 g, 2.22 mmol). The reaction mixture was stirred at reflux for 4 hours under nitrogen. The solvent was removed and the residue was diluted with ethyl acetate (100 mL) and water (100 mL). After separation the organic phase was further backwashed with water (100 mL), brine (100 mL), dried over sodium sulfate, and concentrated. The crude was purified by column chromatography ($SiO_2$, hexane/ethyl acetate=1:1) to give the title compound as white solid. Yield: 120 mg (33%). MP 160-162° C. $^1$H-NMR (400 Hz, $CDCl_3$): δ 7.74 (d, 1H), 7.69 (s, 1H), 7.46 (d, 2H), 7.40 (m, 1H), 7.03 (d, 2H), 6.96 (s, 2H), 3.94 (s, 3H), 3.91 (m, 2H), 3.82 (t, 2H), 2.17 (s, 6H), 2.05 (t, 1H). MS (ES$^+$) m/z: 497.41 (M+1).

Example 17

Preparation of 3-(4-bromophenyl)-2-(4-(2-hydroxy-ethoxy)-3,5-dimethylphenyl)-8-methoxyquinazolin-4(3H)-one

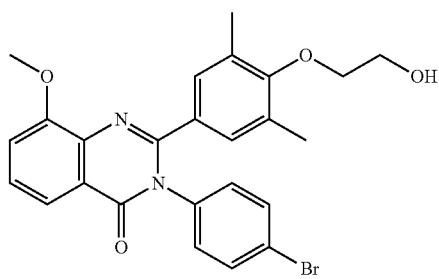 [SMILES: COc1cccc2c(=O)n(-c3ccc(Br)cc3)c(-c3cc(C)c(OCCO)c(C)c3)nc12]

To a solution of 2-amino-3-methoxy-benzoic acid (2.50 g, 14.9 mmol) in anhydrous acetonitrile (25 mL) at 50-55° C. were simultaneously added pyridine (2.36 g, 29.8 mmol) and a solution of triphosgene (1.46 g, 4.90 mmol) in anhydrous dichloromethane (10 mL) over 20 minutes, the reaction was stirred at 50-55° C. for 2 hours. The solvent was removed and the residue was mixed with water (100 mL), the solid was filtered and rinsed with cold water (30 mL) and dried. The crude was further washed with ether (20 mL) to give 6-methoxy-1H-benzo[d][1,3]oxazine-2,4-dione. Yield: 2.56 g (89%).

A solution of 8-methoxy-1H-benzo[d][1,3]oxazine-2,4-dione (1.50 g, 7.70 mmol) and 4-bromoaniline (1.40 g, 8.10 mmol) in anhydrous DMF (10 mL) was stirred at 115° C. for 16 hours under nitrogen. DMF was removed and the residue was mixed with water (100 mL) and ethyl acetate (150 mL). The organic phase was separated and washed with brine (50 mL). The solvent was removed and the residue was purified by column chromatography (SiO$_2$, hexane/ethyl acetate=1:1) to give 2-amino-N-(4-bromo-phenyl)-3-methoxy-benzamide. Yield: 1.49 g (60%).

To a solution of 2-amino-N-(4-bromo-phenyl)-3-methoxy-benzamide (0.600 g, 1.86 mmol) and 4-(2-hydroxy-ethoxy)-3,5-dimethyl-benzaldehyde (0.360 g, 1.86 mmol) in anhydrous ethanol (20 mL) was added anhydrous copper (II) chloride (0.750 g, 5.58 mmol). The reaction mixture was stirred at reflux for 16 hours under nitrogen. The solvent was removed and the residue was diluted with ethyl acetate (100 mL) and water (100 mL). After separation, the organic phase was further backwashed with water (100 mL), then brine (100 mL), dried over sodium sulfate, and concentrated. The crude product was purified by column chromatography (SiO$_2$, hexane/ethyl acetate=1:1) to give the title compound as a white solid. Yield: 250 mg (27%). MP 100-102° C. $^1$H-NMR (400 Hz, CDCl$_3$): δ 7.90 (d, 1H), 7.47 (m, 3H), 7.25 (m, 1H), 7.03 (d, 2H), 7.00 (s, 2H), 4.02 (s, 3H), 3.91 (m, 2H), 3.80 (t, 2H), 2.15 (s, 6H), 2.06 (t, 1H). MS (ES$^+$) m/z: 497.41 (M+1).

Example 18

Preparation of 2-(4-(2-hydroxyethoxy)-3,5-dimethylphenyl)-3-(4-isopropylphenyl)quinazolin-4(3H)-one

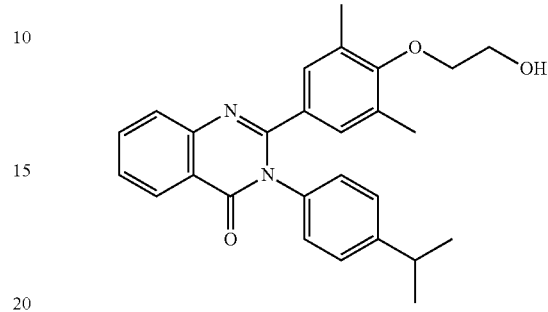

A solution of 1H-benzo[d][1,3]oxazine-2,4-dione (2.0 g, 12.2 mmol) and 4-isopropylaniline (1.92 mL, 13.5 mmol) in anhydrous DMF (10 mL) was stirred at 115° C. for 6 hours under nitrogen. DMF was removed and the residue was mixed with water (100 mL) and dichloromethane (150 mL). The organic phase was separated and washed with brine (50 mL). The solvent was removed and the residue was washed with ether (50 mL) to give 2-amino-N-(4-isopropyl-phenyl)-benzamide as a solid. Yield: 0.80 g (25.8%).

To a solution of 2-amino-N-(4-isopropylphenyl)benzamide (0.400 g, 1.57 mmol) and 4-(2-hydroxyethoxy)-3,5-dimethylbenzaldehyde (0.30 g, 1.57 mmol) in anhydrous ethanol (20 mL) was added anhydrous copper (II) chloride (0.63 g, 4.71 mmol). The reaction mixture was stirred at reflux for 4 hours under nitrogen. The solvent was removed and the residue was diluted with dichloromethane (150 mL) and water (100 mL). The organic phase was separated and further washed with water (100 mL), brine (100 mL), and dried over sodium sulfate. The crude mixture was purified by column chromatography on silica gel (230-400 mesh) using hexane/ethyl acetate (1:1) as eluent to give the title compound as a white solid. Yield: 100 mg (15.6%). MP 160-162° C. $^1$H-NMR (400 Hz, CDCl$_3$): δ 8.34 (d, J=7.6 Hz, 1H), 7.80 (m, 2H), 7.52 (m, 1H), 7.17 (d, J=8.4 Hz, 2H), 7.05 (d, J=8.4 Hz, 2H), 6.97 (s, 2H), 3.90 (m, 2H), 3.78 (t, J=4.8 Hz, 2H), 2.86 (m, 1H), 2.13 (s, 6H), 2.06 (t, J=6.4 Hz, 1H), 1.20 (d, J=7.2 Hz, 3H). MS (ES$^+$) m/z: 429.52 (M+1).

Example 19

Preparation of 3-(4-bromophenyl)-2-(4-(2-hydroxyethoxy)-3-methylphenyl)quinazolin-4(3H)-one

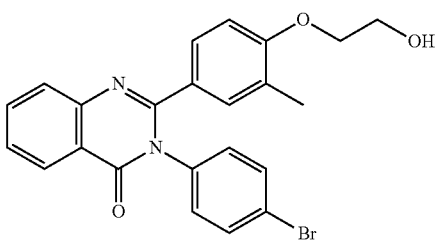

To a solution of 4-hydroxy-3-methylbenzaldehyde (0.50 g, 3.67 mmol) in anhydrous DMF (8 mL) was added K$_2$CO$_3$ (1.01 g, 7.34 mmol) and 1,3-dioxolan-2-one (0.65 g, 7.34 mmol), and the mixture was stirred at 110° C. for 60 hours under nitrogen. DMF was removed under vacuum, the residue was diluted with water (50 mL) and extracted with ethyl acetate. The organic layer was separated, washed with brine, dried over anhydrous Na$_2$SO$_4$ and concentrate under vacuum to give 3-methyl-4-hydroxylethoxybenzaldehyde as a yellow oil. Yield: 0.60 g (91%).

A mixture of isatoic anhydride (4.00 g, 24.5 mmol) and 4-bromoaniline (4.20 g, 24.5 mmol) in anhydrous DMF (30 mL) was stirred at 115° C. for 60 hours under nitrogen. DMF was removed under vacuum and the residue was partitioned between ethyl acetate (75 mL) and water (75 mL). The organic phase was separated, washed with brine and dried over anhydrous sodium sulfate. The solvent was evaporated under vacuum to give crude 2-amino-N-(4-bromophenyl)benzamide. Yield: 1.00 g (14%).

To a solution of 3-methyl-4-hydroxyethoxy-benzaldehyde (0.38 g, 2.10 mmol) and 2-amino-N-(4-bromophenyl)benzamide (0.60 g, 2.10 mmol) in anhydrous ethanol (15 mL) was added anhydrous CuCl$_2$ (0.85 g, 6.30 mmol). The reaction mixture was heated at reflux for 18 hours and then cooled to room temperature. Organic solvents were removed under reduced pressure, and the resulting residue was diluted with dichloromethane, washed with water, then brine, and dried over anhydrous magnesium sulfate. The solvent was removed under vacuum and the residual solid was purified by column chromatography (silica gel 230-400 mesh; 25-50% ethyl acetate in hexanes as eluent) to afford the title compound as a white solid. Yield: 0.21 g (22%). MP 92.0-93.0° C. $^1$H-NMR (400 MHz, CDCl$_3$): δ 8.32 (d, J=8.4 Hz, 1H), 7.81 (dd, J=4.8 and 1.2 Hz, 2H), 7.45-7.54 (m, 3H), 7.23 (m, 1H), 7.00 (m, 3H), 6.63 (d, J=8.4 Hz and 1H), 4.05 (t, J=4.4 Hz, 2H), 3.97 (t, J=4.4 Hz, 2H), 2.15 (s, 3H). MS (ES$^+$) m/z: 453.39, 451.37.

Example 20

Preparation of 3-(4-bromophenyl)-8-chloro-2-(4-(2-hydroxyethoxy)-3,5-dimethylphenyl)quinazolin-4(3H)-one

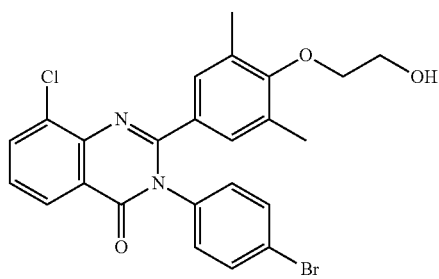 [SMILES: Cc1cc(-c2nc3c(Cl)cccc3c(=O)n2-c2ccc(Br)cc2)cc(C)c1OCCO]

To a stirred solution of 3-chloro-2-nitrobenzoic acid (2.01 g, 10.0 mmol) in anhydrous methanol (100 mL) nickel(II) chloride hexahydrate (4.75 g, 20.0 mmol) was added, and the reaction mixture was cooled to room temperature. To this green solution was added NaBH$_4$ (2.27 g, 60.0 mmol) in small portions over a period of 20 min. After the addition was complete, the reaction mixture was stirred at room temperature for 16 hours. The solvents were removed under vacuum and water (100 mL) was added, before neutralization to pH approximately equal to 4 with aqueous 2 N HCl. After extraction with methylene chloride (2×100 mL), the organic phase was separated, washed with water (100 mL), then brine (100 mL), and dried over anhydrous Na$_2$SO$_4$. The solvent was removed under vacuum to give 2-amino-3-chlorobenzoic acid as an off-white solid. Yield 0.90 g (52%).

To a stirred solution of 2-amino-3-chlorobenzoic acid (0.86 g, 5.00 mmol) in anhydrous acetonitrile (10 mL), a solution of triphosgene (0.49 g, 1.65 mmol) in anhydrous CH$_2$Cl$_2$ (5 mL) and anhydrous pyridine (0.79 g, 10.0 mmol) were added, drop-wise at 55° C., simultaneously over a period of 10 minutes. After the addition was complete, the reaction mixture was stirred at 55° C. for another 2 hours. The solvents were removed under vacuum and water (50 mL) was added. The separated solid was filtered, washed with water, followed by chilled CH$_2$Cl$_2$ (10 mL) and dried under vacuum to give 8-chloro-1H-benzo[d][1,3]oxazine-2,4-dione as an off-white solid. Yield 0.82 g (83%).

A mixture of 8-chloro-1H-benzo[d][1,3]oxazine-2,4-dione (0.80 g, 4.05 mmol) and 4-bromoaniline (0.70 g, 4.05 mmol) with anhydrous DMF (1 mL) was heated at 130° C. for 2 hours. Water (50 mL) was added, and the product was extracted with ethyl acetate (200 mL). The organic phase was separated, washed with water (100 mL), brine (100 mL) and dried over anhydrous Na$_2$SO$_4$. The solvent was evaporated in vacuo, and the crude material was washed with ether, to give 2-amino-N-(4-bromophenyl)-3-chlorobenzamide as an off-white solid. Yield 1.17 g (89%).

To a solution of 2-amino-N-(4-bromophenyl)-3-chlorobenzamide (0.52 g, 1.60 mmol) and 4-(2-hydroxyethoxy)-3,5-dimethylbenzaldehyde (0.31 g, 1.60 mmol) in anhydrous ethanol (20 mL), anhydrous copper (II) chloride (0.86 g, 6.40 mmol) was added and the reaction mixture was refluxed for 16 hours. The solvent was evaporated in vacuo, water (100 mL) was then added, and the product was extracted with ethyl acetate (200 mL). The organic phase was separated, washed with water (2×100 mL), then brine (100 mL), and dried over anhydrous Na$_2$SO$_4$. The solvent was evaporated, and the crude compound was purified by the Simpliflash system (20-40% ethyl acetate in hexanes as eluent), to give the title compound as a white solid. Yield 0.37 g (46%). MP 185-186° C. $^1$H-NMR (400 MHz, CDCl$_3$) δ 8.25 (d, J=8.20 Hz, 1H) 7.89 (d, J=7.42 Hz, 1H) 7.56-7.34 (m, 3H) 7.03 (t, J=4.29 Hz, 4H), 4.06-3.87 (m, 2H) 3.87-3.74 (m, 2H) 2.18 (s, 6H) 2.11-1.95 (m, 1H). MS (ES+) m/z: 499.36, 501.38 (100%), 503.33.

Example 21

Preparation of 2-(4-(2-hydroxyethoxy)-3,5-dimethylphenyl)-3-(4-morpholinophenyl)quinazolin-4(3H)-one

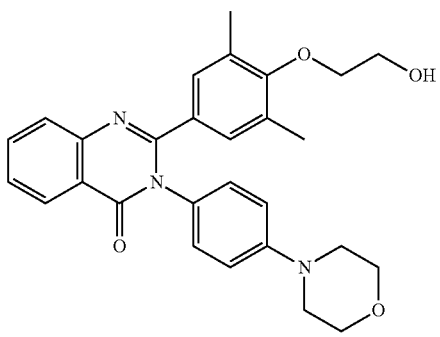 [SMILES: Cc1cc(-c2nc3ccccc3c(=O)n2-c2ccc(N3CCOCC3)cc2)cc(C)c1OCCO]

Isatoic anhydride (1.63 g, 10 mmol) was dissolved in DMF (40 mL) and added to 4-morpholinoaniline (1.78 g, 10 mmol). The reaction mixture was heated to 115° C. for 2.5 h. It was then cooled to room temperature, diluted with 5% lithium chloride solution (120 mL), and extracted with ethyl acetate (2×200 mL). The combined organic layers were washed with water (100 mL), 10% aqueous sodium hydroxide (100 mL), and water (100 mL). The organic layer was dried over sodium sulfate, filtered, and concentrated to give 2-amino-N-(4-morpholinophenyl)benzamide as a gray solid. Yield 1.71 g (57%).

To a stirred solution of 2-amino-N-(4-morpholinophenyl)benzamide (1.71 g, 5.75 mmol) in DMA (20 mL) was added 4-(2-(tert-butyldimethylsilyloxy)ethoxy)-3,5-dimethylbenzaldehyde (1.77 g, 5.75 mmol), NaHSO₃ (0.66 g, 6.33 mmol), and p-TsOH (0.22 g, 1.15 mmol). The reaction mixture was heated at 120° C. overnight, then heated to 140° C., and additional sodium bisulfite (2.60 g, 25 mmol) was added. After an additional 17 hours, the reaction mixture was cooled and diluted with 5% lithium chloride solution (120 mL), extracted with ethyl acetate (200 mL), and then washed with water (2×100 mL) and then brine (100 mL). The organic layer was dried over sodium sulfate, filtered, and concentrated. The residue was triturated with 1:1 hexanes/methylene chloride. Purification by flash chromatography on silica gel, eluting with 30% ethyl acetate/hexanes to 70% ethyl acetate/hexanes, afforded the title compound as a white solid (0.223 g, 8%). $^1$H-NMR (500 MHz, DMSO-d$_6$) δ 8.16 (dd, J=7.98, 1.3 Hz, 1H), 7.87 (td, J=8.4, 1.5 Hz, 1H), 7.72 (d, J=7.9 Hz, 1H), 7.57 (td, J=8.1, 1.1 Hz, 1H), 7.11 (d, J=8.9 Hz, 2H), 7.03 (s, 2H), 6.86 (d, J=9.0 Hz, 2H), 4.82 (br s, 1H), 3.68-3.72 (m, 6H), 3.63-3.67 (m, 2H), 3.08-3.09 (m, 4H), 2.10 (s, 6H).

Example 22

Preparation of 3-(4-tert-butylphenyl)-2-(4-(2-hydroxyethoxy)-3,5-dimethylphenyl)quinazolin-4(3H)-one

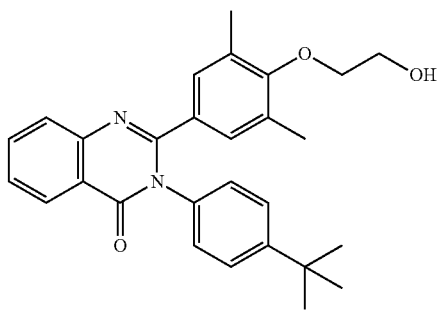 [SMILES: Cc1cc(-c2nc3ccccc3c(=O)n2-c2ccc(C(C)(C)C)cc2)cc(C)c1OCCO]

Following the method described for in Example 21, compound 2-amino-N-(4-tert-butylphenyl)benzamide was made from 4-tert-butylaniline, in 99% yield, and was isolated as a brown solid. 2-Amino-N-(4-tert-butylphenyl)benzamide (1.14 g, 4.25 mmol) and 4-(2-(tert-butyldimethylsilyloxy)ethoxy)-3,5-dimethylbenzaldehyde (1.31 g, 4.25 mmol) were combined in DMA (20 mL) and p-TsOH (0.164 g, 0.86 mmol) was added, followed by NaHSO₃ (0.488 g, 4.69 mmol). The mixture was heated to 140° C. for 24 hours, before concentrating, diluting with ethyl acetate (250 mL), washing with water (200 mL), and then brine (200 mL), before drying over Na₂SO₄, filtering, and concentrating. Purification by flash chromatography on silica gel, eluting with 1:1 ethyl acetate/hexanes to 100% ethyl acetate to 10% methanol/ethyl acetate, afforded the title compound as a white solid. $^1$H-NMR (300 MHz, DMSO-d$_6$) δ 8.19 (d, J=7.2 Hz, 1H), 7.87-7.92 (m, 1H), 7.75 (d, J=8.0 Hz, 1H), 7.56-7.61 (m, 1H), 7.35 (d, J=8.5 Hz, 2H), 7.18 (d, J=8.5 Hz, 2H), 6.96 (s, 2H), 4.83 (t, J=5.4 Hz, 1H), 3.62-3.67 (m, 4H), 2.06 (s, 6H), 1.25 (s, 9H). MS (APCI) m/z: 443 (M+H)⁺.

Example 23

Preparation of N-(4-(2-(4-(2-hydroxyethoxy)-3,5-dimethylphenyl)-4-oxoquinazolin-3(4H)-yl)phenyl)acetamide

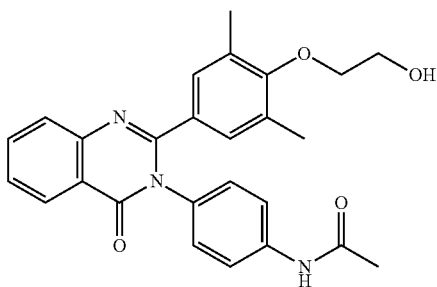 [SMILES: CC(=O)Nc1ccc(-n2c(-c3cc(C)c(OCCO)c(C)c3)nc3ccccc3c2=O)cc1]

Following the method described for Example 21, compound N-(4-acetamidophenyl)-2-aminobenzamide was made from 4-(piperidin-1-yl)aniline in 32% yield. Following the method described for Example 21, the title compound was made from N-(4-acetamidophenyl)-2-aminobenzamide in 13% yield, and isolated as a white solid. $^1$H-NMR (500 MHz, DMSO-d$_6$): δ 10.0 (br s, 1H), 8.19 (ddd, J=15.4, 7.9, 1.2 Hz, 1H), 7.89 (td, J=8.3, 1.5 Hz, 1H), 7.74 (d, J=7.6 Hz, 1H), 7.58 (td, J=8.0, 0.9 Hz, 1H), 7.51 (d, J=8.8 Hz, 2H), 7.20 (d, J=8.7 Hz, 2H), 7.04 (s, 2H), 4.81 (t, J=5.5 Hz, 1H), 3.71 (t, J=4.9 Hz, 2H), 3.65 (q, J=5.2 Hz, 2H), 2.10 (s, 6H), 2.03 (s, 3H).

Example 24

Preparation of N-(4-(2-(4-(2-hydroxyethoxy)-3,5-dimethylphenyl)-4-oxoquinazolin-3(4H)-yl)phenyl)isobutyramide

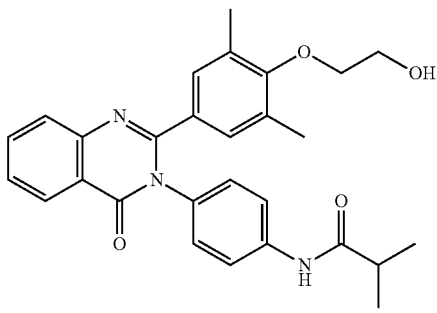 [SMILES: Cc1cc(-c2nc3ccccc3c(=O)n2-c2ccc(NC(=O)C(C)C)cc2)cc(C)c1OCCO]

A solution of N-(4-(2-(4-(2-hydroxyethoxy)-3,5-dimethylphenyl)-4-oxoquinazolin-3(4H)-yl)phenyl)acetamide (2.0 g, 4.50 mmol) in 2N HCl (50 mL) was stirred at reflux temperature for 30 minutes. The solids were filtered off solids and the aqueous filtrate was basified with NaOH, extracted with CH₂Cl₂, washed with brine, dried over Na₂SO₄, filtered, and concentrated in vacuo. Purification by flash chromatography on silica gel, eluting with 2% to 10% MeOH in CH$_2$Cl$_2$, afforded 3-(4-aminophenyl)-2-(4-(2-hydroxyethoxy)-3,5-dimethylphenyl)quinazolin-4(3H)-one as an off-white solid (1.35 g, 75%).

TEA (0.07 mL, 0.50 mmol) and isobutyryl chloride (0.25 mmol) were added to a solution of 3-(4-aminophenyl)-2-(4-(2-hydroxyethoxy)-3,5-dimethylphenyl)quinazolin-4(3H)-one (0.100 g, 0.25 mmol) in CH$_2$Cl$_2$ (5 mL), stirred at room temperature for 2 hours, and concentrated in vacuo. Purification by flash chromatography on silica gel, eluting with 2% to 10% MeOH in CH$_2$Cl$_2$, afforded the title compound as a white solid in 78% yield. $^1$H-NMR (300 MHz, DMSO-d$_6$): δ 9.90 (s, 1H), 8.17 (dd, J=6.8, 1.2 Hz, 1H), 7.85-7.91 (m, 1H), 7.72 (d, J=7.6 Hz, 1H), 7.53-7.65 (m, 3H), 7.20 (d, J=8.9 Hz, 2H), 7.04 (s, 2H), 4.83 (t, J=5.4 Hz, 1H), 3.61-3.72 (m, 4H), 2.56-2.63 (m, 1H), 2.10 (s, 6H), 1.08 (d, J=6.9 Hz, 6H). MS (APCI) m/z: 472 (M+H)$^+$.

Example 25

Preparation of methyl 4-(2-(4-(2-hydroxyethoxy)-3,5-dimethylphenyl)-4-oxoquinazolin-3(4H)-yl)benzoate

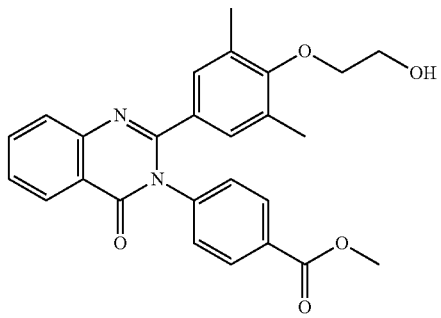 [SMILES: COC(=O)c1ccc(-n2c(-c3cc(C)c(OCCO)c(C)c3)nc3ccccc3c2=O)cc1]

Isatoic anhydride (4.0 g, 24.5 mmol) and methyl 4-aminobenzoate were combined and heated at 140° C. for 4 hours. The reaction was cool to room temperature and purified by flash chromatography on silica gel, eluting with 90-100% CH$_2$Cl$_2$ in heptane, to afford methyl 4-(2-aminobenzamido)benzoate (5.2 g, 78%). 4-(2-(tert-butyldimethylsilyloxy)ethoxy)-3,5-dimethylbenzaldehyde (1.0 g, 3.30 mmol) and anhydrous CuCl$_2$ (1.3 g, 9.90 mmol) were added to a solution of methyl 4-(2-aminobenzamido)benzoate (0.900 g, 3.30 mmol) in anhydrous EtOH (70 mL) and heated to reflux for 6 hours, before being cooled to room temperature and concentrated in vacuo. Purification by flash chromatography on silica gel, eluting with 5% MeOH in CH$_2$Cl$_2$, followed by further purification on silica gel, eluting with 30-100% EtOAc in heptane, afforded the title compound as a white solid (0.500 g, 34%). $^1$H-NMR (300 MHz, DMSO-d$_6$): δ 8.18 (dd, J=7.9, 1.1 Hz, 1H), 7.88-7.93 (m, 3H), 7.75 (d, J=6.7 Hz, 1H), 7.57-7.62 (m, 1H), 7.50 (d, J=8.5 Hz, 2H), 7.03 (s, 2H), 4.82 (t, J=5.5 Hz, 1H), 3.84 (s, 3H), 3.60-3.72 (m, 4H), 2.07 (s, 6H). MS (APCI) m/z: 445 (M+H)$^+$.

Example 26

Preparation of 3-(4-cyclohexylphenyl)-2-(4-(2-hydroxyethoxy)-3,5-dimethylphenyl)quinazolin-4(3H)-one

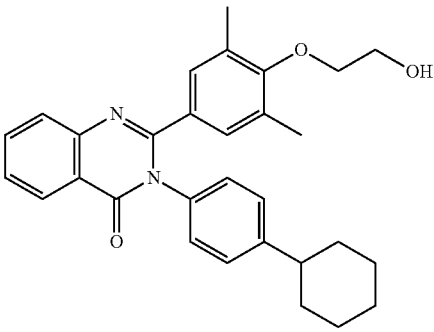 [SMILES: Cc1cc(-c2nc3ccccc3c(=O)n2-c2ccc(C3CCCCC3)cc2)cc(C)c1OCCO]

Following the method described for Example 21, 2-amino-N-(4-cyclohexylphenyl)benzamide was made from 4-cyclohexylaniline in 70% yield and isolated as a white solid. 2-Amino-N-(4-cyclohexylphenyl)-benzamide (4.58 mmol), 4-(2-(tert-butyldimethylsilyloxy)ethoxy)-3,5-dimethylbenzaldehyde (1.41 g, 4.58 mmol), anhydrous CuCl$_2$ (1.84 g, 13.74 mmol) were combined in anhydrous ethanol (100 mL) and heated at reflux for 7 hours. The mixture was concentrated, diluted with ethyl acetate (300 mL), washed with water (100 mL) and then brine (150 mL), dried over Na$_2$SO$_4$, filtered, and concentrated. Purification by flash chromatography on silica gel, eluting with 50% ethyl acetate/hexanes to 100% ethyl acetate, afforded the title compound in 55% yield, as a white solid. $^1$H-NMR (300 MHz, DMSO-d$_6$): δ 8.18 (d, J=7.5 Hz, 1H), 7.86-7.92 (m, 1H), 7.74 (d, J=8.1 Hz, 1H), 7.55-7.60 (m, 1H), 7.15-7.17 (m, 4H), 6.96 (s, 2H), 4.84 (t, J=5.3 Hz, 1H), 3.62-3.36 (m, 4H), 2.48-2.50 (m, 1H), 2.06 (s, 6H), 1.67-1.78 (m, 5H), 1.32-1.39 (m, 5H). MS (ESI) m/z: 469 (M+H)$^+$.

Example 27

Preparation of N-(4-(2-(4-(2-hydroxyethoxy)-3,5-dimethylphenyl)-4-oxoquinazolin-3(4H)-yl)phenyl)formamide

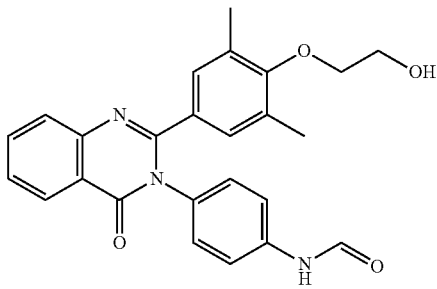 [SMILES: Cc1cc(-c2nc3ccccc3c(=O)n2-c2ccc(NC=O)cc2)cc(C)c1OCCO]

Methyl formate (10 mL, 162 mmol) was added to a solution of 3-(4-aminophenyl)-2-(4-(2-hydroxyethoxy)-3,5-dimethylphenyl)quinazolin-4(3H)-one (0.200 g, 0.50 mmol) in EtOH (10 mL) and heated at reflux. More methyl formate (5 mL, 81 mmol) was added and the mixture was heated at reflux for 2 more days, before being concentrated in vacuo and purification by flash chromatography on silica gel eluting with 2% to 8% MeOH in $CH_2Cl_2$. Further purification was effected by reverse phase chromatography eluting with 10% to 90% $CH_3CN$ in $H_2O$ with 0.1% TFA. The desired fractions were collected, basified, extracted, and concentrated, to afford the title compound as a white solid (0.072 g, 33%). $^1$H-NMR (300 MHz, DMSO-$d_6$, mixture of rotamers): δ 10.24 (s, 0.8H), 10.18 (m, 0.2H), 8.72-8.87 (m, 0.2H), 8.25 (d, J=1.7 Hz, 0.8H), 8.18 (dd, J=6.9, 1.1 Hz, 1H), 7.83-7.96 (m, 1H), 7.73 (d, J=8.0 Hz, 1H), 7.51-7.59 (m, 2.5H), 7.24 (d, J=8.7 Hz, 2H), 7.11-7.19 (m, 0.5H), 7.03 (s, 2H), 4.81 (t, J=5.4 Hz, 1H), 3.63-3.71 (m, 4H), 2.09 (s, 6H). MS (APCI) m/z: 430 (M+H)$^+$.

Example 28

Preparation of 3-(4-aminophenyl)-2-(4-(2-hydroxyethoxy)-3,5-dimethylphenyl)quinazolin-4(3H)-one

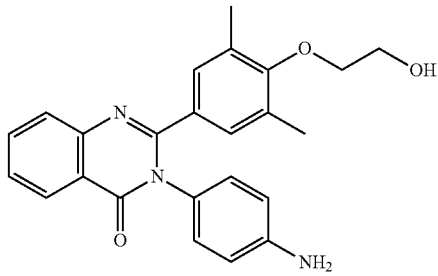 [SMILES: Cc1cc(-c2nc3ccccc3c(=O)n2-c2ccc(N)cc2)cc(C)c1OCCO]

A solution of N-(4-(2-(4-(2-hydroxyethoxy)-3,5-dimethylphenyl)-4-oxoquinazolin-3(4H)-yl)phenyl)acetamide (2.0 g, 4.50 mmol) in 2N HCl (50 mL) was stirred at reflux temperature for 30 minutes. Solids were filtered off and the aqueous filtrate was basified with NaOH. The filtrate was then extracted with $CH_2Cl_2$, washed with brine, dried over $Na_2SO_4$, filtered, and concentrated in vacuo. Purification by flash chromatography on silica gel eluting with 2% to 10% MeOH in $CH_2Cl_2$ afforded the title compound as an off-white solid (1.35 g, 75%). $^1$H-NMR (300 MHz, DMSO-$d_6$): δ 8.14 (d, J=6.9 Hz, 1H), 7.76-7.93 (m, 1H), 7.70 (d, J=8.1 Hz, 1H), 7.45-7.64 (m, 1H), 7.03 (s, 2H), 6.85 (d, J=8.6 Hz, 2H), 6.44 (d, J=8.5 Hz, 2H), 5.21 (s, 2H), 4.84 (t, J=5.5 Hz, 1H), 3.49-3.72 (m, 4H), 2.11 (s, 6H). MS (APCI) m/z: 402 (M+H)$^+$.

Example 29

Preparation of N-(4-(2-(4-(2-hydroxyethoxy)-3,5-dimethylphenyl)-4-oxoquinazolin-3(4H)-yl)phenyl)methanesulfonamide

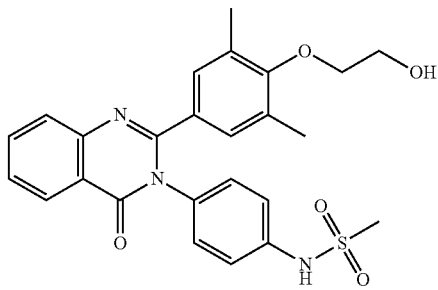 [SMILES: Cc1cc(-c2nc3ccccc3c(=O)n2-c2ccc(NS(C)(=O)=O)cc2)cc(C)c1OCCO]

TEA (0.24 mL, 1.70 mmol) followed by methanesulfonyl chloride (0.13 mL, 1.70 mmol) were added to a solution of 3-(4-aminophenyl)-2-(4-(2-hydroxyethoxy)-3,5-dimethylphenyl)quinazolin-4(3H)-one (0.230 g, 0.57 mmol) in $CH_2Cl_2$ (10 mL). After stirring for 6 hours at room temperature, the mixture was concentrated in vacuo. Purification by flash chromatography on silica gel, eluting with 2% to 8% MeOH in $CH_2Cl_2$, afforded 2-(2,6-dimethyl-4-(3-(4-(N-(methylsulfonyl)methylsulfonamido) phenyl)-4-oxo-3,4-dihydroquinazolin-2-yl)phenoxy)ethyl methanesulfonate (0.280 g, 77%).

LiOH (0.100 g, 4.10 mmol) was added to a solution of 2-(2,6-dimethyl-4-(3-(4-(N-(methylsulfonyl)methylsulfonamido)phenyl)-4-oxo-3,4-dihydroquinazolin-2-yl)phenoxy)ethyl methanesulfonate (0.280 g, 0.44 mmol) in dioxane (20 mL) and $H_2O$ (20 mL), before heating at reflux temperature for 3.5 hours. The mixture was diluted with saturated $NaHCO_3$, extracted with $CH_2Cl_2$, and concentrated in vacuo. Purification was effected by reverse phase chromatography eluting with 10% to 90% $CH_3CN$ in $H_2O$ with 0.1% TFA. The desired fractions were collected, basified, extracted, and concentrated, to afford the title compound as a white solid (0.110 g, 52%). $^1$H-NMR (300 MHz, DMSO-$d_6$): δ 9.83 (s, 1H), 8.17 (dd, J=6.7, 1.1 Hz, 1H), 7.86-7.92 (m, 1H), 7.74 (d, J=7.8 Hz, 1H), 7.52-7.65 (m, 1H), 7.27 (d, J=8.8 Hz, 2H), 7.13 (d, J=8.8 Hz, 2H), 7.01 (s, 2H), 4.83 (t, J=5.5 Hz, 1H), 3.56-3.69 (m, 4H), 2.92 (s, 3H), 2.09 (s, 6H). MS (APCI) m/z: 480 (M+H)$^+$.

Example 30

Preparation of N-(4-(2-(4-(2-hydroxyethoxy)-3,5-dimethylphenyl)-4-oxoquinazolin-3(4H)-yl)phenyl)benzenesulfonamide

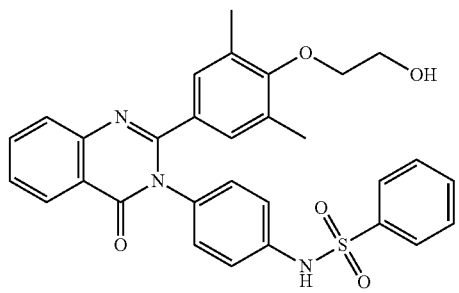 [SMILES: Cc1cc(-c2nc3ccccc3c(=O)n2-c2ccc(NS(=O)(=O)c3ccccc3)cc2)cc(C)c1OCCO]

Following the method described for Example 21, 2-amino-N-(4-(phenylsulfonamido)phenyl)benzamide was made from N-(4-aminophenyl)benzenesulfonamide in 61% yield.

Following the method described for Example 26, the title compound was made from 2-amino-N-(4-(phenylsulfonamido)phenyl)benzamide in 10% yield. $^1$H-NMR (300 MHz, DMSO-$d_6$): δ 10.43 (s, 1H), 8.13 (d, J=6.9 Hz, 1H), 7.87 (t, J=6.9 Hz, 1H), 7.51-7.72 (m, 7H), 7.17 (d, J=8.7 Hz, 2H), 7.00 (d, J=8.7 Hz, 2H), 6.94 (s, 2H), 4.81-4.93 (m, 1H), 3.56-3.78 (m, 4H), 2.02 (s, 6H). MS (ESI) m/z: 542 (M+H)$^+$.

Example 31

Preparation of N-(4-(2-(4-(2-hydroxyethoxy)-3,5-dimethylphenyl)-4-oxoquinazolin-3(4H)-yl)phenyl)propane-2-sulfonamide

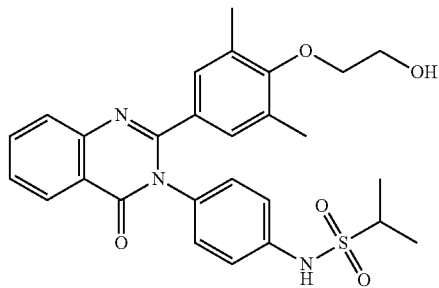 [SMILES: Cc1cc(-c2nc3ccccc3c(=O)n2-c2ccc(NS(=O)(=O)C(C)C)cc2)cc(C)c1OCCO]

Isatoic anhydride (0.690 g, 4.20 mmol) was added to a solution of N-(4-aminophenyl)propane-2-sulfonamide (0.910 g, 4.20 mmol) in DMF (15 mL) and heated at 115° C. overnight. The mixture was concentrated in vacuo and purified by flash chromatography on silica gel, eluting with 6% MeOH in CH$_2$Cl$_2$. Further purification was effected by reverse phase chromatography, eluting with 10% to 90% CH$_3$CN in H$_2$O with 0.1% TFA. The desired fractions were collected, basified, and extracted with EtOAc to afford 2-amino-N-(4-(1-methylethylsulfonamido)phenyl)benzamide (0.325 g, 23%).

Following the method described for Example 26, the title compound was made from 2-amino-N-(4-(1-methylethylsulfonamido)phenyl)benzamide in 60% yield. $^1$H-NMR (300 MHz, DMSO-d$_6$): δ 9.87 (s, 1H), 8.17 (dd, J=6.8, 1.2 Hz, 1H), 7.86-7.91 (m, 1H), 7.73 (d, J=7.6 Hz, 1H), 7.52-7.61 (m, 1H), 7.15-7.25 (m, 4H), 7.00 (s, 2H), 4.85 (t, J=5.3 Hz, 1H), 3.61-3.70 (m, 4H), 3.01-3.19 (m, 1H), 2.09 (s, 6H), 1.19 (d, J=6.9 Hz, 6H). MS (APCI) m/z: 508 (M+H)$^+$.

Example 32

Preparation of 3-(4-(dimethylamino)phenyl)-2-(4-(2-hydroxyethoxy)-3,5-dimethylphenyl)quinazolin-4(3H)-one

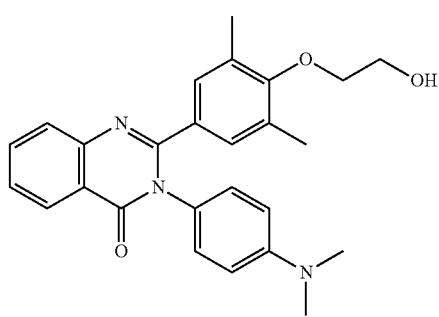 [SMILES: Cc1cc(-c2nc3ccccc3c(=O)n2-c2ccc(N(C)C)cc2)cc(C)c1OCCO]

TEA (2.1 mL, 15.0 mmol) and DMAP (0.020 g, 0.00016 mmol), followed by TBDMSCI (1.5 g, 10.0 mmol), were added to a solution of 3-(4-aminophenyl)-2-(4-(2-hydroxyethoxy)-3,5-dimethylphenyl)quinazolin-4(3H)-one (2.0 g, 5.0 mmol) in CH$_2$Cl$_2$ (20 mL). After heating to reflux temperature and stirring for 30 minutes, the mixture was concentrated in vacuo and purified by flash chromatography on silica gel, eluting with 1% to 8% MeOH in CH$_2$Cl$_2$. Further purification was effected by flash chromatography on silica gel, eluting with 3% MeOH in CH$_2$Cl$_2$, to afford 3-(4-aminophenyl)-2-(4-(2-(tert-butyldimethylsilyloxy)ethoxy)-3,5-dimethylphenyl)quinazolin-4(3H)-one (1.6 g, 62%).

Hünig's base (0.27 mL, 1.50 mmol) followed by iodomethane (0.04 mL, 0.77 mmol) were added to a solution of 3-(4-aminophenyl)-2-(4-(2-(tert-butyldimethylsilyloxy)ethoxy)-3,5-dimethylphenyl)quinazolin-4(3H)-one (0.200 g, 0.38 mmol) in DMF (5 mL). The mixture was stirred at room temperature for 2 hours, then heated at reflux overnight, before concentrating in vacuo and purifying by flash chromatography on silica gel, eluting with 60% of 92:7:1 CHCl$_3$/MeOH/concentrated NH$_4$OH in CH$_2$Cl$_2$. The desired fractions were further purified by reverse-phase chromatography, eluting with 10% to 90% CH$_3$CN in H$_2$O with 0.1% TFA. The desired fractions were collected, basified, extracted, and concentrated to afford the title compound, as a white solid (0.050 g, 31%). $^1$H-NMR (300 MHz, DMSO-d$_6$): δ 8.15 (dd, J=8.0, 1.1 Hz, 1H), 7.83-7.89 (m, 1H), 7.71 (d, J=7.7 Hz, 1H), 7.53-7.58 (m, 1H), 7.02-7.05 (m, 4H), 6.62 (d, J=9.0 Hz, 2H), 4.83 (t, J=5.3 Hz, 1H), 3.62-3.72 (m, 4H), 2.87 (s, 6H), 2.10 (s, 6H). MS (APCI) m/z: 430 (M+H)$^+$

Example 33

Preparation of 3-(4-sec-butylphenyl)-2-(4-(2-hydroxyethoxy)-3-methylphenyl)quinazolin-4(3H)-one

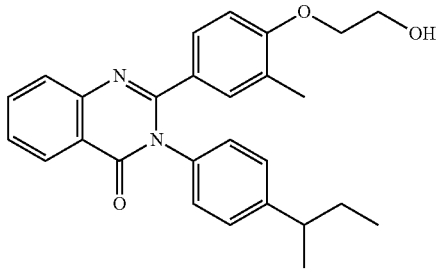 [SMILES: CCC(C)c1ccc(-n2c(-c3ccc(OCCO)c(C)c3)nc3ccccc3c2=O)cc1]

K$_2$CO$_3$ (0.135 g, 0.97 mmol) was added to a solution of 3-(4-sec-butylphenyl)-2-(4-hydroxy-3-methylphenyl)quinazolin-4(3H)-one (0.250 g, 0.65 mmol) in DMF (15 mL). The mixture was stirred at room temperature for 30 min, then (2-bromoethoxy)(tert-butyl)dimethylsilane (0.16 mL, 0.78 mmol) was added and the reaction was heated at reflux temperature for 3 hours, before concentrating in vacuo and dissolving the residue in EtOAc. The organics were washed with saturated NaHCO$_3$ and brine, dried (Na$_2$SO$_4$), filtered, and concentrated in vacuo. Purification by flash chromatography on silica gel, eluting with 2% to 40% EtOAc in heptane, afforded 2-(4-(2-(tert-butyldimethylsilyloxy)-ethoxy)-3-methylphenyl)-3-(4-sec-butylphenyl)quinazolin-4(3H)-one (0.320 g, 90%).

A 1 M THF solution of TBAF (1.7 mL, 1.70 mmol) was added to a solution of 2-(4-(2-(tert-butyldimethylsilyloxy)ethoxy)-3-methylphenyl)-3-(4-sec-butylphenyl)quinazolin-4(3H)-one (0.320 g, 0.59 mmol) in THF (2 mL). The mixture was stirred at room temperature for 1 hour and concentrated in vacuo. Purification by flash chromatography on silica gel, eluting with 10% to 90% EtOAc in heptane, afforded the title compound, as a white solid (0.175 g, 69%). $^1$H-NMR (300 MHz, DMSO-d$_6$): δ 8.15-8.18 (m, 1H), 7.80-7.95 (m, 1H), 7.74 (d, J=7.7 Hz, 1H), 7.49-7.64 (m, 1H), 7.01-7.25 (m, 6H), 6.72 (d, J=8.5 Hz, 1H), 4.81 (t, J=5.5 Hz, 1H), 3.80-3.97 (m, 2H), 3.56-3.73 (m, 2H), 2.54-2.67 (m, 1H), 1.99 (s, 3H), 1.32-1.66 (m, 2H), 1.17 (d, J=6.9 Hz, 3H), 0.67 (t, J=7.3 Hz, 3H). MS (APCI) m/z: 429 (M+H)$^+$.

Example 34

Preparation of 3-(4-chlorophenyl)-2-(4-(2-hydroxyethoxy)-3-methylphenyl)quinazolin-4(3H)-one

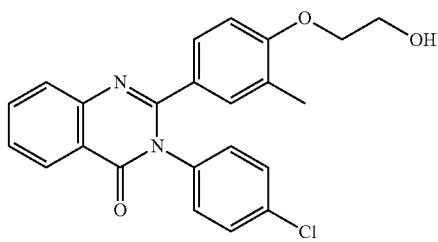 [SMILES: Cc1cc(-c2nc3ccccc3c(=O)n2-c2ccc(Cl)cc2)ccc1OCCO]

Anhydrous CuCl$_2$ (0.306 g, 2.20 mmol) and 4-hydroxy-3-methylbenzaldehyde (0.155 g, 1.10 mmol) were added to a solution of 2-amino-N-(4-chlorophenyl)benzamide (0.280 g, 1.10 mmol) in anhydrous EtOH (10 mL). The mixture was heated at reflux temperature for 4 hours and concentrated in vacuo. The residue was dissolved in EtOAc, washed with H$_2$O and brine, dried (Na$_2$SO$_4$), filtered, and concentrated in vacuo. Purification by flash chromatography on silica gel, eluting with 5% to 50% EtOAc in heptane, afforded 3-(4-chlorophenyl)-2-(4-hydroxy-3-methylphenyl)quinazolin-4(3H)-one (0.230 g, 57%).

K$_2$CO$_3$ (0.131 g, 0.95 mmol) was added to a solution of 3-(4-chlorophenyl)-2-(4-hydroxy-3-methylphenyl)quinazolin-4(3H)-one (0.230 g, 0.63 mmol) in DMF (15 mL) and stirred for 30 min. (2-Bromoethoxy)(tert-butyl)dimethylsilane (0.16 mL, 0.76 mmol) was added and the reaction was heated to reflux temperature for 3 hours, and concentrated in vacuo. The residue was dissolved in EtOAc, washed with saturated NaHCO$_3$, and then brine, dried (Na$_2$SO$_4$), filtered, and concentrated in vacuo, to afford 2-(4-(2-(tert-Butyldimethylsilyloxy)ethoxy)-3-methylphenyl)-3-(4-chlorophenyl)quinazolin-4(3H)-one (0.340 g, quantitative).

A 1M THF solution of TBAF (1.90 mL, 1.90 mmol) was added to a solution of 2-(4-(2-(tert-butyldimethylsilyloxy)ethoxy)-3-methylphenyl)-3-(4-chlorophenyl)quinazolin-4(3H)-one (0.340 g, 0.65 mmol) in THF (5 mL). The mixture was stirred at room temperature for 1 hour and concentrated in vacuo. Purification by flash chromatography on silica gel, eluting with 10% to 100% EtOAc in heptane, afforded the title compound as a white solid (0.190 g, 72%). $^1$H-NMR (300 MHz, DMSO-d$_6$): δ 8.17 (dd, J=6.8, 1.0 Hz, 1H), 7.89 (d, J=6.8 Hz, 1H), 7.75 (d, J=8.8 Hz, 1H), 7.55-7.59 (m, 1H), 7.28-7.48 (m, 4H), 7.21 (d, J=1.5 Hz, 1H), 7.04-7.16 (m, 1H), 6.77 (d, J=8.7 Hz, 1H), 4.81 (t, J=5.7 Hz, 1H), 3.86-4.01 (m, 2H), 3.60-3.77 (m, 2H), 2.06 (s, 3H). MS (APCI) m/z: 407 (M+H)$^+$.

Example 35

Preparation of 3-(4-sec-butylphenyl)-2-(pyridin-3-yl)quinazolin-4(3H)-one

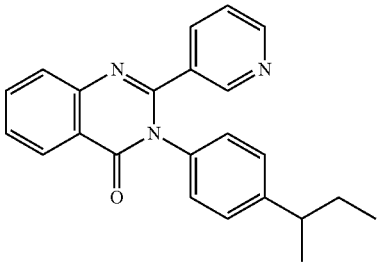 [SMILES: CCC(C)c1ccc(-n2c(-c3cccnc3)nc3ccccc3c2=O)cc1]

Following the method described for Example 45, the title compound was made from 3-pyridylcarboxaldehyde in 57% yield and isolated as a white solid. $^1$H-NMR (300 MHz, DMSO-d$_6$): δ 8.57 (d, J=1.6 Hz, 1H), 8.42 (dd, J=4.9 Hz, 1.6 Hz, 1H), 8.22 (dd, J=8.0 Hz, 1.2 Hz, 1H), 7.90-7.96 (m, 1H), 7.80 (d, J=7.7 Hz, 1H), 7.70-7.74 (m, 1H), 7.61-7.66 (m, 1H), 7.21-7.29 (m, 3H), 7.13-7.17 (m, 2H), 2.54-2.57 (m, 1H), 1.43-1.53 (m, 2H), 1.14 (d, J=6.9 Hz, 3H), 0.63 (t, J=7.3 Hz, 3H). MS (APCI) m/z: 356 (M+H)$^+$.

Example 36

Preparation of 3-(4-chlorophenyl)-2-(quinolin-3-yl)quinazolin-4(3H)-one

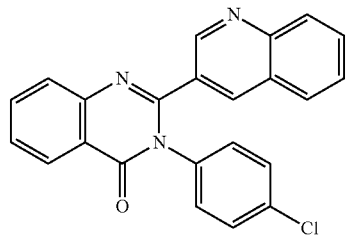 [SMILES: O=c1c2ccccc2nc(-c2cnc3ccccc3c2)n1-c1ccc(Cl)cc1]

3-Quinoline carboxaldehyde (0.41 mmol) and anhydrous CuCl$_2$ (0.110 g, 0.82 mmol) were added to a solution of 2-amino-N-(4-chlorophenyl)benzamide (0.100 g, 0.41 mmol) in anhydrous EtOH (10 mL). The mixture was heated at reflux temperature for 4 hours and concentrated in vacuo. The residue was dissolved in EtOAc and washed with H$_2$O and brine, dried (Na$_2$SO$_4$), filtered, and concentrated. Purification by flash chromatography on silica gel, eluting with 5% to 50% EtOAc in heptane, afforded the title compound as a white solid (14%). $^1$H-NMR (300 MHz, DMSO-d$_6$): δ 8.83 (d, J=2.1 Hz, 1H), 8.45 (d, J=1.8 Hz, 1H), 8.24 (d, J=8.0 Hz, 1H), 7.88-8.03 (m, 3H), 7.74-7.88 (m, 2H), 7.56-7.73 (m, 2H), 7.52 (d, J=8.6 Hz, 2H), 7.40 (d, J=8.7 Hz, 2H). MS (APCI) m/z: 384 (M+H)$^+$.

Example 37

Preparation of 3-(4-sec-butylphenyl)-2-(5-fluoropyridin-3-yl)quinazolin-4(3H)-one

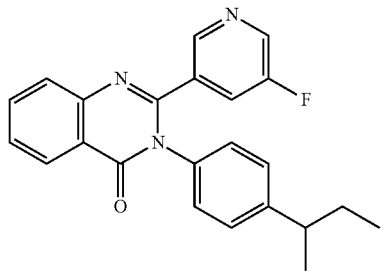 [SMILES: CCC(C)c1ccc(-n2c(-c3cncc(F)c3)nc3ccccc3c2=O)cc1]

Following the method described for Example 45, the title compound was made from 5-fluoronicotinaldehyde in 53% yield and isolated as a white solid. $^1$H-NMR (300 MHz, DMSO-$d_6$): δ 8.48-8.49 (m, 2H), 8.22-8.25 (m, 1H), 7.92-7.97 (m, 1H), 7.82 (d, J=7.7 Hz, 1H), 7.63-7.69 (m, 2H), 7.27-7.32 (m, 2H), 7.15-7.21 (m, 2H), 2.55-2.60 (m, 1H), 1.39-1.58 (m, 2H), 1.15 (d, J=6.9 Hz, 3H), 0.62 (t, J=7.3 Hz, 3H). MS (APCI) m/z: 374 (M+H)$^+$.

Example 38

Preparation of 3-(4-chlorophenyl)-2-(6-chloropyridin-3-yl)quinazolin-4(3H)-one

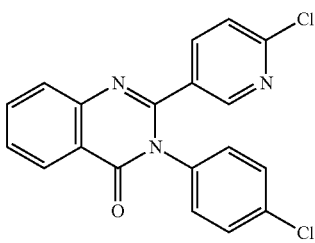 [SMILES: O=c1c2ccccc2nc(-c2ccc(Cl)nc2)n1-c1ccc(Cl)cc1]

2-Amino-N-(4-chlorophenyl)benzamide (0.500 g, 2.03 mmol) and 6-chloronicotinaldehyde (2.23 mmol), NaHSO$_3$ (0.253 g, 2.44 mmol) and p-TsOH (0.039 g, 0.20 mmol) were dissolved in DMA (20 mL) and heated at 150° C. for 21 hours. The mixture was cooled to room temperature, diluted with ethyl acetate (100 mL), washed with water (2×200 mL), dried (Na$_2$SO$_4$), filtered, and concentrated. Flash chromatograph on silica gel, eluting with 30% ethyl acetate/heptane to 70% ethyl acetate/heptane, afforded the title compound as a white solid (4%). $^1$H-NMR (300 MHz, DMSO-$d_6$): δ 8.46 (d, J=2.1 Hz, 1H), 8.23 (d, J=8.1 Hz, 1H), 7.92-7.97 (m, 1H), 7.80-7.86 (m, 2H), 7.63-7.68 (m, 1H), 7.47-7.50 (m, 5H). MS (APCI) m/z: 368 (M+H)$^+$.

Example 39

Preparation of 3-(4-sec-butylphenyl)-2-(6-chloropyridin-3-yl)quinazolin-4(3H)-one

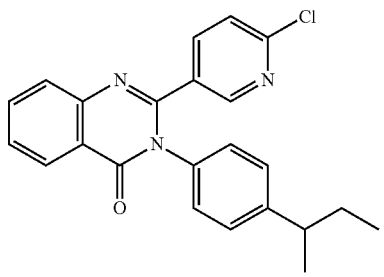

Following the method described for Example 45, the title compound was made from 6-chloronicotinaldehyde in 16% yield and isolated as a white solid. $^1$H-NMR (500 MHz, DMSO-$d_6$): δ 8.41 (d, J=2.3 Hz, 1H), 8.22-8.23 (m, 1H), 7.91-7.95 (m, 1H), 7.78-7.82 (m, 2H), 7.63-7.66 (m, 1H), 7.38-7.40 (m, 1H), 7.26-7.30 (m, 2H), 7.15-7.20 (m, 2H), 2.57-2.58 (m, 1H), 1.46-1.54 (m, 2H), 1.16 (d, J=6.9 Hz, 3H), 0.63 (t, J=7.3 Hz, 3H). MS (APCI) m/z: 390 (M+H)$^+$.

Example 40

Preparation of 3-(4-sec-butylphenyl)-2-(6-methoxypyridin-3-yl)quinazolin-4(3H)-one

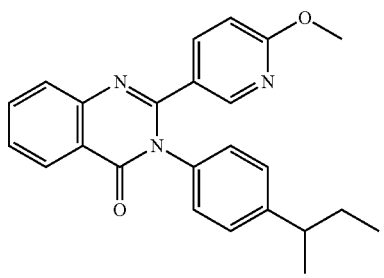 [SMILES: CCC(C)c1ccc(-n2c(-c3ccc(OC)nc3)nc3ccccc3c2=O)cc1]

6-Methoxy-3-pyridinecarboxaldehyde (1.20 mmol), NaHSO$_3$ (0.200 g, 1.90 mmol) and p-TsOH (0.024 g, 0.12 mmol) were added to a solution of 2-amino-N-(4-sec-butylphenyl)benzamide (0.340 g, 1.20 mmol) in DMA (10 mL). The mixture was heated and stirred at 150° C. overnight and concentrated in vacuo. The residue was dissolved in EtOAc, and washed with H$_2$O, then brine, dried (Na$_2$SO$_4$), filtered, and concentrated in vacuo. Purification by flash chromatography on silica gel, eluting with 15% to 100% EtOAc in heptane, afforded the title compound as a white solid (26%). $^1$H-NMR (300 MHz, DMSO-$d_6$): δ 8.11-8.27 (m, 2H), 7.89-7.91 (m, 1H), 7.77 (d, J=7.5 Hz, 1H), 7.51-7.67 (m, 2H), 7.11-7.33 (m, 4H), 6.62 (d, J=8.0 Hz, 1H), 3.77 (s, 3H), 2.54-2.68 (m, 1H), 1.30-1.71 (m, 2H), 1.16 (d, J=7.0 Hz, 3H), 0.64 (t, J=7.4 Hz, 3H). MS (APCI) m/z: 386 (M+H)$^+$.

Example 41

Preparation of 2-(6-bromopyridin-3-yl)-3-(4-chlorophenyl)quinazolin-4(3H)-one

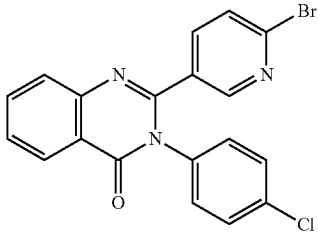 [SMILES: O=c1c2ccccc2nc(-c2ccc(Br)nc2)n1-c1ccc(Cl)cc1]

Following the method described for Example 38, the title compound was made from 6-bromo-nicotinaldehyde in 12% yield and isolated as a white solid. $^1$H-NMR (300 MHz, DMSO-$d_6$): δ 8.42-8.43 (m, 1H), 8.21-8.24 (m, 1H), 7.92-7.97 (m, 1H), 7.81 (d, J=7.7 Hz, 1H), 7.69-7.75 (m, 1H), 7.61-7.68 (m, 2H), 7.35-7.55 (m, 4H). MS (APCI) m/z: 412 (M+H)$^+$.

Example 42

Preparation of 2-(6-bromopyridin-3-yl)-3-(4-sec-butylphenyl)quinazolin-4(3H)-one

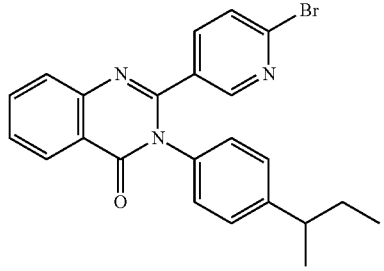

Following the method described for Example 45, the title compound was made from 6-bromonicotinaldehyde in 20% yield and isolated as a white solid. $^1$H-NMR (300 MHz, DMSO-$d_6$): δ 8.39 (d, J=2.3 Hz, 1H), 8.21-8.24 (m, 1H), 7.91-7.96 (m, 1H), 7.81 (d, J=7.8 Hz, 1H), 7.59-7.69 (m, 2H), 7.52 (d, J=8.2 Hz, 1H), 7.26-7.41 (m, 2H), 7.15-7.21 (m, 2H), 2.54-2.63 (m, 1H), 1.37-1.62 (m, 2H), 1.16 (d, J=6.9 Hz, 3H), 0.63 (t, J=7.3 Hz, 3H). MS (ESI) m/z: 434 (M+H)$^+$.

Example 43

Preparation of 3-(4-chlorophenyl)-2-(6-(diethylamino)pyridin-3-yl)quinazolin-4(3H)-one

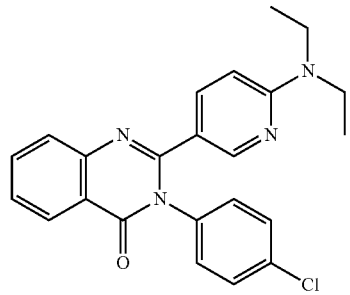 [SMILES: CCN(CC)c1ccc(-c2nc3ccccc3c(=O)n2-c2ccc(Cl)cc2)cn1]

2-(6-bromopyridin-3-yl)-3-(4-chlorophenyl)quinazolin-4(3H)-one (0.035 g, 0.085 mmol), Pd(OAc)$_2$ (0.002 g, 0.009 mmol), DPPF (0.004 g, 0.007 mmol), NaOt-Bu (0.011 g, 0.110 mmol), and diethylamine (0.020 mL, 0.19 mmol) were combined in toluene (2 mL) in a microwave tube under nitrogen. The mixture was microwaved at 80° C., 300 W, for 30 minutes. Additional diethylamine (0.040 mL, 0.38 mmol) was added and the microwaving was continued at 90° C. for 2.5 hours. The mixture was concentrated and purified by flash chromatography on silica gel, eluting with 30% ethyl acetate/heptane to 100% ethyl acetate, to afford the title compound as a white solid (0.017 g, 49%). $^1$H-NMR (300 MHz, DMSO-$d_6$): δ 8.14-8.17 (m, 1H), 8.08 (d, J=2.8 Hz, 1H), 7.85-7.91 (m, 1H), 7.73 (d, J=7.8 Hz, 1H), 7.35-7.58 (m, 6H), 6.43 (d, J=9.0 Hz, 1H), 3.44 (q, J=7.0 Hz, 4H), 1.05 (t, 6.9 Hz, 6H). MS (APCI) m/z: 405 (M+H)$^+$.

Example 44

Preparation of 3-(4-sec-butylphenyl)-2-(6-(diethylamino)pyridin-3-yl)quinazolin-4(3H)-one

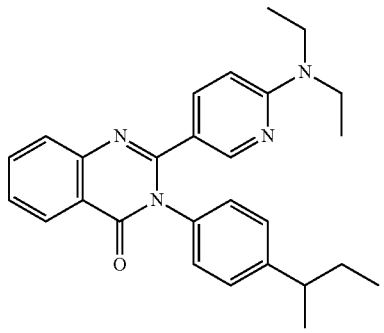 [SMILES: CCC(C)c1ccc(-n2c(-c3ccc(N(CC)CC)nc3)nc3ccccc3c2=O)cc1]

2-(6-bromopyridin-3-yl)-3-(4-sec-butylphenyl)quinazolin-4(3H)-one (0.110 g, 0.253 mmol), Pd(OAc)$_2$ (0.017 g, 0.076 mmol), DPPF (0.035 g, 0.063 mmol), NaOt-Bu (0.032 g, 0.330 mmol), and diethylamine (0.040 mL, 0.385 mmol) were combined in toluene (2 mL) in a microwave tube under nitrogen. The mixture was microwaved at 90° C., 300 W, for 3 hours. The mixture was concentrated and purified by flash chromatography on silica gel, eluting with 30% ethyl acetate/heptane to 100% ethyl acetate, to afford the title compound as a white solid (0.040 g, 37%). $^1$H-NMR (300 MHz, DMSO-$d_6$): δ 8.14-8.17 (m, 1H), 8.02 (d, J=2.3 Hz, 1H), 7.84-7.90 (m, 1H), 7.73 (d, J=7.8 Hz, 1H), 7.52-7.57 (m, 1H), 7.32-7.35 (m, 1H), 7.18-7.28 (m, 4H), 6.33 (d, J=9.1 Hz, 1H), 3.41 (q, J=6.9 Hz, 4H), 2.57-2.64 (m, 1H), 1.41-1.62 (m, 2H), 1.19 (d, J=6.9 Hz, 3H), 1.01 (t, J=6.9 Hz, 6H), 0.67 (t, J=7.3 Hz, 3H). MS (APCI) m/z: 427 (M+H)$^+$.

Example 45

Preparation of 3-(4-sec-butylphenyl)-2-(pyrimidin-5-yl)quinazolin-4(3H)-one

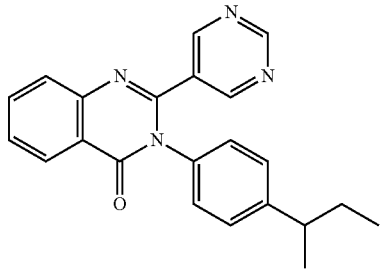 [SMILES: CCC(C)c1ccc(-n2c(-c3cncnc3)nc3ccccc3c2=O)cc1]

2-amino-N-(4-sec-butylphenyl)benzamide (0.544 g, 2.03 mmol) and pyrimidine-5-carbaldehyde (0.241 g, 2.23 mmol), NaHSO₃ (0.253 g, 2.44 mmol) and p-TsOH (0.039 g, 0.20 mmol) were dissolved in DMA (20 mL) and heated at 150° C. for 18 hours. The mixture was cooled to room temperature, diluted with ethyl acetate (100 mL), washed with water (2×200 mL), dried (Na₂SO₄), filtered, and concentrated. Flash chromatograph on silica gel, eluting with 20% ethyl acetate/heptane to 70% ethyl acetate/heptane, afforded the title compound as a white solid (0.280 g, 39%). ¹H-NMR (300 MHz, DMSO-d₆): δ 9.05 (s, 1H), 8.77 (s, 2H), 8.22-8.25 (m, 1H), 7.92-7.98 (m, 1H), 7.83 (d, J=7.7 Hz, 1H), 7.64-7.69 (m, 1H), 7.31-7.35 (m, 2H), 7.18-7.23 (m, 2H), 2.54-2.61 (m, 1H), 1.37-1.58 (m, 2H), 1.15 (d, J=6.9 Hz, 3H), 0.64 (t, J=7.3 Hz, 3H). MS (APCI) m/z: 357 (M+H)⁺.

Example 46

Preparation of 3-(4-sec-butylphenyl)-2-(6-methylpyridin-3-yl)quinazolin-4(3H)-one

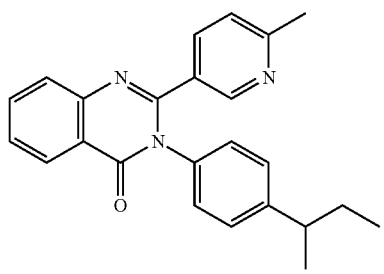 [SMILES: CCC(C)c1ccc(-n2c(-c3ccc(C)nc3)nc3ccccc3c2=O)cc1]

3-(4-sec-butylphenyl)-2-(6-chloropyridin-3-yl)quinazolin-4(3H)-one (0.345 g, 0.89 mmol), trimethyboroxine (0.124 mL, 0.89 mmol), Pd(PPh₃)₄ (0.102 g, 0.09 mmol), and K₂CO₃ (0.368 g, 2.67 mmol) were combined in dioxane (10 mL) and heated at reflux under nitrogen for 5 hours. The reaction mixture was cooled to room temperature, filtered through Celite®, with THF washings, concentrated, and purified by flash chromatography on silica gel, eluting with 50% ethyl acetate/heptane to 100% ethyl acetate, to afford the title compound as a white solid (0.195 g, 59%). ¹H-NMR (300 MHz, DMSO-d₆): δ 8.43 (d, J=2.0 Hz, 1H), 8.20 (d, J=6.9 Hz, 1H), 7.89-7.94 (m, 1H), 7.79 (d, J=7.9 Hz, 1H), 7.55-7.65 (m, 2H), 7.13-7.27 (m, 4H), 7.07 (d, J=8.1 Hz, 1H), 2.55-2.60 (m, 1H), 2.36 (s, 3H), 1.37-1.58 (m, 2H), 1.15 (d, J=6.9 Hz, 3H), 0.66 (t, J=7.3 Hz, 3H). MS (APCI) m/z: 370 (M+H)⁺.

Example 47

Preparation of 3-(4-chlorophenyl)-2-(6-methylpyridin-3-yl)quinazolin-4(3H)-one

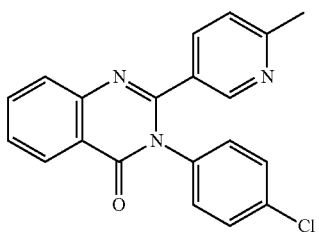 [SMILES: Cc1ccc(-c2nc3ccccc3c(=O)n2-c2ccc(Cl)cc2)cn1]

3-(4-chlorophenyl)-2-(6-chloropyridin-3-yl)quinazolin-4(3H)-one (0.200 g, 0.54 mmol), trimethyboroxine (0.076 mL, 0.54 mmol), Pd(PPh₃)₄ (0.063 g, 0.05 mmol), and K₂CO₃ (0.224 g, 1.62 mmol) were combined in dioxane (10 mL) and heated at reflux under nitrogen for 5 hours. Additional Pd(PPh₃)₄ (50 mg) and trimethylboroxine (0.200 mL) were added and reflux was continued for 28 hours. The reaction mixture was cooled to room temperature, filtered through Celite®, with THF washings, concentrated, and purified by flash chromatography on silica gel, eluting with 40% ethyl acetate/heptane to 100% ethyl acetate. Further purification by reverse-phase HPLC, eluting with 10% to 90% CH₃CN in water with 0.1% TFA, afforded the title compound as a white solid (0.025 g, 13%). ¹H-NMR (300 MHz, DMSO-d₆): δ 8.46 (d, J=2.0 Hz, 1H), 8.21 (d, J=7.0 Hz, 1H), 7.90-7.95 (m, 1H), 7.79 (d, J=7.9 Hz, 1H), 7.60-7.65 (m, 2H), 7.42-7.46 (m, 4H), 7.16 (d, J=8.1 Hz, 1H), 2.41 (s, 3H). MS (APCI) m/z: 348 (M+H)⁺.

Example 48

Preparation of 3-(4-chlorophenyl)-2-(6-(piperidin-1-yl)pyridin-3-yl)quinazolin-4(3H)-one

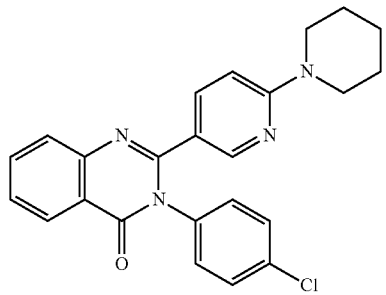 [SMILES: O=c1c2ccccc2nc(-c2ccc(N3CCCCC3)nc2)n1-c1ccc(Cl)cc1]

2-amino-N-(4-chlorophenyl)benzamide (0.318 g, 1.3 mmol) and 6-(piperidin-1-yl)nicotinaldehyde (1.3 mmol) were mixed in anhydrous EtOH (40 mL) and anhydrous CuCl₂ (0.524 g, 3.9 mmol) was added. The reaction mixture was heated at reflux for 5 hours, cooled to room temperature, and stirred overnight. The reaction mixture was concentrated, diluted with ethyl acetate (150 mL), washed with water (2×100 mL), dried (MgSO₄), filtered, and concentrated. Flash chromatograph on silica gel, eluting with 30% ethyl acetate/heptane to 75% ethyl acetate/heptane, afforded the title compound as a white solid (35%). ¹H-NMR (300 MHz, DMSO-d₆): δ 8.16 (d, J=8.0 Hz, 1H), 8.11 (d, J=2.4 Hz, 1H), 7.86-7.91 (m, 1H), 7.74 (d, J=8.0 Hz, 1H), 7.54-7.59 (m, 1H), 7.36-7.50 (m, 5H), 6.64 (d, J=9.0 Hz, 1H), 3.49-3.53 (m, 4H), 1.48-1.58 (m, 6H). MS (APCI) m/z: 417 (M+H)⁺.

Example 49

Preparation of 3-(4-sec-butylphenyl)-2-(6-(piperidin-1-yl)pyridin-3-yl)quinazolin-4(3H)-one

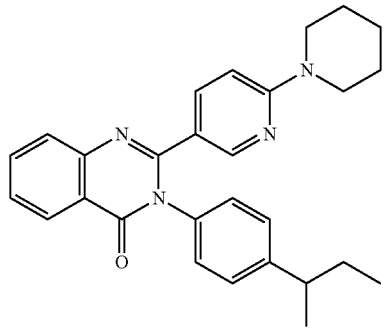 [SMILES: CCC(C)c1ccc(-n2c(-c3ccc(N4CCCCC4)nc3)nc3ccccc3c2=O)cc1]

2-amino-N-(4-sec-butylphenyl)benzamide (0.350 g, 1.3 mmol) and 6-(piperidin-1-yl)nicotinaldehyde (1.3 mmol) were mixed in anyhydrous EtOH (40 mL) and anyhydrous CuCl$_2$ (0.524 g, 3.9 mmol) was added. The reaction mixture was heated at reflux for 3 hours, cooled to room temperature, and stirred overnight. The reaction mixture was concentrated, diluted with ethyl acetate (150 mL), washed with water (2×100 mL), dried (MgSO$_4$), filtered, and concentrated. Flash chromatograph on silica gel, eluting with 30% ethyl acetate/heptane to 80% ethyl acetate/heptane, afforded the title compound as a white solid (35%) as a white solid. $^1$H-NMR (300 MHz, DMSO-d6): δ 8.14-8.17 (m, 1H), 8.05 (d, J=2.4 Hz, 1H), 7.85-7.90 (m, 1H), 7.74 (d, J=7.8 Hz, 1H), 7.53-7.58 (m, 1H), 7.35 (d, J=6.5 Hz, 1H), 7.17-7.24 (m, 4H), 6.55 (d, J=9.1 Hz, 1H), 3.40-3.49 (m, 4H), 2.57-2.66 (m, 1H), 1.44-1.64 (m, 8H), 1.19 (d, J=6.9 Hz, 3H), 0.68 (t, J=7.3 Hz, 3H). MS (APCI) m/z: 439 (M+H)$^+$.

Example 50

Preparation of 3-(4-chlorophenyl)-2-(6-phenoxypyridin-3-yl)quinazolin-4(3H)-one

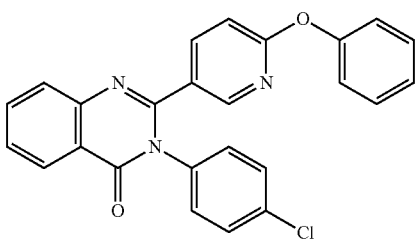 [SMILES: O=c1c2ccccc2nc(-c2ccc(Oc3ccccc3)nc2)n1-c1ccc(Cl)cc1]

Following the method described for Example 36, the title compound was made from 6-phenoxynicotinaldehyde in 31% yield. $^1$H-NMR (300 MHz, DMSO-d$_6$): δ 8.14-8.24 (m, 2H), 7.87-7.97 (m, 1H), 7.73-7.84 (m, 2H), 7.57-7.67 (m, 1H), 7.35-7.53 (m, 6H), 7.22 (t, J=7.4 Hz, 1H), 7.08 (d, J=7.6 Hz, 2H), 6.93 (d, J=8.5 Hz, 1H). MS (APCI) m/z: 426 (M+H)$^+$.

Example 51

Preparation of 3-(4-sec-butylphenyl)-2-(6-fluoropyridin-3-yl)quinazolin-4(3H)-one

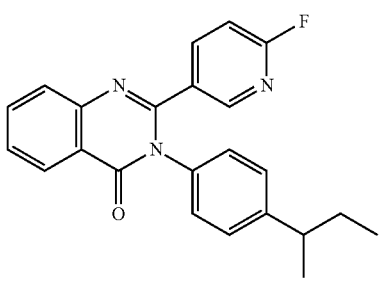

2-fluoro-5-formylpyridine (0.55 mmol) and anyhydrous CuCl$_2$ (0.150 g, 1.10 mmol) were added to a solution of 2-amino-N-(4-sec-butylphenyl)benzamide (0.205 g, 0.55 mmol) in anyhydrous EtOH (10 mL). After heating at reflux temperature for 2.5 hours, the mixture was concentrated in vacuo. The residue was dissolved in EtOAc and washed with H$_2$O, then brine, dried (Na$_2$SO$_4$), filtered, and concentrated in vacuo. Purification by flash chromatography on silica gel, eluting with 2% to 50% EtOAc in heptane, afforded the title compound as a white solid (15%). $^1$H-NMR (300 MHz, DMSO-d$_6$): δ 8.17-8.33 (m, 2H), 7.87-8.02 (m, 2H), 7.80 (d, J=8.1 Hz, 1H), 7.62-7.66 (m, 1H), 7.23-7.33 (m, 2H), 7.12-7.22 (m, 2H), 6.98-7.11 (m, 1H), 2.54-2.65 (m, 1H), 1.32-1.66 (m, 2H), 1.15 (d, J=6.9 Hz, 3H), 0.60 (t, J=7.4 Hz, 3H). MS (APCI) m/z: 374 (M+H)$^+$.

Example 52

Preparation of 3-(4-sec-butylphenyl)-2-(6-phenoxypyridin-3-yl)quinazolin-4(3H)-one

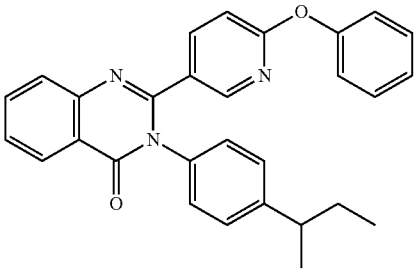 [SMILES: CCC(C)c1ccc(-n2c(-c3ccc(Oc4ccccc4)nc3)nc3ccccc3c2=O)cc1]

Following the method described for Example 51, the title compound was made from 6-phenoxynicotinaldehyde in 56% yield. $^1$H-NMR (300 MHz, DMSO-d$_6$): δ 8.20 (d, J=6.8 Hz, 1H), 8.11 (s, 1H), 7.87-7.99 (m, 1H), 7.78 (d, J=6.1 Hz, 2H), 7.57-7.68 (m, 1H), 7.32-7.42 (m, 2H), 7.15-7.31 (m, 5H), 6.95-7.02 (m, 2H), 6.86 (d, J=8.1 Hz, 1H), 2.54-2.65 (m, 1H), 1.38-1.61 (m, 2H), 1.16 (d, J=6.9 Hz, 3H), 0.65 (t, J=7.3 Hz, 3H). MS (APCI) m/z: 448 (M+H)$^+$.

Example 53

Preparation of 3-(4-chlorophenyl)-2-(6-(trifluoromethyl)pyridin-3-yl)quinazolin-4(3H)-one

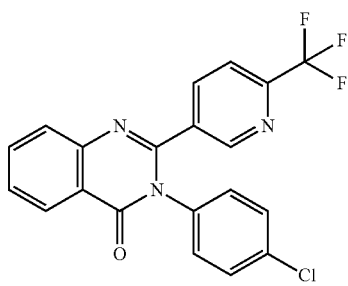 [SMILES: O=c1c2ccccc2nc(-c2ccc(C(F)(F)F)nc2)n1-c1ccc(Cl)cc1]

Following the method described for Example 36, the title compound was made from 6-(trifluoromethyl)nicotinaldehyde in 27% yield. $^1$H-NMR (300 MHz, DMSO-d$_6$): δ 8.82 (s, 1H), 8.24 (d, J=6.8 Hz, 1H), 8.07 (d, J=6.4 Hz, 1H), 7.80-7.97 (m, 3H), 7.63-7.72 (m, 1H), 7.44-7.51 (m, 4H). MS (APCI) m/z: 401 (M+H)$^+$.

Example 54

Preparation of 3-(4-sec-butylphenyl)-2-(6-(trifluoromethyl)pyridin-3-yl)quinazolin-4(3H)-one

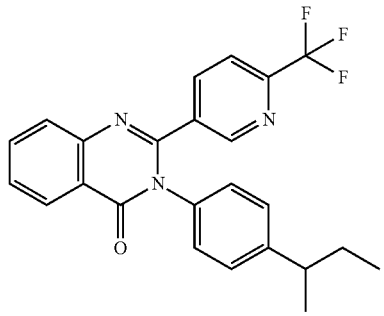 [SMILES: CCC(C)c1ccc(-n2c(-c3ccc(C(F)(F)F)nc3)nc3ccccc3c2=O)cc1]

Following the method described for Example 51, the title compound was made from 6-(trifluoromethyl)nicotinaldehyde in 9% yield. $^1$H-NMR (300 MHz, DMSO-$d_6$): δ 8.75 (s, 1H), 8.24 (d, J=6.8 Hz, 1H), 8.06 (d, J=6.4 Hz, 1H), 7.90-7.98 (m, 1H), 7.76-7.88 (m, 2H), 7.62-7.71 (m, 1H), 7.25-7.36 (m, 2H), 7.09-7.21 (m, 2H), 2.51-2.61 (m, 1H), 1.32-1.59 (m, 2H), 1.13 (d, J=6.9 Hz, 3H), 0.53 (t, J=7.3 Hz, 3H). MS (APCI) m/z: 424 (M+H)$^+$.

Example 55

Preparation of 3-(4-sec-butylphenyl)-2-(6-phenylpyridin-3-yl)quinazolin-4(3H)-one

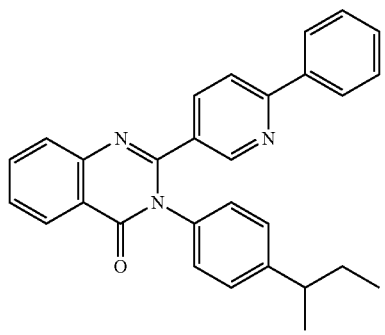 [SMILES: CCC(C)c1ccc(-n2c(-c3ccc(-c4ccccc4)nc3)nc3ccccc3c2=O)cc1]

Phenylboronic acid (0.041 g, 0.34 mmol) and Pd(PPh$_3$)$_4$ (0.003 g) were added to a mixture of 2-(6-bromopyridin-3-yl)-3-(4-sec-butylphenyl)quinazolin-4(3H)-one (0.150 g, 0.34 mmol) in 2 M Na$_2$CO$_3$ (0.3 mL) and DME (5 mL). After refluxing overnight, the reaction mixture was concentrated in vacuo. The residue was dissolved in CHCl$_3$ and washed with H$_2$O, then brine, dried (Na$_2$SO$_4$), filtered, and concentrated in vacuo. Purification by flash chromatography on silica gel, eluting with 0% to 20% of EtOAc in CH$_2$Cl$_2$, afforded the title compound as a white solid (0.050 g, 34%). $^1$H-NMR (300 MHz, DMSO-$d_6$): δ8.63 (s, 1H), 8.22 (d, J=7.0 Hz, 1H), 7.90-8.06 (m, 3H), 7.76-7.88 (m, 3H), 7.60-7.73 (m, 1H), 7.40-7.54 (m, 3H), 7.27-7.36 (m, 2H), 7.13-7.22 (m, 2H), 2.52-2.65 (m, 1H), 1.34-1.59 (m, 2H), 1.12 (d, J=6.9 Hz, 3H), 0.56 (t, J=7.3 Hz, 3H). MS (APCI) m/z: 432 (M+H)$^+$.

Example 56

Preparation of 3-(4-sec-butylphenyl)-2-(5-phenylpyridin-3-yl)quinazolin-4(3H)-one

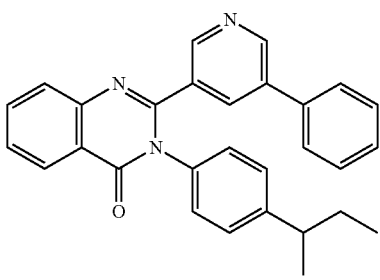 [SMILES: CCC(C)c1ccc(-n2c(-c3cncc(-c4ccccc4)c3)nc3ccccc3c2=O)cc1]

Phenylboronic acid (0.058 g, 0.48 mmol) and Pd(PPh$_3$)$_4$ (0.004 g) were added to a mixture of 2-(6-bromopyridin-3-yl)-3-(4-sec-butylphenyl)quinazolin-4(3H)-one (0.175 g, 0.40 mmol) in 2 M Na$_2$CO$_3$ (0.4 mL) and DME (15 mL). After refluxing for 5 hours, the reaction mixture was concentrated in vacuo. The residue was dissolved in CHCl$_3$ and washed with H$_2$O, then brine, dried (Na$_2$SO$_4$), filtered, and concentrated in vacuo. Purification by flash chromatography on silica gel, eluting with 0% to 60% of EtOAc in CH$_2$Cl$_2$, afforded the title compound as a white solid (0.080 g, 46%). $^1$H-NMR (300 MHz, DMSO-$d_6$): δ8.75 (s, 1H), 8.68 (s, 1H), 8.23 (d, J=8.0 Hz, 1H), 7.91-7.99 (m, 1H), 7.79-7.90 (m, 2H), 7.61-7.69 (m, 1H), 7.32-7.50 (m, 7H), 7.17-7.25 (m, 2H), 2.52-2.63 (m, 1H), 1.33-1.54 (m, 2H), 1.10 (d, J=6.9 Hz, 3H), 0.53 (t, J=7.3 Hz, 3H). MS (APCI) m/z: 432 (M+H)$^+$.

Example 57

Preparation of 2-(5-bromopyridin-3-yl)-3-(4-sec-butylphenyl)quinazolin-4(3H)-one

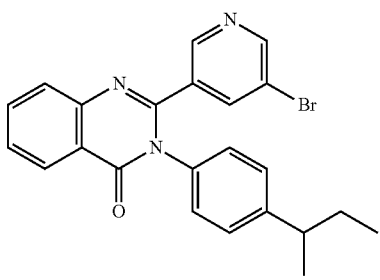

Following the method described for Example 51, the title compound was made from 5-bromo-3-formylpyridine in 57% yield. $^1$H-NMR (300 MHz, DMSO-$d_6$): δ8.59 (s, 1H), 8.58 (s, 1H), 8.23 (d, J=6.9 Hz, 1H), 7.88-8.03 (m, 2H), 7.82 (d, J=7.9 Hz, 1H), 7.65 (dd, J=7.9, 1.1 Hz, 1H), 7.26-7.36 (m, 2H), 7.13-7.25 (m, 2H), 2.54-2.65 (m, 1H), 1.35-1.66 (m, 2H), 1.16 (d, J=6.9 Hz, 3H), 0.65 (t, J=7.3 Hz, 3H). MS (APCI) m/z: 434 (M+H)$^+$.

Example 58

Preparation of 2-(5-bromopyridin-3-yl)-3-(4-chlorophenyl)quinazolin-4(3H)-one

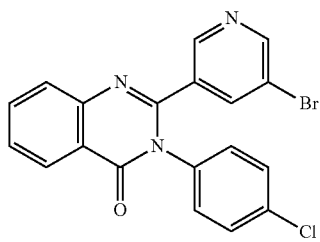 [SMILES: O=c1c2ccccc2nc(-c2cncc(Br)c2)n1-c1ccc(Cl)cc1]

Following the method described for Example 36, the title compound was made from 6-bromonicotinaldehyde in 26% yield. $^1$H-NMR (300 MHz, DMSO-d$_6$): δ8.64 (s, 1H), 8.56 (s, 1H), 8.23 (d, J=6.9 Hz, 1H), 8.10 (s, 1H), 7.90-8.01 (m, 1H), 7.81 (d, J=7.8 Hz, 1H), 7.63-7.73 (m, 1H), 7.43-7.52 (m, 4H). MS (APCI) m/z: 413 (M+H)$^+$.

Example 59

Preparation of 3-(4-sec-butylphenyl)-2-(5-(diethylamino)pyridin-3-yl)quinazolin-4(3H)-one

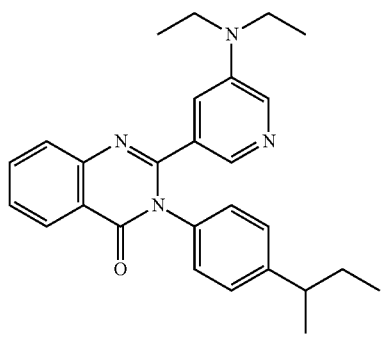 [SMILES: CCC(C)c1ccc(-n2c(-c3cncc(N(CC)CC)c3)nc3ccccc3c2=O)cc1]

Pd(OAc)$_2$ (0.026 g, 0.12 mmol), DPPF (0.055 g, 0.10 mmol) and NaOtBu (0.049 g, 0.52 mmol) were added to a mixture of 2-(5-bromopyridin-3-yl)-3-(4-sec-butylphenyl)quinazolin-4(3H)-one (0.175 g, 0.40 mmol) and Et$_2$NH (0.06 mL, 0.60 mmol) in toluene (2 mL). The mixture was microwaved at 90° C. and 300 W (max. power) with cooling for 3 hours, before being concentrated in vacuo. Purification by flash chromatography on silica gel, eluting with 5% to 60% EtOAc in heptane, plus further purification by flash chromatography on silica gel, eluting with 30% to 90% EtOAc in heptane, afforded the title compound as a white solid (0.010 g, 5%). $^1$H-NMR (300 MHz, DMSO-d$_6$): δ8.20 (d, J=6.9 Hz, 1H), 7.84-7.98 (m, 3H), 7.77 (d, J=7.9 Hz, 1H), 7.55-7.68 (m, 1H), 7.26 (d, J=7.8 Hz, 2H), 7.08-7.20 (m, 2H), 6.80 (s, 1H), 3.06-3.23 (m, 4H), 2.51-2.65 (m, 1H), 1.35-1.60 (m, 2H), 1.08-1.20 (m, 3H), 0.81-1.00 (m, 6H), 0.62 (t, J=7.3 Hz, 3H). MS (APCI) m/z: 427 (M+H)$^+$.

Example 60

Preparation of 3-(4-chlorophenyl)-2-(5-phenylpyridin-3-yl)quinazolin-4(3H)-one

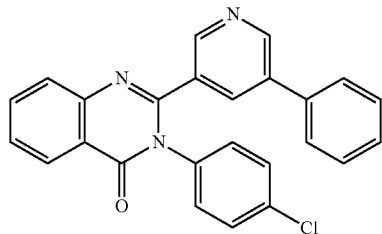 [SMILES: O=c1c2ccccc2nc(-c2cncc(-c3ccccc3)c2)n1-c1ccc(Cl)cc1]

Phenylboronic acid (0.067 g, 0.55 mmol) and Pd(PPh$_3$)$_4$ (0.005 g) were added to a mixture of 2-(5-bromopyridin-3-yl)-3-(4-chlorophenyl)quinazolin-4(3H)-one (0.190 g, 0.46 mmol) in 2 M Na$_2$CO$_3$ (0.5 mL) and DME (15 mL). After refluxing for 5 hours, the reaction mixture was concentrated in vacuo. The residue was dissolved in CHCl$_3$ and washed with H$_2$O, then brine, dried (Na$_2$SO$_4$), filtered, and concentrated in vacuo. Purification by flash chromatography on silica gel, eluting with 10% to 70% of EtOAc in heptane, afforded the title compound as a white solid (0.070 g, 37%). $^1$H-NMR (300 MHz, DMSO-d$_6$): δ8.81 (s, 1H), 8.58 (s, 1H), 8.24 (d, J=8.1 Hz, 1H), 8.02 (s, 1H), 7.90-7.98 (m, 1H), 7.83 (d, J=7.8 Hz, 1H), 7.61-7.70 (m, 1H), 7.43-7.58 (m, 9H). MS (APCI) m/z: 410 (M+H)$^+$.

Example 61

Preparation of 3-(4-chlorophenyl)-2-(5-(diethylamino)pyridin-3-yl)quinazolin-4(3H)-one

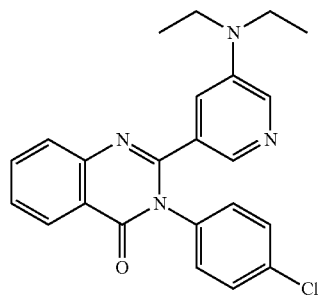 [SMILES: CCN(CC)c1cncc(-c2nc3ccccc3c(=O)n2-c2ccc(Cl)cc2)c1]

Pd(OAc)$_2$ (0.031 g, 0.14 mmol), DPPF (0.066 g, 0.12 mmol), and NaOtBu (0.059 g, 0.62 mmol) were added to a mixture of 2-(5-bromopyridin-3-yl)-3-(4-chlorophenyl)quinazolin-4(3H)-one (0.200 g, 0.48 mmol) and Et$_2$NH (0.07 mL) in toluene (2 mL). The reaction mixture was microwaved at 90° C. and 300 W (max. power) with cooling for 3 hours, before concentration in vacuo. Purification by flash chromatography on silica gel, eluting with 35% to 90% EtOAc in heptane, plus further purification by reverse-phase chromatography, eluting with 10% to 50% CH$_3$CN in H$_2$O, afforded the title compound as a white solid (0.02 g, 10%). $^1$H-NMR (300 MHz, DMSO-d$_6$): δ8.21 (d, J=6.6 Hz, 1H), 7.88-8.02

(m, 2H), 7.73-7.87 (m, 2H), 7.57-7.70 (m, 1H), 7.36-7.50 (m, 4H), 6.89 (s, 1H), 3.16-3.29 (m, 4H), 0.72-1.11 (m, 6H). MS (APCI) m/z: 405 (M+H)+.

Example 62

Preparation of 3-(4-cyclopentylphenyl)-2-(6-methylpyridin-3-yl)quinazolin-4(3H)-one

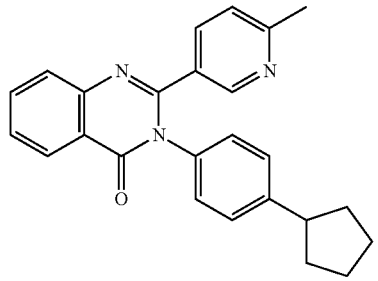 [SMILES: Cc1ccc(-c2nc3ccccc3c(=O)n2-c2ccc(C3CCCC3)cc2)cn1]

6-chloro-3-pyridinecarboxaldehyde (0.177 g, 1.20 mmol) and CuCl$_2$ (0.335 g, 2.40 mmol) were added to a solution of 2-amino-N-(4-cyclopentylphenyl)benzamide (0.350 g, 1.20 mmol) in EtOH (30 mL), and refluxed for 5 hours. The reaction mixture was concentrated in vacuo and the residue was dissolved in EtOAc. The organics were washed with H$_2$O, then brine, dried (Na$_2$SO$_4$), filtered, and concentrated in vacuo. Purification by flash chromatography on silica gel, eluting with 15% to 60% EtOAc in heptane, afforded 2-(6-chloropyridin-3-yl)-3-(4-cyclopentylphenyl)quinazolin-4(3H)-one (0.260 g, 54%). Pd(PPh$_3$)$_4$ (0.150 g, 0.12 mmol), K$_2$CO$_3$ (0.270 g, 1.90 mmol), and trimethylboroxine (0.18 mL, 1.20 mmol) were added to a solution of 2-(6-chloropyridin-3-yl)-3-(4-cyclopentylphenyl)quinazolin-4(3H)-one (0.260 g, 0.65 mmol) in dioxane (15 mL) and heated to reflux temperature for 20 minutes. The reaction mixture was filtered through Celite®, washed with EtOAc. The filtrate was concentrated and purified by flash chromatography on silica gel, eluting with 30% to 100% EtOAc in heptane, to afford the title compound as a white solid (0.068 g, 27%). $^1$H-NMR (300 MHz, DMSO-d$_6$): δ8.45 (s, 1H), 8.19 (d, J=7.4 Hz, 1H), 7.84-8.00 (m, 1H), 7.78 (d, J=7.9 Hz, 1H), 7.50-7.70 (m, 2H), 7.17-7.31 (m, 4H), 7.11 (d, J=8.0 Hz, 1H), 2.85-3.06 (m, 1H), 2.38 (s, 3H), 1.85-2.09 (m, 2H), 1.34-1.84 (m, 6H). MS (APCI) m/z: 382 (M+H)+.

Example 63

Preparation of 3-(4-sec-butylphenyl)-2-(6-(hydroxymethyl)pyridin-3-yl)quinazolin-4(3H)-one

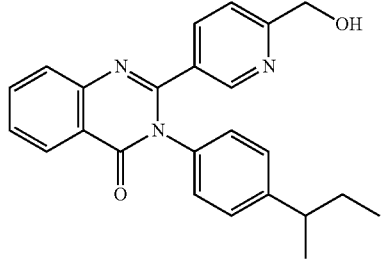 [SMILES: CCC(C)c1ccc(-n2c(-c3ccc(CO)nc3)nc3ccccc3c2=O)cc1]

Methyl 6-(hydroxymethyl)nicotinate (1.0 g, 6.0 mmol), 2,3-dihydropyran (1.5 mL, 16.5 mmol), and p-TsOH (1.14 g, 6.0 mmol) were combined in CH$_2$Cl$_2$ (100 mL) and stirred at room temperature for 18 hours. An additional 1 mL of 2,3-dihyropyran was added and the reaction was continued at room temperature for 24 hours. The reaction mixture was washed with water (200 mL), dried (MgSO$_4$), filtered, and concentrated, to afford methyl 6-((tetrahydro-2H-pyran-2-yloxy)methyl)nicotinate (1.5 g, quantitative).

Methyl 6-((tetrahydro-2H-pyran-2-yloxy)methyl)nicotinate (1.5 g, 6.0 mmol) was dissolved in THF (30 mL) and cooled to 0° C. under nitrogen. DIBAL-H (1.0 M in THF, 21 mL, 21 mmol) was added dropwise, via a syringe over 5 min, and stirred for 90 min. The reaction mixture was warmed to room temperature, and quenched with water (25 mL), followed by saturated NH$_4$Cl (10 mL). After stirring for 10 minutes, the mixture was basified with solid KOH, extracted with CH$_2$Cl$_2$ (2×100 mL), washed with brine (100 mL), dried (MgSO$_4$), filtered, and concentrated, to afford (6-((tetrahydro-2H-pyran-2-yloxy)methyl)pyridin-3-yl)methanol as a yellow oil (1.3 g, 97%).

(6-((tetrahydro-2H-pyran-2-yloxy)methyl)pyridin-3-yl)methanol (1.3 g, 6.0 mmol) was dissolved in CH$_2$Cl$_2$ (80 mL) and NMO (0.846 g, 7.2 mmol) and TPAP (0.210 g, 0.6 mmol) were added. After stirring at room temperature for 20 minutes, the reaction mixture was filtered through Celite®, and the filtrate was concentrated. Purification of the residue by flash chromatography on silica gel, eluting with 30% ethyl acetate/heptane to 75% ethyl acetate/heptane, afforded 6-((tetrahydro-2H-pyran-2-yloxy)methyl)nicotinaldehyde as a yellow oil (0.560 g, 42%).

2-amino-N-(4-sec-butylphenyl)benzamide (0.250 g, 0.92 mmol) and 6-((tetrahydro-2H-pyran-2-yloxy)methyl)nicotinaldehyde (0.77 mmol) were mixed in anyhydrous EtOH (40 mL) and anyhydrous CuCl$_2$ (0.310 g, 2.3 mmol) was added. After heating at reflux for 1.5 hours, and concentrating, ethyl acetate (150 mL) was added, the mixture was washed with water (2×125 mL), dried (MgSO$_4$), filtered, and concentrated. Flash chromatograph on silica gel, eluting with 50% ethyl acetate/heptane to 100% ethyl acetate, plus re-chromatographing with 30% ethyl acetate/CH$_2$Cl$_2$ to 100% ethyl acetate, afforded the title compound as a white solid (40%). $^1$H-NMR (300 MHz, DMSO-d$_6$): δ8.47 (d, J=1.6 Hz, 1H), 8.21 (d, J=7.8 Hz, 1H), 7.89-7.94 (m, 1H), 7.79 (d, J=7.9 Hz, 1H), 7.60-7.72 (m, 2H), 7.26-7.29 (m, 3H), 7.14-7.18 (m, 2H), 5.42 (t, J=5.8 Hz, 1H), 4.45 (d, J=5.7 Hz, 2H), 2.55-2.64 (m, 1H), 1.37-1.58 (m, 2H), 1.15 (d, J=6.9 Hz, 3H), 0.64 (t, J=7.3 Hz, 3H). MS (APCI) m/z: 386 (M+H)+.

Example 64

Preparation of 2-(6-methylpyridin-3-yl)-3-(4-(methylthio)phenyl)quinazolin-4(3H)-one

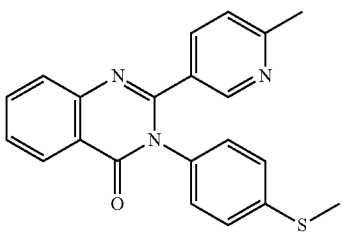 [SMILES: CSc1ccc(-n2c(-c3ccc(C)nc3)nc3ccccc3c2=O)cc1]

A mixture of 6-methylnicotinaldehyde (0.36 g, 3.0 mmol), 2-amino-N-(4-(methylthio)phenyl)benzamide (3.0 mmol), and anyhydrous CuCl$_2$ (0.80 g, 6.0 mmol) in anyhydrous EtOH was refluxed for 6 hours. After concentration in vacuo, the residue was redissolved in EtOAc and washed with H$_2$O, then brine, dried (Na$_2$SO$_4$), filtered, and concentrated in vacuo. Purification by flash chromatography on silica gel, eluting with 0% to 20% MeOH in CH$_2$Cl$_2$, followed by 40% to 100% of 92:7:1 CHCl$_3$/MeOH/concentrate NH$_4$OH in CH$_2$Cl$_2$, afforded the title compound (19%). $^1$H-NMR (300 MHz, DMSO-d$_6$): δ8.42 (s, 1H), 8.20 (d, J=7.9 Hz, 1H), 7.87-7.97 (m, 1H), 7.78 (d, J=8.1 Hz, 1H), 7.56-7.73 (m, 2H), 7.31 (d, J=8.3 Hz, 2H), 7.10-7.26 (m, 3H), 2.43 (s, 3H), 2.41 (s, 3H). MS (APCI) m/z: 360 (M+H)$^+$.

Example 65

Preparation of 3-(4-isopropylphenyl)-2-(6-methylpyridin-3-yl)quinazolin-4(3H)-one

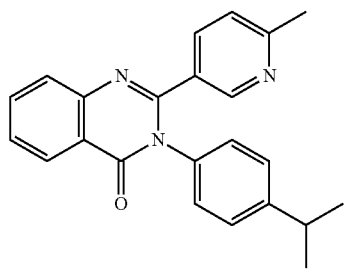 [SMILES: Cc1ccc(-c2nc3ccccc3c(=O)n2-c2ccc(C(C)C)cc2)cn1]

Following the method described for Example 64, the title compound was made from 2-amino-N-(4-isopropylphenyl)benzamide in 33% yield. $^1$H-NMR (300 MHz, DMSO-d$_6$): δ8.45 (s, 1H), 8.18 (d, J=7.9 Hz, 1H), 7.82-7.99 (m, 1H), 7.77 (d, J=7.7 Hz, 1H), 7.50-7.67 (m, 2H), 7.15-7.34 (m, 4H), 7.10 (d, J=8.1 Hz, 1H), 2.74-2.94 (m, 1H), 2.38 (s, 3H), 1.15 (d, J=6.9 Hz, 6H). MS (APCI) m/z: 356 (M+H)$^+$.

Example 66

Preparation of N-(4-(2-(6-methylpyridin-3-yl)-4-oxoquinazolin-3(4H)-yl)phenyl)methanesulfonamide

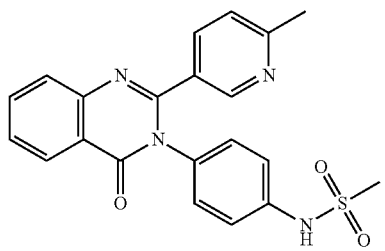 [SMILES: Cc1ccc(-c2nc3ccccc3c(=O)n2-c2ccc(NS(C)(=O)=O)cc2)cn1]

N-(4-(2-(6-methylpyridin-3-yl)-4-oxoquinazolin-3(4H)-yl)phenyl)acetamide (0.130 g, 0.33 mmol) was refluxed in 2 N HCl for 1 hour. The mixture was cooled to room temperature and basified with 1 N NaOH, and extracted with CH$_2$Cl$_2$. The organics were washed with brine, dried (Na$_2$SO$_4$), filtered, and concentrated in vacuo, to afford 3-(4-aminophenyl)-2-(6-methylpyridin-3-yl)quinazolin-4(3H)-one (0.110 g, quantitative).

Methanesulfonyl chloride (0.026 mL, 0.33 mmol) was added to a mixture of 3-(4-aminophenyl)-2-(6-methylpyridin-3-yl)quinazolin-4(3H)-one (0.11 g, 0.33 mmol) and TEA (0.093 mL, 0.67 mmol) in CH$_2$Cl$_2$ (5 mL). The mixture was stirred for 2 hours and concentrated in vacuo. The residue was redissolved in 1:1 dioxane and H$_2$O (5 mL) and LiOH.H$_2$O (0.050 g, 1.2 mmol) was added. The mixture was stirred at room temperature for 20 minutes, then extracted with EtOAc. The organics were washed with brine, dried (Na$_2$SO$_4$), filtered, and concentrated in vacuo. Purification was conducted by flash chromatography on silica gel, eluting with 10% to 80% of 92:7:1 CHCl$_3$/MeOH/concentrated NH$_4$OH in CH$_2$Cl$_2$, followed by further purification by reverse-phase chromatography, eluting with 10% to 50% CH$_3$CN in H$_2$O with 0.1% TFA. The desired fractions were basified and extracted to afford the title compound as a white solid (0.075 g, 56%). $^1$H-NMR (300 MHz, DMSO-d$_6$): δ9.91 (s, 1H), 8.43 (s, 1H), 8.20 (d, J=8.0 Hz, 1H), 7.85-7.98 (m, 1H), 7.78 (d, J=8.1 Hz, 1H), 7.54-7.69 (m, 2H), 7.33 (d, J=8.7 Hz, 2H), 7.05-7.22 (m, 3H), 2.97 (s, 3H), 2.39 (s, 3H). MS (APCI) m/z: 407 (M+H)$^+$.

Example 67

Preparation of 3-(4-sec-butylphenyl)-2-(6-(morpholinomethyl)pyridin-3-yl)quinazolin-4(3H)-one

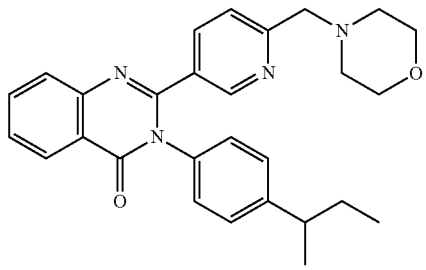 [SMILES: CCC(C)c1ccc(-n2c(-c3ccc(CN4CCOCC4)nc3)nc3ccccc3c2=O)cc1]

3-(4-sec-butylphenyl)-2-(6-(hydroxymethyl)pyridin-3-yl)quinazolin-4(3H)-one (0.176 g, 0.46 mmol) was dissolved in CH$_2$Cl$_2$ (30 mL) under nitrogen and cooled to 0° C. Hünig's base (0.160 mL, 0.92 mmol) was added, followed by MsCl (0.042 mL, 0.55 mmol), and the mixture was stirred for 15 min at 0° C. Morpholine (0.400 mL) was added, the reaction was warmed to room temperature, and stirred for 2 hours, before concentration and purification by flash chromatography on silica gel, eluting with 100% ethyl acetate to 10% methanol/ethyl acetate, afforded the title compound (0.175 g, 984%). $^1$H-NMR (300 MHz, DMSO-d$_6$): δ8.48 (s, 1H), 8.22 (d, J=7.9 Hz, 1H), 7.90-7.95 (m, 1H), 7.79 (d, J=8.1 Hz, 1H), 7.60-7.68 (m, 2H), 7.22-7.27 (m, 3H), 7.10-7.16 (m, 2H), 3.49-3.54 (m, 6H), 2.55-2.63 (m, 1H), 2.19-2.29 (m, 4H), 1.33-1.56 (m, 2H), 1.13 (d, J=6.8 Hz, 3H), 0.62 (t, J=7.2 Hz, 3H). MS (APCI) m/z: 455 (M+H)$^+$.

Example 68

Preparation of 3-(4-cyclopropylphenyl)-2-(6-methylpyridin-3-yl)quinazolin-4(3H)-one

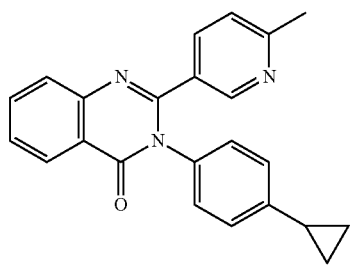 [SMILES: Cc1ccc(-c2nc3ccccc3c(=O)n2-c2ccc(C3CC3)cc2)cn1]

Isatoic anhydride (0.393 g, 2.41 mmol) and 4-cyclopropylaniline (0.320 g, 2.41 mmol) were dissolved in DMF (5 mL) and heated at 135° C. for 5 hours. The reaction mixture was concentrated, and purified by silica gel chromatography, eluting with 30% ethyl acetate/heptane to 100% ethyl acetate, to afford 2-amino-N-(4-cyclopropylphenyl)benzamide as a white solid (0.342 g, 56%).

2-amino-N-(4-cyclopropylphenyl)benzamide (0.342 g, 1.36 mmol), 6-methylnicotinaldehyde (0.197 g, 1.63 mmol), and anyhydrous $CuCl_2$ (0.547 g, 4.08 mmol) were combined in anyhydrous EtOH (30 mL) and heated at reflux for 2.5 hours. After concentration, ethyl acetate (200 mL) was added, and the mixture was washed with water (2×100 mL), dried ($MgSO_4$), filtered, and concentrated. Purification by flash chromatography on silica gel, eluting with 20% ethyl acetate/hexanes to 30% ethyl acetate/hexanes to 100% ethyl acetate, plus further purification by flash chromatography on silica gel, eluting with 1:1 ethyl acetate/$CH_2Cl_2$, afford the title compound as a white solid (0.070 g, 15%). $^1$H-NMR (300 MHz, DMSO-$d_6$): δ8.44 (d, J=2.0 Hz, 1H), 8.18-8.20 (m, 1H), 7.88-7.94 (m, 1H), 7.77 (d, J=7.6 Hz, 1H), 7.58-7.65 (m, 2H), 7.22 (d, J=8.4 Hz, 2H), 7.13 (d, J=8.1 Hz, 1H), 7.04 (d, J=8.4 Hz, 2H), 2.40 (s, 3H), 1.84-1.91 (m, 1H), 0.91-0.99 (m, 2H), 0.63-0.68 (m, 2H). MS (APCI) m/z: 354 (M+H)$^+$.

Example 69

Preparation of 3-(4-(dimethylamino)phenyl)-2-(6-methylpyridin-3-yl)quinazolin-4(3H)-one

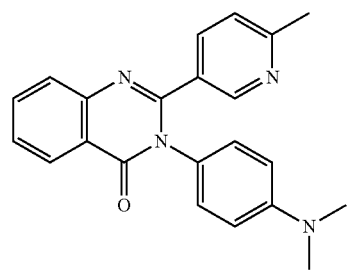 [SMILES: Cc1ccc(-c2nc3ccccc3c(=O)n2-c2ccc(N(C)C)cc2)cn1]

Hünig's base (0.24 mL, 1.3 mmol), followed by iodomethane (0.057 mL, 0.91 mmol), was added to a solution of 3-(4-aminophenyl)-2-(6-methylpyridin-3-yl)quinazolin-4 (3H)-one (0.15 g, 0.46 mmol) in DMF (10 mL). After stirring at reflux temperature and adding another equivalent of iodomethane (0.026 mL, 0.45 mmol), after 2 hours, the mixture was concentrated in vacuo and purified by flash chromatography on silica gel, eluting with 1% to 8% MeOH in $CH_2Cl_2$. Further purification was effected by reverse-phase chromatography, eluting with 10% to 50% $CH_3CN$ in $H_2O$ with 0.1% TFA. The desired fractions were basified and extracted to afford the title compound as a light-yellow solid (0.040 g, 24%). 1H-NMR (300 MHz, DMSO-$d_6$): δ8.46 (s, 1H), 8.18 (d, J=7.8 Hz, 1H), 7.85-7.94 (m, 1H), 7.76 (d, J=7.7 Hz, 1H), 7.54-7.70 (m, 2H), 7.06-7.18 (m, 3H), 6.60 (d, J=8.9 Hz, 2H), 2.88 (s, 6H), 2.40 (s, 3H). MS (APCI) m/z: 357 (M+H)$^+$.

Example 70

Preparation of 2-(6-chloropyridin-3-yl)-3-(4-cyclopropylphenyl)quinazolin-4(3H)-one

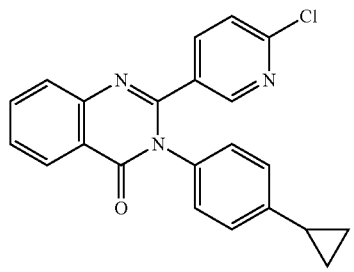 [SMILES: O=c1c2ccccc2nc(-c2ccc(Cl)nc2)n1-c1ccc(C2CC2)cc1]

Following the method described for compound Example 68, the title compound was made from 6-chloronicotinaldehyde in 62% yield and isolated as a white solid. $^1$H-NMR (300 MHz, DMSO-$d_6$): δ8.43 (d, J=2.1 Hz, 1H), 8.21 (d, J=8.0 Hz, 1H), 7.90-7.96 (m, 1H), 7.78-7.85 (m, 2H), 7.61-7.66 (m, 1H), 7.46 (d, J=8.3 Hz, 1H), 7.25 (d, J=8.3 Hz, 2H), 7.06 (d, J=8.4 Hz, 2H), 1.87-1.92 (m, 1H), 0.93-0.99 (m, 2H), 0.64-0.69 (m, 2H). MS (APCI) m/z: 374 (M+H)$^+$.

Example 71

Preparation of 3-(4-sec-butylphenyl)-2-(6-morpholinopyridin-3-yl)quinazolin-4(3H)-one

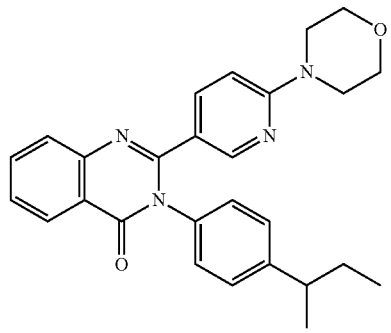 [SMILES: CCC(C)c1ccc(-n2c(-c3ccc(N4CCOCC4)nc3)nc3ccccc3c2=O)cc1]

Following the method described for Example 51, the title compound was made from 6-morpholinonicotinaldehyde in 47% yield. $^1$H-NMR (300 MHz, DMSO-$d_6$): δ8.17 (d, J=6.9 Hz, 1H), 8.10 (s, 1H), 7.86-7.90 (m, 1H), 7.74 (d, J=7.9 Hz, 1H), 7.55-7.57 (m, 1H), 7.42 (d, J=6.6 Hz, 1H), 7.14-7.32 (m, 4H), 6.58 (d, J=9.0 Hz, 1H), 3.55-3.69 (m, 4H), 3.36-3.47 (m, 4H), 2.56-2.66 (m, 1H), 1.35-1.67 (m, 2H), 1.18 (d, J=6.9 Hz, 3H), 0.66 (t, J=7.4 Hz, 3H). MS (APCI) m/z: 441 (M+H)+.

Example 72

Preparation of 3-(4-sec-butylphenyl)-2-(1H-indazol-5-yl)quinazolin-4(3H)-one

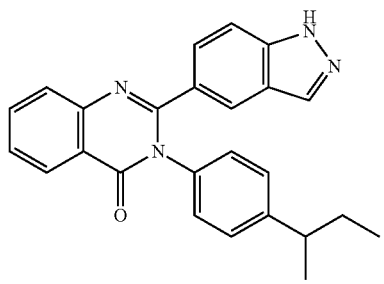 [SMILES: CCC(C)c1ccc(-n2c(-c3ccc4[nH]ncc4c3)nc3ccccc3c2=O)cc1]

Following the method described for Example 45, the title compound was made from 1H-indazole-5-carbaldehyde in 15% yield and isolated as a white solid. $^1$H-NMR (300 MHz, DMSO-d$_6$): δ13.10 (br s, 1H), 8.21 (d, J=7.0 Hz, 1H), 8.00 (s, 1H), 7.88-7.93 (m, 1H), 7.71-7.85 (m, 2H), 7.57-7.69 (m, 1H), 7.10-7.33 (m, 6H), 2.57-2.64 (m, 1H), 1.25-1.53 (m, 2H), 1.11 (d, J=6.9 Hz, 3H), 0.56 (t, J=7.3 Hz, 3H). MS (APCI) m/z: 395 (M+H)+.

Example 73

Preparation of 3-(4-chlorophenyl)-2-(1H-indol-5-yl)quinazolin-4(3H)-one

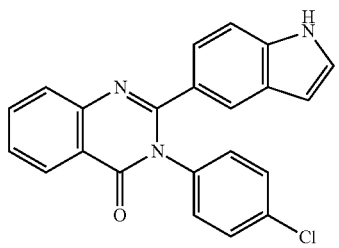 [SMILES: O=c1c2ccccc2nc(-c2ccc3[nH]ccc3c2)n1-c1ccc(Cl)cc1]

3-methyl-4-nitro-benzaldehyde (0.268 g, 1.60 mmol) and anyhydrous CuCl$_2$ (0.437 g, 3.20 mmol) were added to a solution of 2-amino-N-(4-chlorophenyl)benzamide (0.400 g, 1.60 mmol) in anyhydrous EtOH (15 mL) and heated at reflux temperature for 3.5 hours. After concentration in vacuo and dissolving the residue in EtOAc, the organics were washed with H$_2$O, then brine, dried (Na$_2$SO$_4$), filtered, and concentrated in vacuo. Purification by flash chromatography on silica gel, eluting with 10% to 70% EtOAc in heptane, afforded 3-(4-chlorophenyl)-2-(3-methyl-4-nitrophenyl)quinazolin-4(3H)-one (0.300 g, 48%).

tert-butoxybis(dimethylamino)methane (0.47 mL, 2.30 mmol) was added to a solution of 3-(4-chlorophenyl)-2-(3-methyl-4-nitrophenyl)quinazolin-4(3H)-one (0.300 g, 0.76 mmol) in DMF (30 mL). After heating at 40° C. for 3.5 hours, concentration in vacuo afforded (E)-3-(4-Chlorophenyl)-2-(3-(2-(dimethylamino)vinyl)-4-nitrophenyl)quinazolin-4(3H)-one (0.342 g, 100%).

Zn dust (0.220 g, 3.35 mmol) was added to a solution of (E)-3-(4-chlorophenyl)-2-(3-(2-(dimethylamino)vinyl)-4-nitrophenyl)quinazolin-4(3H)-one in AcOH (15 mL). After heating and stirring at reflux temperature for 4 hours, the mixture was basified with 1N NaOH and extracted with EtOAc. The organics were washed with brine, dried (Na$_2$SO$_4$), filtered, and concentrated in vacuo. Purification by flash chromatography on silica gel, eluting with 20% to 90% EtOAc in heptane, afford the title compound as a white solid (0.048 g, 39%). $^1$H-NMR (300 MHz, DMSO-d$_6$): δ11.19 (s, 1H), 8.18-8.21 (m, 1H), 7.88-8.00 (m, 1H), 7.75 (d, J=7.7 Hz, 1H), 7.47-7.70 (m, 2H), 7.30-7.44 (m, 5H), 7.20 (d, J=8.4 Hz, 1H), 7.06 (d, J=6.8 Hz, 1H), 6.40 (d, J=2.0 Hz, 1H). MS (APCI) m/z: 372 (M+H)+.

Example 74

Preparation of 3-(4-sec-butylphenyl)-2-(1H-indol-5-yl)quinazolin-4(3H)-one

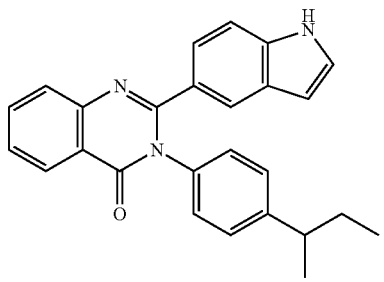 [SMILES: CCC(C)c1ccc(-n2c(-c3ccc4[nH]ccc4c3)nc3ccccc3c2=O)cc1]

Following the method described for Example 73, 3-(4-sec-butylphenyl)-2-(3-methyl-4-nitrophenyl)quinazolin-4(3H)-one was made from 2-amino-N-(4-sec-butylphenyl)benzamide in 66% yield.

Following the method described for Example 73, (E)-3-(4-sec-butylphenyl)-2-(3-(2-(dimethylamino)vinyl)-4-nitrophenyl)quinazolin-4(3H)-one was made from 3-(4-sec-butylphenyl)-2-(3-methyl-4-nitrophenyl)quinazolin-4(3H)-one in quantitative yield.

Following the method described for Example 73, the title compound was made from (E)-3-(4-sec-butylphenyl)-2-(3-(2-(dimethylamino)vinyl)-4-nitrophenyl)quinazolin-4(3H)-one in 16% yield. $^1$H-NMR (300 MHz, DMSO-d$_6$): δ11.14 (s, 1H), 8.15-8.19 (m, 1H), 7.87-8.00 (m, 1H), 7.75 (d, J=7.7 Hz, 1H), 7.51-7.66 (m, 2H), 7.24-7.33 (m, 1H), 6.98-7.24 (m, 6H), 6.33 (d, J=2.1 Hz, 1H), 2.51-2.57 (m, 1H), 1.26-1.62 (m, 2H), 1.12 (d, J=6.9 Hz, 3H), 0.60 (t, J=7.3 Hz, 3H). MS (APCI) m/z: 394 (M+H)+.

Example 75

Preparation of 3-(4-sec-butylphenyl)-2-(2-(hydroxymethyl)-1H-benzo[d]imidazol-6-yl)quinazolin-4(3H)-one

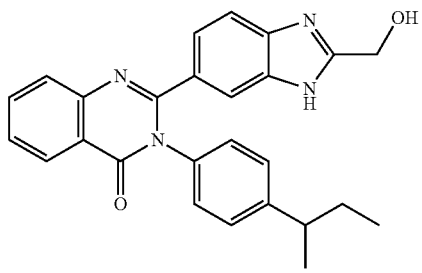 [SMILES: CCC(C)c1ccc(-n2c(-c3ccc4nc(CO)[nH]c4c3)nc3ccccc3c2=O)cc1]

Anhydrous CuCl₂ (0.370 g, 2.70 mmol) and 3,4-dinitrobenzaldehyde (0.270 g, 1.38 mmol) were added to a solution of 2-amino-N-(4-sec-butylphenyl)benzamide (0.370 g, 1.38 mmol) in anhydrous EtOH (20 mL). After heating to reflux temperature for 3 hours, the mixture was concentrated in vacuo. The residue was dissolved in EtOAc, washed with H₂O, then brine, dried (Na₂SO₄), filtered, and concentrated in vacuo. Purification by flash chromatography on silica gel, eluting with 10% to 60% EtOAc in heptane, afforded 3-(4-sec-butylphenyl)-2-(3,4-dinitrophenyl)quinazolin-4(3H)-one (0.300 g, 49%).

3-(4-sec-butylphenyl)-2-(3,4-dinitrophenyl)quinazolin-4(3H)-one (0.240 g, 0.54 mmol) was dissolved in EtOH (20 mL) and flushed with N₂ for 15 minutes. Pd/C (0.025 g, 10 wt %) was added, and stirred under 1 atmosphere of H₂ overnight. After flushing with N₂, the mixture was filtered through diatomaceous earth. The filtrate was concentrated and purified by flash chromatography on silica gel, eluting with 0% to 10% MeOH in EtOAc, to afford 3-(4-sec-butylphenyl)-2-(3,4-diaminophenyl)quinazolin-4(3H)-one (0.130 g, 62%).

A solution of 3-(4-sec-butylphenyl)-2-(3,4-diaminophenyl)quinazolin-4(3H)-one (0.130 g, 0.34 mmol) was refluxed in a 70% aqueous solution of glycolic acid (10 mL) for 2 hours. The reaction was poured into a saturated solution of NaHCO₃ and extracted with EtOAc. The organics were washed with brine, dried (Na₂SO₄), filtered, and concentrated in vacuo. Purification by flash chromatography on silica gel, eluting with 3% to 10% MeOH in CH₂Cl₂, afforded the title compound as a white solid (0.060 g, 41%). ¹H-NMR (300 MHz, DMSO-d₆): δ12.22-12.53 (m, 1H), 8.19 (d, J=7.5 Hz, 1H), 7.87-7.92 (m, 1H), 7.76 (d, J=8.0 Hz, 1H), 7.56-7.61 (m, 2H), 7.00-7.26 (m, 6H), 5.67-5.69 (m, 1H), 4.51-4.71 (m, 2H), 1.37-1.50 (m, 2H), 1.11 (d, J=6.8 Hz, 3H), 0.58 (t, J=7.2 Hz, 3H). MS (APCI) m/z: 425 (M+H)⁺.

Example 76

Preparation of 2-(1H-indol-5-yl)-3-(4-(trifluoromethoxy)phenyl)quinazolin-4(3H)-one

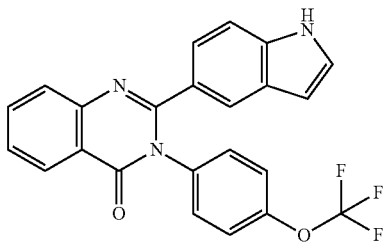 [SMILES: O=c1c2ccccc2nc(-c2ccc3[nH]ccc3c2)n1-c1ccc(OC(F)(F)F)cc1]

Following the method described for Example 73, 2-(3-methyl-4-nitrophenyl)-3-(4-(trifluoromethoxy)phenyl)quinazolin-4(3H)-one was made from 2-amino-N-(4-(trifluoromethoxy)phenyl)benzamide in 58% yield and isolated as a white solid.

Following the method described for Example 73, 2-(3-(2-(dimethylamino)vinyl)-4-nitrophenyl)-3-(4-(trifluoromethoxy)phenyl)quinazolin-4(3H)-one was made from 2-(3-methyl-4-nitrophenyl)-3-(4-(trifluoromethoxy)phenyl)quinazolin-4(3H)-one in quantitative yield and isolated as a red solid.

Following the method described for Example 73, the title compound was made from 2-(3-(2-(dimethylamino)vinyl)-4-nitrophenyl)-3-(4-(trifluoromethoxy)phenyl)quinazolin-4(3H)-one in 16% yield and isolated as a white solid. ¹H-NMR (300 MHz, DMSO-d₆): δ11.19 (s, 1H), 8.20 (d, J=7.8 Hz, 1H), 7.88-7.93 (m, 1H), 7.77 (d, J=8.2 Hz, 1H), 7.56-7.63 (m, 2H), 7.49 (d, J=8.7 Hz, 2H), 7.28-7.35 (m, 3H), 7.19 (d, J=8.5 Hz, 1H), 7.05 (d, J=8.4 Hz, 1H), 6.38 (s, 1H). MS (APCI) m/z: 422 (M+H)⁺.

Example 77

Preparation of 2-(1H-indol-5-yl)-3-(4-isopropylphenyl)quinazolin-4(3H)-one

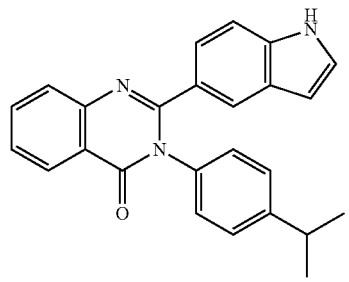 [SMILES: CC(C)c1ccc(-n2c(-c3ccc4[nH]ccc4c3)nc3ccccc3c2=O)cc1]

Following the method described for Example 73, 3-(4-isopropylphenyl)-2-(3-methyl-4-nitrophenyl)quinazolin-4(3H)-one was made from 2-amino-N-(4-isopropylphenyl)benzamide in 55% yield.

Following the method described for Example 73, (E)-2-(3-(2-(dimethylamino)vinyl)-4-nitrophenyl)-3-(4-isopropylphenyl)quinazolin-4(3H)-one was made from 3-(4-isopropylphenyl)-2-(3-methyl-4-nitrophenyl)quinazolin-4(3H)-one in quantitative yield.

Following the method described for Example 73, the title compound was made from (E)-3-(4-isopropylphenyl)-2-(3-(2-(dimethylamino)vinyl)-4-nitrophenyl)-quinazolin-4(3H)-one in 23% yield. ¹H-NMR (300 MHz, DMSO-d₆): δ11.15 (s, 1H), 8.18 (d, J=7.9 Hz, 1H), 7.86-7.91 (m, 1H), 7.74 (d, J=7.9 Hz, 1H), 7.54-7.62 (m, 2H), 7.32 (s, 1H), 7.05-7.22 (m, 6H), 6.36 (s, 1H), 2.77-2.86 (m, 1H), 1.12 (d, J=6.9 Hz, 6H). MS (ESI): 380 (M+H)⁺.

Example 78

Preparation of 3-(4-chlorophenyl)-2-(1-(4-methoxyphenylsulfonyl)-1H-pyrrolo[2,3-b]pyridin-5-yl)quinazolin-4(3H)-one

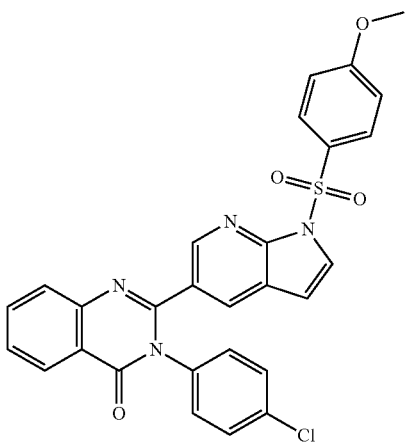 [SMILES: COc1ccc(S(=O)(=O)n2ccc3cc(-c4nc5ccccc5c(=O)n4-c4ccc(Cl)cc4)cnc32)cc1]

3-(4-chlorophenyl)-2-(1H-pyrrolo[2,3-b]pyridin-5-yl)quinazolin-4(3H)-one (0.156 g, 0.42 mmol) and benzyltriethylammonium chloride (0.003 g, 0.013 mmol) were combined in CH₂Cl₂ (10 mL). NaOH powder (0.052 g, 1.31 mmol) was added and the mixture was cool to 0° C. 4-methoxy-benzenesulfonyl chloride (0.107 g, 0.52 mmol) was added, and the reaction mixture was stirred for 30 minutes at 0° C., and warmed to room temperature. After 18 hours, additional NaOH powder (0.050 gm 1.30 mmol), benzyltriethylammonium chloride (0.010 g, 0.04 mmol), and 4-methoxy-benzenesulfonyl chloride (0.200 g, 0.97 mmol) were added and the reaction was continued at room temperature for an additional 6 hours. After concentration and purification by silica gel chromatography, eluting with 100% CH$_2$Cl$_2$ to 100% ethyl acetate to 50% methanol/ethyl acetate, the title compound was afforded as a white solid (0.137 g, 60%). $^1$H-NMR (300 MHz, DMSO-d$_6$): δ8.37 (d, 1.7 Hz, 1H), 8.22 (d, J=8.0 Hz, 1H), 8.07 (d, J=1.7 Hz, 1H), 7.98 (d, J=8.9 Hz, 2H), 7.88-7.93 (m, 2H), 7.76 (d, J=8.0 Hz, 1H), 7.61-7.66 (m, 1H), 7.34-7.45 (m, 4H), 7.11 (d, J=9.0 Hz, 2H), 6.79 (d, J=3.9 Hz, 1H), 3.82 (s, 3H). MS (APCI) m/z: 543 (M+H)$^+$.

Example 79

Preparation of 3-(4-chlorophenyl)-2-(1-(4-fluorophenylsulfonyl)-1H-pyrrolo[2,3-b]pyridin-5-yl)quinazolin-4(3H)-one

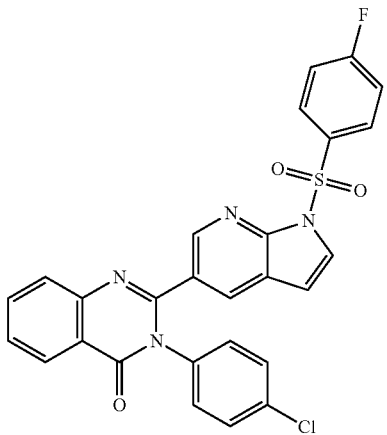 [SMILES: O=c1c2ccccc2nc(-c2cnc3c(ccn3S(=O)(=O)c3ccc(F)cc3)c2)n1-c1ccc(Cl)cc1]

Following the method described for Example 78, the title compound was made from 4-fluorobenzenesulfonyl chloride in 90% yield and isolated as a white solid. $^1$H-NMR (500 MHz, DMSO-d$_6$): δ8.37 (s, 1H), 8.22 (d, J=8.0 Hz, 1H), 8.10-8.14 (m, 3H), 7.91-7.92 (m, 2H), 7.76 (d, J=8.0 Hz, 1H), 7.61-7.66 (m, 1H), 7.35-7.47 (m, 6H), 6.83 (d, J=4.0 Hz, 1H). MS (APCI) m/z: 531 (M+H)$^+$.

Example 80

Preparation of 3-(4-(dimethylamino)phenyl)-2-(1H-indol-5-yl)quinazolin-4(3H)-one

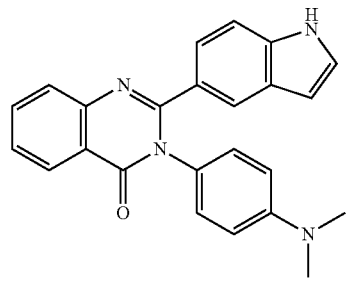 [SMILES: CN(C)c1ccc(-n2c(-c3ccc4[nH]ccc4c3)nc3ccccc3c2=O)cc1]

3-methyl-4-nitrobenzaldehyde (0.85 g, 5.20 mmol) and anhydrous CuCl$_2$ (2.1 g, 15.5 mmol) were added to a solution of 2-amino-N-(4-bromophenyl)benzamide (1.5 g, 5.20 mmol) in anhydrous EtOH (60 mL). After heating at reflux temperature for 3.5 hours, the mixture was concentrated in vacuo. The residue was dissolved in EtOAc, washed with H$_2$O, then brine, dried (Na$_2$SO$_4$), filtered, and concentrated in vacuo. Purification by flash chromatography on silica gel, eluting with 15% to 60% EtOAc in heptane, afforded 3-(4-bromophenyl)-2-(3-methyl-4-nitrophenyl)quinazolin-4 (3H)-one (1.4 g, 62%).

tert-Butoxybis(dimethylamino)methane (2.0 mL, 9.60 mmol) was added to a solution of 3-(4-bromophenyl)-2-(3-methyl-4-nitrophenyl)quinazolin-4(3H)-one (1.4 g, 3.20 mmol) in DMF (30 mL). Stirring at 60° C. for 2 hours and concentrating in vacuo afforded (E)-3-(4-bromophenyl)-2-(3-(2-(dimethylamino)vinyl)-4-nitrophenyl)quinazolin-4 (3H)-one (1.5 g, quantitative).

Zn dust (2.0 g, 30.0 mmol) was added to a solution of (E)-3-(4-bromophenyl)-2-(3-(2-(dimethylamino)vinyl)-4-nitrophenyl)quinazolin-4(3H)-one (1.5 g, 3.0 mmol) in AcOH (25 mL). The mixture was stirred at room temperature overnight, then heated to reflux temperature for 1 hour. After cooling to 0° C., the reaction mixture was basified with 1 N NaOH and extracted with EtOAc. The organics were washed with brine, dried (Na$_2$SO$_4$), filtered, and concentrated in vacuo. Purification by flash chromatography on silica gel, eluting with 0% to 40% EtOAc in CH$_2$Cl$_2$, afforded 3-(4-bromophenyl)-2-(1H-indol-5-yl)quinazolin-4(3H)-one (0.225 g, 18%).

Boc$_2$O (0.142 g, 0.65 mmol) and DMAP (0.6 mg, 0.005 mmol) were added to a solution of 3-(4-bromophenyl)-2-(1H-indol-5-yl)quinazolin-4(3H)-one (0.225 g, 0.54 mmol) in THF (15 mL). After stirring at room temperature for 4 hours, the mixture was concentrated in vacuo. Purification by flash chromatography on silica gel, eluting with 10% to 60% EtOAc in hexanes, afforded tert-butyl 5-(3-(4-bromophenyl)-4-oxo-3,4-dihydroquinazolin-2-yl)-1H-indole-1-carboxylate (0.225 g, 81%).

Dimethylamine (0.3 mL, 0.58 mmol) was added to a solution of tert-butyl 5-(3-(4-bromophenyl)-4-oxo-3,4-dihydroquinazolin-2-yl)-1H-indole-1-carboxylate (0.200 g, 0.38 mmol), NatOBu (0.112 g, 1.20 mmol), Pd(OAc)$_2$ (0.013 g, 0.06 mmol) and (t-Bu)$_3$PHBF$_4$ (0.034 g, 0.12 mmol) were added to toluene (5 mL). The mixture was microwaved at 300 W (max. power) and 90° C. for 30 min, before the mixture was concentrated in vacuo. Purification by flash chromatography on silica gel, eluting with 20% to 60% EtOAc in hexanes, afforded the title compound as a brown-yellow solid (0.048 g, 33%). $^1$H-NMR (300 MHz, DMSO-d$_6$): δ11.14 (s, 1H), 8.16 (d, J=7.7 Hz, 1H), 7.83-7.88 (m, 1H), 7.67-7.73 (m, 2H), 7.52-7.57 (m, 1H), 7.33 (s, 1H), 7.18 (d, J=8.7 Hz, 1H), 7.03-7.08 (m, 3H), 6.54 (d, J=8.8 Hz, 2H), 6.39 (s, 1H), 2.83 (s, 6H). MS (APCI) m/z: 381 (M+H)$^+$.

Example 81

Preparation of 3-(4-chlorophenyl)-2-(1-(phenylsulfonyl)-1H-pyrrolo[2,3-b]pyridin-5-yl)quinazolin-4(3H)-one

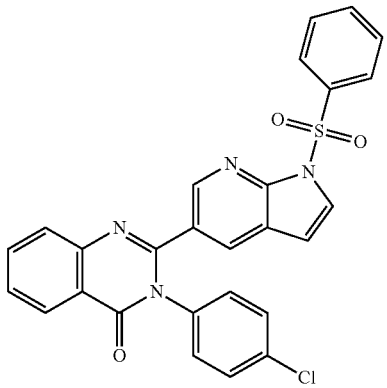 [SMILES: O=c1c2ccccc2nc(-c2cnc3c(ccn3S(=O)(=O)c3ccccc3)c2)n1-c1ccc(Cl)cc1]

Following the method described in Example 38, the title compound was made from 1-(phenylsulfonyl)-1H-pyrrolo[2,3-b]pyridine-5-carbaldehyde and isolated as a white solid. ¹H-NMR (300 MHz, DMSO-d₆): δ8.36 (d, J=2.0 Hz, 1H), 8.20-8.23 (m, 2H), 8.09 (d, J=2.0 Hz, 1H), 8.00-8.03 (m, 1H), 7.90-7.95 (m, 2H), 7.71-7.77 (m, 2H), 7.58-7.66 (m, 3H), 7.35-7.44 (m, 4H), 6.83 (d, J=4.0 Hz, 1H). MS (APCI) m/z: 513 (M+H)⁺.

Example 82

Preparation of 3-(4-sec-butylphenyl)-2-(2-(hydroxymethyl)-1H-indol-5-yl)quinazolin-4(3H)-one

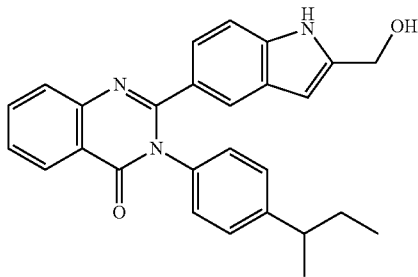 [SMILES: CCC(C)c1ccc(-n2c(-c3ccc4[nH]c(CO)cc4c3)nc3ccccc3c2=O)cc1]

Trifluoroacetic anhydride (0.19 mL, 1.30 mmol) and TEA (0.37 mL, 2.60 mmol) were added to a solution of 4-amino-3-iodobenzaldehyde (0.330 g, 1.30 mmol) in CH₂Cl₂ (15 mL). After stirring at room temperature for 1 hour, the reaction mixture was concentrated in vacuo. Purification by flash chromatography on silica gel, eluting with 5% to 50% EtOAc in heptane, afforded 2-amino-N-(4-sec-butylphenyl)benzamide (0.350 g, 79%).

2-amino-N-(4-sec-butylphenyl)benzamide (0.275 g, 1.00 mmol) and anhydrous CuCl₂ (0.275 g, 2.00 mmol) were added to a solution of 2,2,2-trifluoro-N-(4-formyl-2-iodophenyl)acetamide in anhydrous EtOH (15 mL) and heated to reflux temperature for 3 hours. After concentrating in vacuo, the residue was dissolved in EtOAc, washed with H₂O, then brine, dried (Na₂SO₄), filtered, and concentrated in vacuo. Purification by flash chromatography on silica gel, eluting with 10% to 60% EtOAc in heptane, afforded N-(4-(3-(4-sec-butylphenyl)-4-oxo-3,4-dihydroquinazolin-2-yl)-2-iodophenyl)-2,2,2-trifluoroacetamide (0.390 g, 66%).

Propargyl alcohol (0.045 mL, 0.76 mmol) and PdCl₂(PPh₃)₂ (0.007 g, 0.01 mmol) were added to a solution of N-(4-(3-(4-sec-butylphenyl)-4-oxo-3,4-dihydroquinazolin-2-yl)-2-iodophenyl)-2,2,2-trifluoroacetamide (0.300 g, 0.51 mmol) in TEA (10 mL) and DMF (3 mL). After heating to 60° C. for 5 hours, the reaction mixture was concentrated in vacuo. The residue was dissolved in EtOAc, washed with saturated NaHCO₃, then brine, dried (Na₂SO₄), filtered, and concentrated in vacuo. Purification by flash chromatography on silica gel, eluting with 20% to 80% EtOAc in heptane, plus further purification by flash chromatography on silica gel, eluting with 10% to 50% EtOAc in CH₂Cl₂, afforded the title compound as a white solid (0.065 g, 29%). ¹H-NMR (300 MHz, DMSO-d₆): δ11.09 (s, 1H), 8.18 (d, J=7.1 Hz, 1H), 7.87-7.90 (m, 1H), 7.75 (d, J=8.0 Hz, 1H), 7.47-7.64 (m, 2H), 6.93-7.25 (m, 6H), 6.19 (s, 1H), 5.23 (t, J=5.6 Hz, 1H), 4.54 (d, J=5.5 Hz, 2H), 2.53-2.61 (m, 1H), 1.30-1.62 (m, 2H), 1.12 (d, J=6.9 Hz, 3H), 0.63 (t, J=7.2 Hz, 3H). MS (APCI) m/z: 424 (M+H)⁺.

Example 83

Preparation of 3-(4-chlorophenyl)-2-(1-methyl-1H-indol-5-yl)quinazolin-4(3H)-one

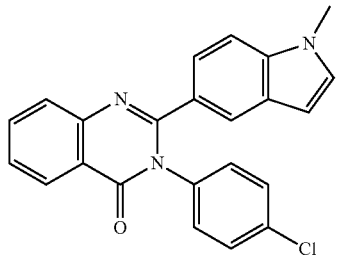 [SMILES: Cn1ccc2cc(-c3nc4ccccc4c(=O)n3-c3ccc(Cl)cc3)ccc21]

NaH (60% in oil) (0.006 g, 0.14 mmol) was added to a 0° C. solution of 3-(4-chlorophenyl)-2-(1H-indol-5-yl)quinazolin-4(3H)-one (0.14 mmol) in THF (5 mL). After stirring for 15 min, MeI (0.01 mL, 0.16 mmol) was added, and the reaction was warmed to room temperature for 1 hour. After quenching with H₂O, diluting with EtOAc, washing with brine, drying with Na₂SO₄, and filtering, the mixture was concentrated in vacuo. Purification by flash chromatography on silica gel, eluting with 10% to 70% EtOAc in heptane, afforded the title compound as a white solid (65%). ¹H-NMR (300 MHz, DMSO-d₆): δ8.18 (d, J=6.8 Hz, 1H), 7.87-7.90 (m, 1H), 7.75 (d, J=7.8 Hz, 1H), 7.66 (s, 1H), 7.57-7.59 (m, 1H), 7.21-7.47 (m, 6H), 7.12 (d, J=7.0 Hz, 1H), 6.4 (d, J=2.9 Hz, 1H), 3.74 (s, 3H). MS (APCI) m/z: 386 (M+H)⁺.

Example 84

Preparation of 3-(4-cyclopentylphenyl)-2-(1H-indol-5-yl)quinazolin-4(3H)-one

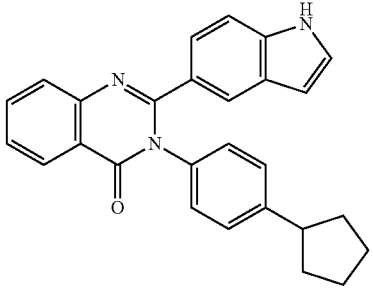 [SMILES: O=c1c2ccccc2nc(-c2ccc3[nH]ccc3c2)n1-c1ccc(C2CCCC2)cc1]

Following the method described for Example 73, 3-(4-cyclopentylphenyl)-2-(3-methyl-4-nitrophenyl)quinazolin-4(3H)-one was made from 2-amino-N-(4-cyclopentylphenyl)benzamide in 40% yield.

Following the method described for Example 73, (E)-3-(4-cyclopentylphenyl)-2-(3-(2-(dimethylamino)vinyl)-4-nitrophenyl)-quinazolin-4(3H)-one was made from 3-(4-cyclopentylphenyl)-2-(3-methyl-4-nitrophenyl)quinazolin-4(3H)-one in quantitative yield.

Following the method described for Example 73 above, the title compound was made from (E)-3-(4-cyclopentylphenyl)-2-(3-(2-(dimethylamino)vinyl)-4-nitrophenyl)-quinazolin-4(3H)-one in 28% yield. $^1$H-NMR (300 MHz, DMSO-$d_6$): δ11.15 (s, 1H), 8.18 (d, J=7.7 Hz, 1H), 7.83-7.97 (m, 1H), 7.74 (d, J=7.9 Hz, 1H), 7.63 (s, 1H), 7.54-7.59 (m, 1H), 7.27-7.40 (m, 1H), 7.12-7.27 (m, 5H), 7.05 (d, J=9.3 Hz, 1H), 6.36 (s, 1H), 2.79-3.00 (m, 1H), 1.84-2.04 (m, 2H), 1.53-1.79 (m, 4H), 1.35-1.53 (m, 2H). MS (APCI) m/z: 406 (M+H)$^+$.

Example 85

Preparation of 3-(4-chlorophenyl)-2-(1H-indol-6-yl)quinazolin-4(3H)-one

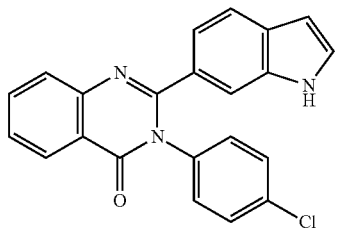 [SMILES: O=c1c2ccccc2nc(-c2ccc3cc[nH]c3c2)n1-c1ccc(Cl)cc1]

4-methyl-3-nitrobenzaldehyde (0.270 g, 1.60 mmol) and anhydrous CuCl$_2$ (0.435 g, 3.20 mmol) were added to a solution of 2-amino-N-(4-chlorophenyl)benzamide (0.400 g, 1.60 mmol) in anhydrous EtOH (10 mL). After heating at reflux temperature for 3 hours, the reaction mixture was concentrated in vacuo. The residue was dissolved in EtOAc, washed with H$_2$O, then brine, dried (Na$_2$SO$_4$), filtered, and concentrated in vacuo. Purification by flash chromatography on silica gel, eluting with 5% to 60% EtOAc in heptane, afforded 3-(4-chlorophenyl)-2-(4-methyl-3-nitrophenyl)quinazolin-4(3H)-one (0.400 g, 63%).

tert-butoxybis(dimethylamino)methane (0.50 mL, 2.30 mmol) was added to a solution of 3-(4-chlorophenyl)-2-(4-methyl-3-nitrophenyl)quinazolin-4(3H)-one (0.300 g, 0.76 mmol) in DMF (20 mL). Stirring at 50° C. for 3 hours and concentrating in vacuo afforded (E)-3-(4-chlorophenyl)-2-(4-(2-(dimethylamino)vinyl)-3-nitrophenyl)quinazolin-4(3H)-one (0.340 g, 100%).

A solution of (E)-3-(4-chlorophenyl)-2-(4-(2-(dimethylamino)vinyl)-3-nitrophenyl)quinazolin-4(3H)-one (0.340 g, 0.76 mmol) in a 3:1 mixture of EtOH/DMF (50 mL) was flushed with N$_2$. Pd/C (0.034 g, 10 wt %) was added the reaction was flushed with H$_2$ for 1.5 hours. After filtering through diatomaceous earth, the filtrate was concentrated. Purification by flash chromatography on silica gel, eluting with 5% to 70% EtOAc in heptane, afforded the title compound as a white solid (0.105 g, 37%). $^1$H-NMR (300 MHz, DMSO-$d_6$, mixture of rotamers): δ11.34 (s, 0.5H), 11.25 (s, 0.5H), 8.16-8.29 (m, 1H), 7.86-8.00 (m, 1H), 7.71-7.82 (m, 1H), 7.49-7.67 (m, 3H), 7.29-7.48 (m, 5H), 6.87-7.05 (m, 1H), 6.37-6.42 (m, 0.5H), 6.25-6.26 (m, 0.5H). MS (APCI) m/z: 372 (M+H)$^+$.

Example 86

Preparation of 3-(4-chlorophenyl)-2-(1H-indol-7-yl)quinazolin-4(3H)-one

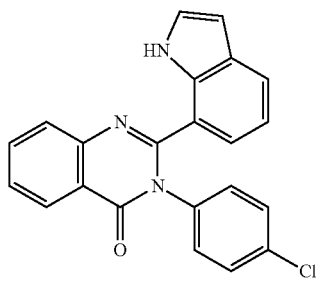 [SMILES: O=c1c2ccccc2nc(-c2cccc3cc[nH]c23)n1-c1ccc(Cl)cc1]

Following the method described for Example 85, 3-(4-chlorophenyl)-2-(3-methyl-2-nitrophenyl)quinazolin-4(3H)-one was made from 3-methyl-2-nitrobenzaldehyde in 46% yield. Following the method described for Example 85, (E)-3-(4-chlorophenyl)-2-(3-(2-(dimethylamino)vinyl)-2-nitrophenyl)quinazolin-4(3H)-one was made from 3-(4-chlorophenyl)-2-(3-methyl-2-nitrophenyl)quinazolin-4(3H)-one in quantitative yield.

Following the method described for Example 85, the title compound was made from (E)-3-(4-chlorophenyl)-2-(3-(2-(dimethylamino)vinyl)-2-nitrophenyl)quinazolin-4(3H)-one in 15% yield. $^1$H-NMR (300 MHz, DMSO-$d_6$): δ11.08 (s, 1H), 8.23-8.27 (m, 1H), 7.90-7.94 (m, 1H), 7.76 (d, J=7.7 Hz, 1H), 7.61-7.64 (m, 1H), 7.45 (d, J=7.8 Hz, 1H), 7.28-7.40 (m, 3H), 7.16-7.26 (m, 2H), 7.08 (d, J=6.5 Hz, 1H), 6.87 (t, J=7.5 Hz, 1H), 6.25-6.45 (m, 1H). MS (APCI) m/z: 372 (M+H)$^+$.

Example 87

Preparation of 3-(4-sec-butylphenyl)-2-(1H-indol-6-yl)quinazolin-4(3H)-one

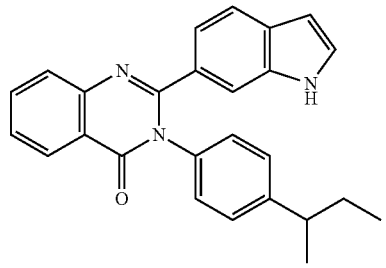 [SMILES: CCC(C)c1ccc(-n2c(-c3ccc4cc[nH]c4c3)nc3ccccc3c2=O)cc1]

4-methyl-3-nitrobenzaldehyde (0.246 g, 1.50 mmol) and anhydrous CuCl$_2$ (0.400 g, 3.00 mmol) were added to a solution of 2-amino-N-(4-sec-butylphenyl)benzamide (0.400 g, 1.50 mmol) in anhydrous EtOH (15 mL). After heating at reflux temperature for 2 hours, the reaction mixture was concentrated in vacuo. The residue was dissolved in EtOAc, washed with H$_2$O, then brine, dried (Na$_2$SO$_4$), filtered, and concentrated in vacuo. Purification by flash chromatography on silica gel, eluting with 5% to 60% EtOAc in heptane, afforded 3-(4-sec-butylphenyl)-2-(4-methyl-3-nitrophenyl) quinazolin-4(3H)-one (0.500 g, 81%).

tert-Butoxybis(dimethylamino)methane (0.75 mL, 3.60 mmol) was added to a solution of 3-(4-sec-butylphenyl)-2-(4-methyl-3-nitrophenyl)quinazolin-4(3H)-one (0.500 g, 1.20 mmol) in DMF (30 mL). Stirring at 40° C. for 3 hours and concentrating in vacuo afforded (E)-3-(4-sec-butylphenyl)-2-(4-(2-(dimethylamino)vinyl)-3-nitrophenyl)quinazolin-4(3H)-one (0.565 g, quantitative).

A solution of (E)-3-(4-sec-butylphenyl)-2-(4-(2-(dimethylamino)vinyl)-3-nitrophenyl)quinazolin-4(3H)-one (0.565 g, 1.20 mmol) in a 3:1 mixture of EtOH/DMF (25 mL) was flushed with $N_2$. Pd/C (0.060 g, 10 wt %) was added and flushed with $H_2$ for 2.5 hours. After filtering through diatomaceous earth, the filtrate was concentrated. Purification was effected by flash chromatography on silica gel, eluting with 5% to 75% EtOAc in heptane, Further purification was effected by reverse-phase chromatography, eluting with 10% to 90% $CH_3CN$ in $H_2O$ with 0.1% TFA. The desired fractions were collected, basified, and extracted with $CH_2Cl_2$, to afford the title compound as a white solid (0.040 g, 8%). $^1$H-NMR (300 MHz, DMSO-$d_6$): δ11.27 (s, 1H), 8.18 (d, J=8.0 Hz, 1H), 7.87-7.90 (m 1H), 7.75 (d, J=7.8 Hz, 1H), 7.56-7.59 (m, 1H), 7.50 (s, 1H), 7.37 (d, J=2.6 Hz, 1H), 7.27 (d, J=8.3 Hz, 1H), 7.19-7.22 (m, 2H), 7.08-7.10 (m, 2H), 6.89-6.92 (m, 1H), 6.34 (s, 1H), 2.51-2.61 (m, 1H), 1.33-1.20 (m, 2H), 1.11 (d, J=6.9 Hz, 3H), 0.59 (t, J=7.3 Hz, 3H). MS (APCI) m/z: 394 (M+H)$^+$.

Example 88

Preparation of 3-(4-sec-butylphenyl)-2-(1H-indol-7-yl)quinazolin-4(3H)-one

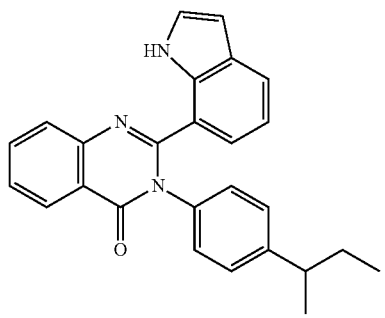 [SMILES: CCC(C)c1ccc(-n2c(-c3cccc4cc[nH]c34)nc3ccccc3c2=O)cc1]

Following the method described for Example 87, 3-(4-sec-butylphenyl)-2-(3-methyl-2-nitrophenyl)quinazolin-4(3H)-one was made from 3-methyl-2-nitrobenzaldehyde in 53% yield.

Following the method described for Example 87, (E)-3-(4-sec-butylphenyl)-2-(3-(2-(dimethylamino)vinyl)-2-nitrophenyl)quinazolin-4(3H)-one was made from 3-(4-sec-butylphenyl)-2-(3-methyl-2-nitrophenyl)quinazolin-4(3H)-one in qunatitative yield.

Following the method described for Example 87, the title compound was made from (E)-3-(4-sec-butylphenyl)-2-(3-(2-(dimethylamino)vinyl)-2-nitrophenyl)quinazolin-4(3H)-one in 25% yield. $^1$H-NMR (300 MHz, DMSO-$d_6$): δ11.14 (br s, 1H), 8.22-8.26 (m, 1H), 7.90-7.93 (m, 1H), 7.76 (d, J=7.8 Hz, 1H), 7.61-7.64 (m, 1H), 7.40 (d, J=7.8 Hz, 1H), 7.28-7.32 (m, 1H), 7.11-7.24 (m, 2H), 6.90-7.03 (m, 3H), 6.77-6.79 (m, 1H), 6.29-6.42 (m, 1H), 2.32-2.46 (m, 1H), 1.18-1.58 (m, 2H), 1.05 (d, J=6.9 Hz, 3H), 0.52 (t, J=7.4 Hz, 3H). MS (APCI) m/z: 394 (M+H)$^+$.

Example 89

Preparation of 3-(4-chlorophenyl)-2-(1H-indol-4-yl) quinazolin-4(3H)-one

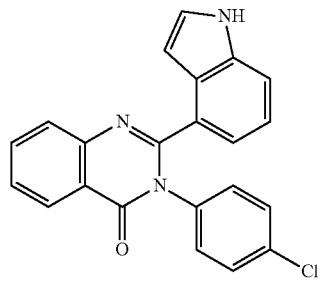 [SMILES: O=c1c2ccccc2nc(-c2cccc3[nH]ccc23)n1-c1ccc(Cl)cc1]

Following the method described for Example 85, 3-(4-chlorophenyl)-2-(2-methyl-3-nitrophenyl)quinazolin-4 (3H)-one was made from 2-methyl-3-nitrobenzaldehyde in 48% yield.

Following the method described for Example 85, (E)-3-(4-chlorophenyl)-2-(2-(2-(dimethylamino)vinyl)-3-nitrophenyl)quinazolin-4(3H)-one was made from 3-(4-chlorophenyl)-2-(2-methyl-3-nitrophenyl)quinazolin-4(3H)-one in quantitative yield.

Following the method described for Example 85, the title compound was made from (E)-3-(4-chlorophenyl)-2-(2-(2-(dimethylamino)vinyl)-3-nitrophenyl)quinazolin-4(3H)-one in 19% yield. $^1$H-NMR (300 MHz, DMSO-$d_6$): δ11.29 (s, 1H), 8.17-8.22 (m, 1H), 7.89-7.92 (m, 1H), 7.74 (d, J=7.6 Hz, 1H), 7.59-7.63 (m, 1H), 7.42 (d, J=3.3 Hz, 1H), 7.28-7.40 (m, 3H), 7.15-7.25 (m, 2H), 6.98-7.10 (m, 2H), 6.40 (d, J=2.5 Hz, 1H). MS (APCI) m/z: 372 (M+H)$^+$.

Example 90

Preparation of 3-(4-sec-butylphenyl)-2-(1H-indol-4-yl)quinazolin-4(3H)-one

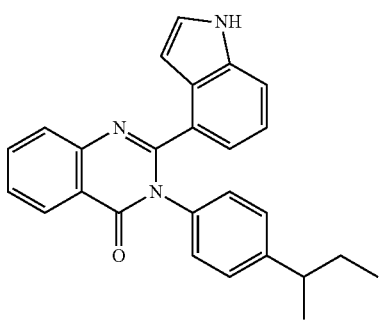 [SMILES: CCC(C)c1ccc(-n2c(-c3cccc4[nH]ccc34)nc3ccccc3c2=O)cc1]

Following the method described for Example 87, 3-(4-sec-butylphenyl)-2-(2-methyl-3-nitrophenyl)quinazolin-4(3H)-one was made from 2-methyl-3-nitrobenzaldehyde in 59% yield.

Following the method described for Example 87, (E)-3-(4-sec-butylphenyl)-2-(2-(2-(dimethylamino)vinyl)-3-nitrophenyl)quinazolin-4(3H)-one was made from 3-(4-sec-butylphenyl)-2-(2-methyl-3-nitrophenyl)quinazolin-4(3H)-one in quantitative yield.

Following the method described for Example 87, the title compound was made from (E)-3-(4-sec-butylphenyl)-2-(2-(2-(dimethylamino)vinyl)-3-nitrophenyl)quinazolin-4(3H)-one in 43% yield. $^1$H-NMR (300 MHz, DMSO-$d_6$): δ11.09 (s, 1H), 8.17-8.22 (m, 1H), 7.89-7.92 (m, 1H), 7.72 (d, J=7.8 Hz, 1H), 7.59-7.61 (m, 1H), 7.20-7.35 (m, 2H), 7.12 (d, J=8.2 Hz, 2H), 6.95 (d, J=7.6 Hz, 2H), 6.81-6.90 (m, 2H), 6.49 (d, J=2 Hz, 1H), 2.39-2.42 (m, 1H), 1.28-1.54 (m, 2H), 1.06 (d, J=6.9 Hz, 3H), 0.54 (t, J=7.4 Hz, 3H). MS (APCI) m/z: 394 (M+H)$^+$.

Example 91

Quantification of ApoA-I mRNA

In this example, ApoA-I mRNA in tissue culture cells was quantitated to measure the transcriptional up-regulation of ApoA-I when treated with a compound of the invention.

HepG2 cells (approximately 2×10$^5$ per well) were placed in a 24-well plate in approximately 400 µL MEM, supplemented with 0.5% (v/v) FBS, 24 h before addition of the compound of interest. At time of harvesting, the spent media was removed from the HepG2 cells and immediately placed on ice (for immediate use) or at −80° C. (for future use) in ApoA-I and albumin ELISAs. The cells remaining in the plate wells were rinsed in 200 µL PBS. PBS was carefully removed to avoid removing any loosely attached cells.

Once the PBS was removed, 85 µL cell lysis solution was added the cells in each well and incubated for 5-10 minutes at room temperature, to allow for complete cell lysis and detachment. mRNA was then prepared using the "mRNA Catcher PLUS plate" from Invitrogen, according to the protocol supplied. After the last wash, as much wash buffer as possible was aspirated without allowing the wells to dry. Elution Buffer (E3, 80 µL) was then added to each well. mRNA was then eluted by incubating the mRNA Catcher PLUS plate with Elution Buffer for 5 minutes at 68° C. and then immediately placing the plate on ice.

The eluted mRNA isolated was then used in a one-step real-time room temperature-PCR reaction, using components of the Ultra Sense Kit together with Applied Biosystems primer-probe mixes. Real-time PCR data was analyzed, using the Ct values, to determine the fold induction of each unknown sample, relative to the control (that is, relative to the control for each independent DMSO concentration).

An active compound was defined as one that caused a ≥20% increase in ApoA-I mRNA at a concentration less than or equal to 100 µM.

| Example # | Compound Name | Effect on ApoA-I mRNA levels |
|---|---|---|
| 1 and 2 | 3-(4-sec-butylphenyl)-2-(4-(2-hydroxyethoxy)-3,5-dimethylphenyl)quinazolin-4(3H)-one | Active |
| 3 | 3-(4-bromophenyl)-2-(4-(2-hydroxyethoxy)-3,5-dimethylphenyl)quinazolin-4(3H)-one | Active |
| 4 | 3-(4-sec-butylphenyl)-7-fluoro-2-(4-(2-hydroxyethoxy)-3,5-dimethylphenyl)quinazolin-4(3H)-one | Active |
| 5 | 3-(4-sec-butylphenl)-2-(4-(2-hydroxyethoxy)-3,5-dinnethylphenyl)pyrido[4,3-d]pyrimidin-4(3H)-one | Active |
| 6 | 3-(4-sec-butylphenyl)-2-(4-(2-hydroxyethoxy)phenyl)quinazolin-4(3H)-one | Active |
| 7 | 3-(4-fluorophenyl)-2-(4-(2-hydroxyethoxy)-3,5-dimethylphenyl)quinazolin-4(3H)-one | Active |
| 8 | 2-(4-(2-hydroxyethoxy)-3,5-dimethylphenyl)-3-(4-iodophenyl)quinazolin-4(3H)-one | Active |
| 9 | 3-(4-sec-butylphenyl)-6-fluoro-2-(4-(2-hydroxyethoxy)-3,5-dimethylphenyl)quinazolin-4(3H)-one | Active |
| 10 | 3-(4-chlorophenyl)-2-(4-(2-hydroxyethoxy)-3,5-dimethylphenyl)quinazolin-4(3H)-one | Active |
| 11 | 2-(4-(2-hydroxyethoxy)-3,5-dimethylphenyl)-3-(4-(trifluoromethyl)phenyl)quinazolin-4(3H)-one | Active |
| 12 | 3-(4-sec-butylphenyl)-2-(4-(2-hydroxyethoxy)-3,5-dimethylphenyl)-7-(methylsulfonyl)quinazolin-4(3H)-one | Active |
| 13 | 3-(4-sec-butylphenyl)-2-(4-(2-hydroxyethoxy)-3,5-dimethylphenyl)-6-methoxyquinazolin-4(3H)-one | Active |
| 14 | 3-(4-sec-butylphenyl)-2-(4-(2-hydroxyethoxy)-3,5-dimethylphenyl)-8-methoxyquinazolin-4(3H)-one | Active |
| 15 | 3-(4-sec-butylphenyl)-2-(4-(2-hydroxyethoxy)-3,5-dimethylphenyl)-6-(methylsulfonyl)quinazolin-4(3H)-one | Active |
| 16 | 3-(4-bromophenyl)-2-(4-(2-hydroxyethoxy)-3,5-dimethylphenyl)-6-methoxyquinazolin-4(3H)-one | Active |
| 17 | 3-(4-bromophenyl)-2-(4-(2-hydroxyethoxy)-3,5-dimethylphenyl)-8-methoxyquinazolin-4(3H)-one | Active |
| 18 | 2-(4-(2-hydroxyethoxy)-3,5-dimethylphenyl)-3-(4-isopropylphenyl)quinazolin-4(3H)-one | Active |
| 19 | 3-(4-bromophenyl)-2-(4-(2-hydroxyethoxy)-3-methylphenyl)quinazolin-4(3H)-one | Active |
| 20 | 3-(4-bromophenyl)-8-chloro-2-(4-(2-hydroxyethoxy)-3,5-dimethylphenyl)quinazolin-4(3H)-one | Active |
| 21 | 2-(4-(2-hydroxyethoxy)-3,5-dimethylphenyl)-3-(4-morpholinophenyl)quinazolin-4(3H)-one | Active |
| 22 | 3-(4-tert-butylphenyl)-2-(4-(2-hydroxyethoxy)-3,5-dimethylphenyl)quinazolin-4(3H)-one | Active |
| 23 | N-(4-(2-(4-(2-hydroxyethoxy)-3,5-dimethylphenyl)-4-oxoquinazolin-3(4H)-yl)phenyl)acetamide | Active |

| Example # | Compound Name | Effect on ApoA-I mRNA levels |
|---|---|---|
| 24 | N-(4-(2-(4-(2-hydroxyethoxy)-3,5-dimethylphenyl)-4-oxoquinazolin-3(4H)-yl)phenyl)isobutyramide | Active |
| 25 | methyl 4-(2-(4-(2-hydroxyethoxy)-3,5-dimethylphenyl)-4-oxoquinazolin-3(4H)-yl)benzoate | Active |
| 26 | 3-(4-cyclohexylphenyl)-2-(4-(2-hydroxyethoxy)-3,5-dimethylphenyl)quinazolin-4(3H)-one | Active |
| 27 | N-(4-(2-(4-(2-hydroxyethoxy)-3,5-dimethylphenyl)-4-oxoquinazolin-3(4H)-yl)phenyl)formamide | Active |
| 28 | 3-(4-aminophenyl)-2-(4-(2-hydroxyethoxy)-3,5-dimethylphenyl)quinazolin-4(3H)-one | Active |
| 29 | N-(4-(2-(4-(2-hydroxyethoxy)-3,5-dimethylphenyl)-4-oxoquinazolin-3(4H)-yl)phenyl)methanesulfonamide | Active |
| 30 | N-(4-(2-(4-(2-hydroxyethoxy)-3,5-dimethylphenyl)-4-oxoquinazolin-3(4H)-yl)phenyl)benzenesulfonamide | |
| 31 | N-(4-(2-(4-(2-hydroxyethoxy)-3,5-dimethylphenyl)-4-oxoquinazolin-3(4H)-yl)phenyl)propane-2-sulfonamide | Active |
| 32 | 3-(4-(dimethylamino)phenyl)-2-(4-(2-hydroxyethoxy)-3,5-dimethylphenyl)quinazolin-4(3H)-one | Active |
| 33 | 3-(4-sec-butylphenyl)-2-(4-(2-hydroxyethoxy)-3-methylphenyl)quinazolin-4(3H)-one | Active |
| 34 | 3-(4-chlorophenyl)-2-(4-(2-hydroxyethoxy)-3-methylphenyl)quinazolin-4(3H)-one | Active |
| 35 | 3-(4-sec-butylphenyl)-2-(pyridin-3-yl)quinazolin-4(3H)-one | Active |
| 36 | 3-(4-chlorophenyl)-2-(quinolin-3-yl)quinazolin-4(3H)-one | Active |
| 37 | 3-(4-sec-butylphenyl)-2-(5-fluoropyridin-3-yl)quinazolin-4(3H)-one | Active |
| 38 | 3-(4-chlorophenyl)-2-(6-chloropyridin-3-yl)quinazolin-4(3H)-one | Active |
| 39 | 3-(4-sec-butylphenyl)-2-(6-chloropyridin-3-yl)quinazolin-4(3H)-one | Active |
| 40 | 3-(4-sec-butylphenyl)-2-(6-methoxypyridin-3-yl)quinazolin-4(3H)-one | Active |
| 41 | 2-(6-bromopyridin-3-yl)-3-(4-chlorophenyl)quinazolin-4(3H)-one | Active |
| 42 | 2-(6-bromopyridin-3-yl)-3-(4-sec-butylphenyl)quinazolin-4(3H)-one | Active |
| 43 | 3-(4-chlorophenyl)-2-(6-(diethylamino)pyridin-3-yl)quinazolin-4(3H)-one | Active |
| 44 | 3-(4-sec-butylphenyl)-2-(6-(diethylamino)pyridin-3-yl)quinazolin-4(3H)-one | Active |
| 45 | 3-(4-sec-butylphenyl)-2-(pyrimidin-5-yl)quinazolin-4(3H)-one | Active |
| 46 | 3-(4-sec-butylphenyl)-2-(6-methylpyridin-3-yl)quinazolin-4(3H)-one | Active |
| 47 | 3-(4-chlorophenyl)-2-(6-methylpyridin-3-yl)quinazolin-4(3H)-one | Active |
| 48 | 3-(4-chlorophenyl)-2-(6-(piperidin-1-yl)pyridin-3-yl)quinazolin-4(3H)-one | Active |
| 49 | 3-(4-sec-butylphenyl)-2-(6-(piperidin-1-yl)pyridin-3-yl)quinazolin-4(3H)-one | Active |
| 50 | 3-(4-chlorophenyl)-2-(6-phenoxypyridin-3-yl)quinazolin-4(3H)-one | Active |
| 51 | 3-(4-sec-butylphenyl)-2-(6-fluoropyridin-3-yl)quinazolin-4(3H)-one | Active |
| 52 | 3-(4-sec-butylphenyl)-2-(6-phenoxypyridin-3-yl)quinazolin-4(3H)-one | Active |
| 53 | 3-(4-chlorophenyl)-2-(6-(trifluoromethyl)pyridin-3-yl)quinazolin-4(3H)-one | Active |
| 54 | 3-(4-sec-butylphenyl)-2-(6-(trifluoromethyl)pyridin-3-yl)quinazolin-4(3H)-one | Active |
| 55 | 3-(4-sec-butylphenyl)-2-(6-phenylpyridin-3-yl)quinazolin-4(3H)-one | Active |
| 56 | 3-(4-sec-butylphenyl)-2-(5-phenylpyridin-3-yl)quinazolin-4(3H)-one | Active |
| 57 | 2-(5-bromopyridin-3-yl)-3-(4-sec-butylphenyl)quinazolin-4(3H)-one | Active |
| 58 | 2-(5-bromopyridin-3-yl)-3-(4-chlorophenyl)quinazolin-4(3H)-one | Active |
| 59 | 3-(4-sec-butylphenyl)-2-(5-(diethylamino)pyridin-3-yl)quinazolin-4(3H)-one | Active |
| 60 | 3-(4-chlorophenyl)-2-(5-phenylpyridin-3-yl)quinazolin-4(3H)-one | Active |
| 61 | 3-(4-chlorophenyl)-2-(5-(diethylamino)pyridin-3-yl)quinazolin-4(3H)-one | Active |
| 62 | 3-(4-cyclopentylphenyl)-2-(6-methylpyridin-3-yl)quinazolin-4(3H)-one | Active |

| Example # | Compound Name | Effect on ApoA-I mRNA levels |
|---|---|---|
| 63 | 3-(4-sec-butylphenyl)-2-(6-(hydroxymethyl)pyridin-3-yl)quinazolin-4(3H)-one | Active |
| 64 | 2-(6-methylpyridin-3-yl)-3-(4-(methylthio)phenyl)quinazolin-4(3H)-one | Active |
| 65 | 3-(4-isopropylphenyl)-2-(6-methylpyridin-3-yl)quinazolin-4(3H)-one | Active |
| 66 | N-(4-(2-(6-methylpyridin-3-yl)-4-oxoquinazolin-3(4H)-yl)phenyl)methanesulfonamide | Active |
| 67 | 3-(4-sec-butylphenyl)-2-(6-(morpholinomethyl)pyridin-3-yl)quinazolin-4(3H)-one | Active |
| 68 | 3-(4-cyclopropylphenyl)-2-(6-methylpyridin-3-yl)quinazolin-4(3H)-one | Active |
| 69 | 3-(4-(dimethylamino)phenyl)-2-(6-methylpyridin-3-yl)quinazolin-4(3H)-one | Active |
| 70 | 2-(6-chloropyridin-3-yl)-3-(4-cyclopropylphenyl)quinazolin-4(3H)-one | Active |
| 71 | 3-(4-sec-butylphenyl)-2-(6-morpholinopyridin-3-yl)quinazolin-4(3H)-one | Active |
| 72 | 3-(4-sec-butylphenyl)-2-(1H-indazol-5-yl)quinazolin-4(3H)-one | Active |
| 73 | 3-(4-chlorophenyl)-2-(1H-indol-5-yl)quinazolin-4(3H)-one | Active |
| 74 | 3-(4-sec-butylphenyl)-2-(1H-indol-5-yl)quinazolin-4(3H)-one | Active |
| 75 | 3-(4-sec-butylphenyl)-2-(2-(hydroxymethyl)-1H-benzo[d]imidazol-6-yl)quinazolin-4(3H)-one | Active |
| 76 | 2-(1H-indol-5-yl)-3-(4-(trifluoromethoxy)phenyl)quinazolin-4(3H)-one | Active |
| 77 | 2-(1H-indol-5-yl)-3-(4-isopropylphenyl)quinazolin-4(3H)-one | Active |
| 78 | 3-(4-chlorophenyl)-2-(1-(4-methoxyphenylsulfonyl)-1H-pyrrolo[2,3-b]pyridin-5-yl)quinazolin-4(3H)-one | Active |
| 79 | 3-(4-chlorophenyl)-2-(1-(4-fluorophenylsulfonyl)-1H-pyrrolo[2,3-b]pyridin-5-yl)quinazolin-4(3H)-one | Active |
| 80 | 3-(4-(dimethylamino)phenyl)-2-(1H-indol-5-yl)quinazolin-4(3H)-one | Active |
| 81 | 3-(4-chlorophenyl)-2-(1-(phenylsulfonyl)-1H-pyrrolo[2,3-b]pyridin-5-yl)quinazolin-4(3H)-one | Active |
| 82 | 3-(4-sec-butylphenyl)-2-(2-(hydroxymethyl)-1H-indol-5-yl)quinazolin-4(3H)-one | Active |
| 83 | 3-(4-chlorophenyl)-2-(1-methyl-1H-indol-5-yl)quinazolin-4(3H)-one | Active |
| 84 | 3-(4-cyclopentylphenyl)-2-(1H-indol-5-yl)quinazolin-4(3H)-one | Active |
| 85 | 3-(4-chlorophenyl)-2-(1H-indol-6-yl)quinazolin-4(3H)-one | Active |
| 86 | 3-(4-chlorophenyl)-2-(1H-indol-7-yl)quinazolin-4(3H)-one | Active |
| 87 | 3-(4-sec-butylphenyl)-2-(1H-indol-6-yl)quinazolin-4(3H)-one | Active |
| 88 | 3-(4-sec-butylphenyl)-2-(1H-indol-7-yl)quinazolin-4(3H)-one | Active |
| 89 | 3-(4-chlorophenyl)-2-(1H-indol-4-yl)quinazolin-4(3H)-one | Active |
| 90 | 3-(4-sec-butylphenyl)-2-(1H-indol-4-yl)quinazolin-4(3H)-one | Active |

These results indicate that the compounds of the invention may be useful for increasing the transcription of ApoA-I in vivo, and elevating plasma levels of ApoA-I and circulating levels of HDL-C in mammals. While some embodiments have been shown and described, various modifications and substitutions may be made thereto without departing from the spirit and scope of the invention. For example, it is not intended that the claims set forth hereinafter be construed narrower that the literal language thereof, nor is it intended that the exemplary embodiments from the specification be read into the claims. Accordingly, it is to be understood that the present invention has been described herein by way of illustration only, and that such descriptions do not constitute limitations on the scope of the claims.

All references referred to herein are incorporated by reference in their entirety.

What is claimed is:

1. A compound of Formula I:

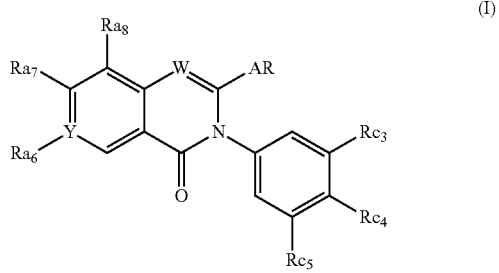

or a stereoisomer, tautomer, pharmaceutically acceptable salt, or hydrate thereof, wherein Y is carbon;
W is nitrogen;
$R_{a_6}$ is selected from fluoride, hydrogen, $C_1$-$C_3$ alkoxy, cyclopropyloxy, $SO_2R_3$, $SOR_3$, and $SR_3$, wherein if Y is nitrogen then $Ra_6$ is absent;
$R_{a_7}$ is selected from hydrogen, fluoride, $SO_2R_3$, $SOR_3$, and $SR_3$;
$R_{a_8}$ is selected from hydrogen, $C_1$-$C_3$ alkoxy, cyclopropyloxy, chloride, and bromide;
AR is

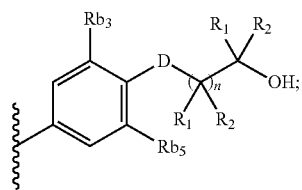

n is selected from 1, 2, or 3;
D is selected from O, NH, $NR_1$, S, or C;
$R_{b_3}$ and $R_{b_5}$ are independently selected from hydrogen and $C_1$-$C_3$ alkyl;
$R_{c_3}$ and $R_{c_5}$ are independently selected from hydrogen, $C_1$-$C_3$ alkyl, and cyclopropyl;
$R_{c_4}$ is selected from F, Cl, Br, I, $CF_3$, $C_1$-$C_6$ alkyl, $C_3$-$C_6$ cycloalkyl, $NHC(O)R_4$, $NHSO_2R_4$, $C(O)OR_4$, and

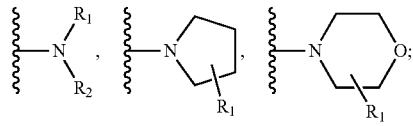

$R_1$, $R'_1$, $R_2$ and $R'_2$ are independently selected from hydrogen, fluoride, $C_1$-$C_3$ alkyl, and cyclopropyl, wherein $R_1$ and $R_2$ and/or $R'_1$ and $R'_2$ may be connected to form a 3-6 membered ring;
$R_3$ is selected from $C_1$-$C_3$ alkyl and cyclopropyl; and
$R_4$ is selected from hydrogen, $C_1$-$C_4$ alkyl, $C_3$-$C_5$ cycloalkyl, and aryl, provided that if $R_{a_7}$ or $R_{a_6}$ is fluoride, then $R_{c_4}$ is not bromide.

2. The compound according to claim 1, wherein $R_{c_4}$ is selected from F, Cl, Br, I, $CF_3$, $C_1$-$C_6$ alkyl, cyclohexyl, —$NHC(O)R_4$, —$NHSO_2R_4$, —$C(O)OR_4$, and

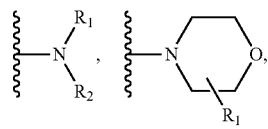

wherein
$R_4$ is selected from hydrogen, $C_1$-$C_4$ alkyl, and aryl; and
$R_1$ and $R_2$ are independently selected from hydrogen and $C_1$-$C_3$ alkyl.

3. A compound of Formula II:

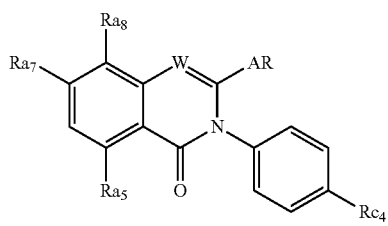

(II)

or a tautomer, stereoisomer, pharmaceutically acceptable salt or hydrate thereof wherein:
W is carbon or nitrogen;
AR is

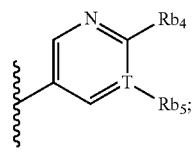

T is carbon or nitrogen;
$R_{a_6}$, $R_{a_7}$, and $R_{a_8}$ are independently selected from hydrogen and fluoride;
$R_{b_4}$ is selected from hydrogen, Cl, Br, F, $CF_3$, $C_1$-$C_4$ alkyl, $C_3$-$C_5$ cycloalkyl, $C_1$-$C_4$ alkoxy, $C_3$-$C_5$ cycloalkoxy, methoxy, -Oaryl, phenyl, $CH_2OH$, —$CH_2$morpholino, morpholino, piperidinyl, —$CH_2$piperazino, —$CH_2$(N-methylpiperazino), —$NR_1R_2$, and —$CH_2NR_1R_2$;
$R_{b_5}$ is selected from hydrogen, Cl, Br, F, aryl, and —$NR_1R_2$, wherein $R_{b_4}$ and $R_{b_5}$ may be connected to form a ring;
$R_{c_4}$ is selected from Cl, Br, $C_2$-$C_5$ alkyl, $C_3$-$C_5$ cycloalkyl, —$SR_1$, —$NHSO_2R_1$, —$NR_1R_2$; and
$R_1$ and $R_2$ are independently selected from $C_1$-$C_4$ alkyl and $C_3$-$C_6$ cycloalkyl wherein $R_1$ and $R_2$ may be connected to form a 3-6-membered ring, provided that
if $R_{b_4}$ is fluoride, phenyl, methoxy, $CH_2OH$, —$CH_2$morpholino, morpholino, —$CH_2$piperazino, or —$CH_2$(N-methylpiperazino) then $R_{c_4}$ is not chloride;
if $R_{a_7}$ or $R_{a_6}$ is fluoride, then $R_{c_4}$ is not bromide;
if $R_{b_5}$ is fluoride then $R_{c_4}$ is not chloride;
if $R_{c_4}$ is chloride or bromide, then at least one of $R_{b_2}$, $R_{b_4}$, or $R_{b_5}$ is not hydrogen;
if T is N, then $R_{c_4}$ is not halogen; and
if AR is

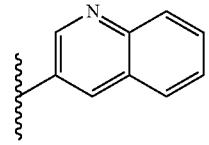 [SMILES: *c1cnc2ccccc2c1]

then $R_{c_4}$ is not sec-butyl.

4. The compound according to claim 3, wherein $R_{a_5}$, $R_{a_7}$, and $R_{a_8}$ are each hydrogen.

5. The compound according to claim 3, wherein $R_{b_4}$ and $R_{b_5}$ together to which the atoms they are bound form a phenyl ring.

6. A compound of Formula III:

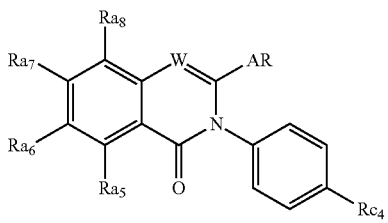

(III)

or a tautomer, stereoisomer, pharmaceutically acceptable salt, or hydrate thereof wherein:
W is nitrogen;
AR is selected from:

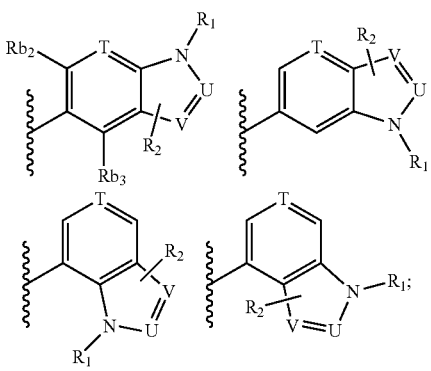

T, U, and V are independently selected from carbon and nitrogen;
$R_1$ is selected from hydrogen, $C_1$-$C_5$ alkyl, $C_3$-$C_5$ cycloalkyl, and —$SO_2R_3$;
$R_2$ is selected from hydrogen, $C_1$-$C_5$ alkyl, $C_3$-$C_5$ cycloalkyl, and $CH_2OH$;
$R_3$ is selected from hydrogen, $C_1$-$C_5$ alkyl, $C_3$-$C_5$ cycloalkyl, and optionally substituted aryl;
$R_4$ is selected from hydrogen, $C_1$-$C_5$ alkyl, and $C_3$-$C_5$ cycloalkyl;
$R_5$ is selected from hydrogen, $C_1$-$C_5$ alkyl, and $C_3$-$C_5$ cycloalkyl;
$R_{a5}$, $R_{a6}$, $R_{a7}$, and $R_{a8}$ are independently selected from hydrogen and fluoride;
$R_{b2}$ and $R_{b3}$ are independently selected from hydrogen, F, Cl, Br, $C_1$-$C_3$ alkyl, cyclopropyl, and $C_1$-$C_3$ alkoxy; and
$R_{c4}$ is selected from $C_2$-$C_6$ alkyl, $C_3$-$C_6$ cycloalkyl, F, Cl, Br, I, $OCF_3$, and —$NR_4R_5$, provided that
if $R_1$ is methyl, then $R_{c4}$ is not sec-butyl; and
if $R_2$ is $CH_2OH$, then $R_{c4}$ is not Cl.

7. The compound according to claim 6, wherein T is nitrogen and U and V are both carbon.

8. The compound according to claim 6, wherein T is carbon and U and V are both carbon.

9. The compound according to claim 6, wherein T is carbon, U is carbon, and V is nitrogen.

10. A compound selected from the group consisting of:
3-(4-sec-butylphenyl)-2-(4-(2-hydroxyethoxy)-3,5-dimethylphenyl)quinazolin-4(3H)-one;
3-(4-sec-butylphenyl)-2-(4-(2-hydroxyethoxy)phenyl)quinazolin-4(3H)-one;
3-(4-fluorophenyl)-2-(4-(2-hydroxyethoxy)-3,5-dimethylphenyl)quinazolin-4(3H)-one;
2-(4-(2-hydroxyethoxy)-3,5-dimethylphenyl)-3-(4-iodophenyl)quinazolin-4(3H)-one;
3-(4-bromophenyl)-2-(4-(2-hydroxyethoxy)-3,5-dimethylphenyl)quinazolin-4(3H)-one;
3-(4-sec-butylphenyl)-6-fluoro-2-(4-(2-hydroxyethoxy)-3,5-dimethylphenyl)quinazolin-4(3H)-one,
3-(4-chlorophenyl)-2-(4-(2-hydroxyethoxy)-3,5-dimethylphenyl)quinazolin-4(3H)-one;
3-(4-sec-butylphenyl)-7-fluoro-2-(4-(2-hydroxyethoxy)-3,5-dimethylphenyl)quinazolin-4(3H)-one;
2-(4-(2-hydroxyethoxy)-3,5-dimethylphenyl)-3-(4-(trifluoromethyl)phenyl)quinazolin-4(3H)-one;
3-(4-sec-butylphenyl)-2-(4-(2-hydroxyethoxy)-3,5-dimethylphenyl)-7-(methylsulfonyl)quinazolin-4(3H)-one;
3-(4-sec-butylphenyl)-2-(4-(2-hydroxyethoxy)-3,5-dimethylphenyl)-6-methoxyquinazolin-4(3H)-one;
3-(4-sec-butylphenyl)-2-(4-(2-hydroxyethoxy)-3,5-dimethylphenyl)-8-methoxyquinazolin-4(3H)-one;
3-(4-sec-butylphenyl)-2-(4-(2-hydroxyethoxy)-3,5-dimethylphenyl)pyrido[4,3-d]pyrimidin-4(3H)-one;
3-(4-sec-butylphenyl)-2-(4-(2-hydroxyethoxy)-3,5-dimethylphenyl)-6-(methylsulfonyl)quinazolin-4(3H)-one;
3-(4-bromophenyl)-2-(4-(2-hydroxyethoxy)-3,5-dimethylphenyl)-6-methoxyquinazolin-4(3H)-one;
3-(4-bromophenyl)-2-(4-(2-hydroxyethoxy)-3,5-dimethylphenyl)-8-methoxyquinazolin-4(3H)-one,
2-(4-(2-hydroxyethoxy)-3,5-dimethylphenyl)-3-(4-isopropylphenyl)quinazolin-4(3H)-one;
3-(4-bromophenyl)-2-(4-(2-hydroxyethoxy)-3-methylphenyl)quinazolin-4(3H)-one;
3-(4-bromophenyl)-8-chloro-2-(4-(2-hydroxyethoxy)-3,5-dimethylphenyl)quinazolin-4(3H)-one;
2-(4-(2-hydroxyethoxy)-3,5-dimethylphenyl)-3-(4-morpholinophenyl)quinazolin-4(3H)-one;
3-(4-tert-butylphenyl)-2-(4-(2-hydroxyethoxy)-3,5-dimethylphenyl)quinazolin-4(3H)-one;
N-(4-(2-(4-(2-hydroxyethoxy)-3,5-dimethylphenyl)-4-oxoquinazolin-3(4H)-yl)phenyl)acetamide;
N-(4-(2-(4-(2-hydroxyethoxy)-3,5-dimethylphenyl)-4-oxoquinazolin-3(4H)-yl)phenyl)isobutyramide;
Methyl 4-(2-(4-(2-hydroxyethoxy)-3,5-dimethylphenyl)-4-oxoquinazolin-3(4H)-yl)benzoate;
3-(4-cyclohexylphenyl)-2-(4-(2-hydroxyethoxy)-3,5-dimethylphenyl)quinazolin-4(3H)-one;
N-(4-(2-(4-(2-hydroxyethoxy)-3,5-dimethylphenyl)-4-oxoquinazolin-3(4H)-yl)phenyl)formamide;
3-(4-aminophenyl)-2-(4-(2-hydroxyethoxy)-3,5-dimethylphenyl)quinazolin-4(3H)-one;
N-(4-(2-(4-(2-hydroxyethoxy)-3,5-dimethylphenyl)-4-oxoquinazolin-3(4H)-yl)phenyl)methanesulfonamide;
N-(4-(2-(4-(2-hydroxyethoxy)-3,5-dimethylphenyl)-4-oxoquinazolin-3(4H)-yl)p
N-(4-(2-(4-(2-hydroxyethoxy)-3,5-dimethylphenyl)-4-oxoquinazolin-3(4H)-yl)phenyl)propane-2-sulfonamide;
3-(4-(dimethylamino)phenyl)-2-(4-(2-hydroxyethoxy)-3,5-dimethylphenyl)quinazolin-4(3H)-one;
3-(4-sec-butylphenyl)-2-(4-(2-hydroxyethoxy)-3-methylphenyl)quinazolin-4(3H)-one;
3-(4-chlorophenyl)-2-(4-(2-hydroxyethoxy)-3-methylphenyl)quinazolin-4(3H)-one;
3-(4-sec-butylphenyl)-2-(pyridin-3-yl)quinazolin-4(3H)-one;
3-(4-chlorophenyl)-2-(quinolin-3-yl)quinazolin-4(3H)-one;

3-(4-sec-butylphenyl)-2-(5-fluoropyridin-3-yl)quinazolin-4(3H)-one;
3-(4-chlorophenyl)-2-(6-chloropyridin-3-yl)quinazolin-4(3H)-one;
3-(4-sec-butylphenyl)-2-(6-chloropyridin-3-yl)quinazolin-4(3H)-one;
3-(4-sec-butylphenyl)-2-(6-methoxypyridin-3-yl)quinazolin-4(3H)-one;
2-(6-bromopyridin-3-yl)-3-(4-chlorophenyl)quinazolin-4(3H)-one;
2-(6-bromopyridin-3-yl)-3-(4-sec-butylphenyl)quinazolin-4(3H)-one;
3-(4-chlorophenyl)-2-(6-(diethylamino)pyridin-3-yl)quinazolin-4(3H)-one;
3-(4-sec-butylphenyl)-2-(6-(diethylamino)pyridin-3-yl)quinazolin-4(3H)-one;
3-(4-sec-butylphenyl)-2-(pyrimidin-5-yl)quinazolin-4(3H)-one,
3-(4-sec-butylphenyl)-2-(6-methylpyridin-3-yl)quinazolin-4(3H)-one;
3-(4-chlorophenyl)-2-(6-methylpyridin-3-yl)quinazolin-4(3H)-one;
3-(4-chlorophenyl)-2-(6-(piperidin-1-yl)pyridin-3-yl)quinazolin-4(3H)-one;
3-(4-sec-butylphenyl)-2-(6-(piperidin-1-yl)pyridin-3-yl)quinazolin-4(3H)-one;
3-(4-chlorophenyl)-2-(6-phenoxypyridin-3-yl)quinazolin-4(3H)-one;
3-(4-sec-butylphenyl)-2-(6-fluoropyridin-3-yl)quinazolin-4(3H)-one;
3-(4-sec-butylphenyl)-2-(6-phenoxypyridin-3-yl)quinazolin-4(3H)-one,
3-(4-chlorophenyl)-2-(6-(trifluoromethyl)pyridin-3-yl)quinazolin-4(3H)-one;
3-(4-sec-butylphenyl)-2-(6-(trifluoromethyl)pyridin-3-yl)quinazolin-4(3H)-one;
3-(4-sec-butylphenyl)-2-(6-phenylpyridin-3-yl)quinazolin-4(3H)-one;
3-(4-sec-butylphenyl)-2-(5-phenylpyridin-3-yl)quinazolin-4(3H)-one;
2-(5-bromopyridin-3-yl)-3-(4-sec-butylphenyl)quinazolin-4(3H)-one;
2-(5-bromopyridin-3-yl)-3-(4-chlorophenyl)quinazolin-4(3H)-one;
3-(4-sec-butylphenyl)-2-(5-(diethylamino)pyridin-3-yl)quinazolin-4(3H)-one;
3-(4-chlorophenyl)-2-(5-phenylpyridin-3-yl)quinazolin-4(3H)-one;
3-(4-chlorophenyl)-2-(5-(diethylamino)pyridin-3-yl)quinazolin-4(3H)-one;
3-(4-cyclopentylphenyl)-2-(6-methylpyridin-3-yl)quinazolin-4(3H)-one;
3-(4-sec-butylphenyl)-2-(6-(hydroxymethyl)pyridin-3-yl)quinazolin-4(3H)-one;
2-(6-methylpyridin-3-yl)-3-(4-(methylthio)phenyl)quinazolin-4(3H)-one;
3-(4-isopropylphenyl)-2-(6-methylpyridin-3-yl)quinazolin-4(3H)-one;
N-(4-(2-(6-methylpyridin-3-yl)-4-oxoquinazolin-3(4H)-yl)phenyl)methanesulfonamide;
3-(4-sec-butylphenyl)-2-(6-(morpholinomethyl)pyridin-3-yl)quinazolin-4(3H)-one;
3-(4-cyclopropylphenyl)-2-(6-methylpyridin-3-yl)quinazolin-4(3H)-one;
3-(4-(dimethylamino)phenyl)-2-(6-methylpyridin-3-yl)quinazolin-4(3H)-one;
2-(6-chloropyridin-3-yl)-3-(4-cyclopropylphenyl)quinazolin-4(3H)-one; and
3-(4-sec-butylphenyl)-2-(6-morpholinopyridin-3-yl)quinazolin-4(3H)-one,
3-(4-sec-butylphenyl)-2-(1H-indazol-5-yl)quinazolin-4(3H)-one;
3-(4-chlorophenyl)-2-(1H-indol-5-yl)quinazolin-4(3H)-one;
3-(4-sec-butylphenyl)-2-(1H-indol-5-yl)quinazolin-4(3H)-one;
3-(4-sec-butylphenyl)-2-(2-(hydroxymethyl)-1H-benzo[d]imidazol-6-yl)quinazolin-4(3H)-one;
2-(1H-indol-5-yl)-3-(4-(trifluoromethoxy)phenyl)quinazolin-4(3H)-one;
2-(1H-indol-5-yl)-3-(4-isopropylphenyl)quinazolin-4(3H)-one;
3-(4-chlorophenyl)-2-(1-(4-methoxyphenylsulfonyl)-1H-pyrrolo[2,3-b]pyridin-5-yl)quinazolin-4(3H)-one;
3-(4-chlorophenyl)-2-(1-(4-fluorophenylsulfonyl)-1H-pyrrolo[2,3-b]pyridin-5-yl)quinazolin-4(3H)-one;
3-(4-(dimethylamino)phenyl)-2-(1H-indol-5-yl)quinazolin-4(3H)-one;
3-(4-chlorophenyl)-2-(1-(phenylsulfonyl)-1H-pyrrolo[2,3-b]pyridin-5-yl)quinazolin-4(3H)-one;
3-(4-sec-butylphenyl)-2-(2-(hydroxymethyl)-1H-indol-5-yl)quinazolin-4(3H)-one;
3-(4-chlorophenyl)-2-(1-methyl-1H-indol-5-yl)quinazolin-4(3H)-one;
3-(4-cyclopentylphenyl)-2-(1H-indol-5-yl)quinazolin-4(3H)-one;
3-(4-chlorophenyl)-2-(1H-indol-6-yl)quinazolin-4(3H)-one;
3-(4-chlorophenyl)-2-(1H-indol-7-yl)quinazolin-4(3H)-one;
3-(4-sec-butylphenyl)-2-(1H-indol-6-yl)quinazolin-4(3H)-one;
3-(4-sec-butylphenyl)-2-(1H-indol-7-yl)quinazolin-4(3H)-one;
3-(4-chlorophenyl)-2-(1H-indol-4-yl)quinazolin-4(3H)-one; and
3-(4-sec-butylphenyl)-2-(1H-indol-4-yl)quinazolin-4(3H)-one,
and pharmaceutically acceptable salts and hydrates thereof.

11. A pharmaceutical composition comprising a compound according to claim 1, 3, 6, or 10 and a pharmaceutically acceptable carrier.

12. A method of increasing the expression of ApoA-I in a subject, comprising administering a therapeutically effective amount of a compound according to claim 1, 3, 6, or 10.

13. The method of claim 12, wherein increasing the expression of ApoA-I in the subject treats a cardiovascular disease or a cholesterol-, or lipid-related disorder or reduces the risk of acquiring a cardiovascular disease or cholesterol-, or lipid-related disorder.

14. The method of claim 13, wherein the method comprises regression of arteriosclerosis lesions or reduction of the risk of acquiring arteriosclerosis lesions.

15. The method of claim 13, wherein the method comprises decreasing blood cholesterol levels.

16. The method of claim 12, wherein the subject has a genetic or non-genetic predisposition to a cardiovascular disease or cholesterol- or lipid related disorder.

* * * * *

UNITED STATES PATENT AND TRADEMARK OFFICE
CERTIFICATE OF CORRECTION

PATENT NO. : 8,952,021 B2
APPLICATION NO. : 13/143757
DATED : February 10, 2015
INVENTOR(S) : Henrik C. Hansen Page 1 of 1

It is certified that error appears in the above-identified patent and that said Letters Patent is hereby corrected as shown below:

In the Claims

Claim 3, Col. 92, Line 17, "W is carbon or nitrogen" should read as --W is nitrogen--.

Claim 5, Col. 92, Line 66, "together to which the atoms they are bound" should read as --are connected to--.

Claim 10, Col. 94, Lines 53-54, "N-(4-(2-(4-(2-hydroxyethoxy)-3,5-dimethylphenyl)-4-oxoquinazolin-3(4H)-yl)p" should read as --N-(4-(2-(4-(2-hydroxyethoxy)-3,5-dimethylphenyl)-4-oxoquinazolin-3(4H)-yl)phenyl)benzenesulfonamide--.

Claim 10, Col. 96, Line 4, remove "and".

Signed and Sealed this
Thirtieth Day of June, 2015

Michelle K. Lee
*Director of the United States Patent and Trademark Office*